US009066938B2

(12) United States Patent
Saus et al.

(10) Patent No.: US 9,066,938 B2
(45) Date of Patent: Jun. 30, 2015

(54) GPBP-1 INHIBITION AND ITS THERAPEUTIC USE

(71) Applicants: Fibrostatin S.L., Valencia (ES); Universitat de Valencia, Valencia (ES)

(72) Inventors: Juan Saus, Valencia (ES); Francisco Revert-Ros, Valencia (ES); Fernando Revert, Valencia (ES); Carmen Aguado-Velasco, Valencia (ES); Ernesto López-Pascual, Valencia (ES); Alejandra María Pérez-Sastre, Valencia (ES); Raúl Blasco, Valencia (ES); Héctor Pérez-Montoyo, Valencia (ES)

(73) Assignees: Fibrostein, S.L., Valencia (ES); Universitat de Valencia, Valencia (ES)

( * ) Notice: Subject to any disclaimer, the term of this patent is extended or adjusted under 35 U.S.C. 154(b) by 15 days.

(21) Appl. No.: 13/933,609

(22) Filed: Jul. 2, 2013

(65) Prior Publication Data

US 2014/0005134 A1    Jan. 2, 2014

Related U.S. Application Data

(60) Provisional application No. 61/667,057, filed on Jul. 2, 2012.

(51) Int. Cl.
| | | |
|---|---|---|
| *A01N 43/04* | (2006.01) | |
| *A61K 31/70* | (2006.01) | |
| *A61K 31/4406* | (2006.01) | |
| *A61K 31/704* | (2006.01) | |
| *A61K 31/357* | (2006.01) | |
| *A61K 31/192* | (2006.01) | |
| *A61K 31/194* | (2006.01) | |
| *A61K 31/216* | (2006.01) | |
| *A61K 45/06* | (2006.01) | |
| *A61K 31/4418* | (2006.01) | |

(52) U.S. Cl.
CPC ........... *A61K 31/4406* (2013.01); *A61K 31/704* (2013.01); *A61K 31/357* (2013.01); *A61K 31/192* (2013.01); *A61K 31/194* (2013.01); *A61K 31/216* (2013.01); *A61K 45/06* (2013.01); *A61K 31/4418* (2013.01)

(58) Field of Classification Search
None
See application file for complete search history.

(56) References Cited

U.S. PATENT DOCUMENTS

| 5,625,048 | A  | 4/1997 | Tsien et al. |
| 6,124,128 | A  | 9/2000 | Tsien et al. |
| 6,579,969 | B1 | 6/2003 | Saus et al. |
| 6,881,547 | B1 | 4/2005 | Saus et al. |
| 7,326,768 | B2 | 2/2008 | Saus et al. |
| 7,935,492 | B2 | 5/2011 | Saus et al. |
| 2011/0105545 | A1* | 5/2011 | Saus et al. ............ 514/277 |

FOREIGN PATENT DOCUMENTS

| WO | 00/50607 | 8/2000 |
| WO | 02/061430 | 8/2002 |
| WO | 2011/054530 | 5/2011 |
| WO | 2012/078593 | 6/2012 |
| WO | 2012/113785 | 8/2012 |

OTHER PUBLICATIONS

Danesi et al. Trends in Pharmacological Sciences (2001), vol. 22, pp. 420-426.*
Perry et al., "Molecular mechanism and regulation of ceramide transport," BBA Acta, 2005, 1734: 220-234.
Levine et al., "Inter-organelle membrane contact sitesL through a glass, darkly," Curr Op Cell Biol, 2006, 18:371-378.
Perry et al "Oxysterol-binding Protein and Vesicle-associated Membrane Protein-associated Protein Are Required for Sterol-dependent Activation of the Ceramide Transport Protein," Molecular Biology of the Cell, 2006,17: 2604-2616.
Tóth et al "Phosphatidylinositol 4-Kinase IIIb Regulates the Transport of Ceramide between the Endoplasmic Reticulum and Golgi," JBC, 2006, 281(47): 36369-36377.
Kudo et al., "Structural basis for specific lipid recognition by CERT responsible for nonvesicular trafficking of ceramide," PNAS, 2008, 105(2): 488-493.
Lamour et al., "Ceramide kinase uses ceramide provided by ceramide transport protein: localization to organelles of eicosanoid synthesis," J Lipid Res, 2007, 48:1293-1304.
Rao et al., "Ceramide transfer protein function is essential for normal oxidative stress response and lifespan," PNAS, 2007, 104(27): 11364-11369.
Sano et al, "Sphingomyelin-dependence of cholesterol efflux mediated by ABCG1," J Lipid Res, 2007, 48:2377-2384.
Saito et al., "Protein Phosphatase 2Ce Is an Endoplasmic Reticulum Integral Membrane Protein That Dephosphorylates the Ceramide Transport Protein CERT to Enhance Its Association with Organelle Membranes," J Biol Chem, 2008, 283(10):6584-6593.
Chandran et al, "Acute perturbations in Golgi organization impact de nova sphingomyelin synthesis," Traffic, 2008, 9(11): 1894-1904.
Holeiter, et al., "Deleted in Liver Cancer 1 Controls Cell Migration through a Dia1-Dependent Signaling Pathway," Cancer Res, 2008, 68:8743-8751.
Peretti et al, "Coordinated Lipid Transfer between the Endoplasmic Reticulum and the Golgi Complex Requires the VAP Proteins and Is Essential for Golgi-mediated Transport," MCB, 2008, 19: 3871-3884.
Florin et al., "Heterologous expression of the lipid transfer protein CERT increases therapeutic protein productivity of mammalian cells," J Biotechnol, 2009,141, 84-90.

(Continued)

*Primary Examiner* — Patrick Lewis
(74) *Attorney, Agent, or Firm* — McDonnell Boehnen Hulbert & Berghoff LLP

(57) ABSTRACT

The present invention provides compositions including antitumor agents and inhibitors of Goodpasture antigen binding protein, p21, and ABCC7, and their use in treating cancer.

35 Claims, 12 Drawing Sheets

(56) References Cited

OTHER PUBLICATIONS

Wang et al., "Mitochondrial degeneration and not apoptosis is the primary cause of embryonic lethality in ceramide transfer protein mutant mice," JCB, 2009, 184(1):143-158.

Banerji S et al, Oxysterol Binding Protein-dependent Activation of Sphingomyelin Synthesis in the Golgi Apparatus Requires Phosphatidylinositol 4-Kinase IIa MBC, 2010, 21:4141-4150.

Domingo B et al, "Discrimination between alternate membrane protein topologies in living cells using GFP/YFP tagging and pH exchange," Cell Mol Life Sci, 2010, 67:3345-3354.

Guo et al, "Palmitate-Induced Inhibition of Insulin Gene Expression in Rat Islet B-Cells Involves the Ceramide Transport Protein," Cell Physiol Biochem, 2010, 26:717-728.

Juul et al., "Assessment of an RNA interference screen-derived mitotic and ceramide pathway metagene as a predictor of response to neoadjuvant paclitaxel for primary triple-negative breast cancer: a retrospective analysis of five clinical trials," Lancet Oncol, 2010, 11: 358-365.

Lev S, "Non-vesicular lipid transport by lipid-transfer proteins and beyond," Nat Review, 2010,11: 1739-750.

Nhek et al, "Regulation of Oxysterol-binding Protein Golgi Localization through Protein Kinase D-mediated Phosphorylation," MCB, 2010, 21: 2327-2337.

Spessott W et al, "Cog2 null mutant CHO cells show defective sphingomyelin synthesis," J Biol Chem, 2010, 285(53):41472-41482.

Mencarelli et al., "The Goodpasture-Antigen Binding Protein / Ceramide Transporter Binds to Human Serum Amyloid P-Component and is present in Brain Amyloid Plaques," J. Neurochem 2010, 113, 1369-1386.

Cherilyn et al., "Chlamydia trachomatis Co-opts GBF1 and CERT to Acquire Host Sphingomyelin for Distinct Roles during Intracellular Development,"PLoS Pathogens, 2011, 7(9): e1002198.

Derré, et al., "The Lipid Transfer Protein CERT Interacts with the Chlamydia Inclusion Protein IncD and Participates to ER-Chlamydia Inclusion Membrane Contact Sites," PLoS Pathogens, 2011, 7(6): e1002092.

Olayioye and Hausser, "Integration of non-vesicular and vesicular transport processes at the Golgi complex by the PKD-CERT network," BB Acta 1821, 2012, 1096-1103.

Subtil, "Rerouting of Host Lipids by Bacteria: Are You CERTain You Need a Vesicle?" PLoS Pathogens, 2011, 7(9):e1002208.

Bishé et al, "Phosphoinositides in the Hepatitis C Virus Life Cycle," Viruses, 2012, 4: 2340-2358.

Blom, et al, "Tracking Sphingosine Metabolism and Transport in Sphingolipidoses: NPC1 Deficiency as a Test Case," Traffic, 2012, 13:1234-1243.

Chandran & Machamer, "Inactivation of ceramide transfer protein during proapoptotic stress by Golgi disassembly and caspase cleavage," Biochem J, 2012, 442, 391-401.

Heering et al, "Loss of the Ceramide Transfer Protein Augments EGF Receptor Signaling in Breast Cancer," Cancer Research, 2012, 72:2855-2866.

Kujjo & Perez, "Ceramide and mitochondrial function in aging oocytes: joggling a new hypothesis and old players," Reproduction, 2012, 143:1-10(online).

Hanada et al., "CERT-mediated trafficking of ceramide," BBActa 2009, 1791:684-691.

Tomishige et al., "Casein Kinase I(gamma)2 Down-Regulates Trafficking of Ceramide in the Synthesis of Sphingomyelin," MCB, 2009, 20: 348-357.

Nakamura et al, "Modulation of the activity of cytosolic phopholipase A2a (cPLA2a) by cellular sphingolipids and inhibition of cPLA2a by sphingomyelin," J. Lipid Res, 2010, 51(4): 720-728.

Hanada, et al. "Intracellular traffking of ceramide by ceramide transfer protein," Proc. Jpn. Acad Ser. 2010, B 86:426.

Tuuf, et al., "The intermembrane ceramide transport catalyzed by CERT is sensitive to the lipid environment," BBActa 2011, 1808: 229-235.

Kumagai et al., "CERT Mediates Intermembrane Transfer of Various Molecular Species of Ceramides" J Biol Chem, 2005, 280(8):6488-6495.

Hanada, "Discovery of the molecular machinery CERT for endoplasmic reticulum-to-Golgi trafficking of ceramide," Molecular and Cellular Biochemi, 2006, 286: 23-31.

Kawano et al., "Efficient Trafficking of Ceramide from the Endoplasmic Reticulum to the Golgi Apparatus Requires a VAMP-associated Protein-interacting FFAT Motif of CERT," J Biol Chem, 2006, 281(40): 30279-30288.

Hanada et al.,"CERT and intracellular trafficking of ceramide," BBActa, 2007, 1771:644-653.

Kumagai et al., "Interorganelle Trafficking of Ceramide Is Regulated by Phosphorylation-dependent Cooperativity between the PH and START Domains of CERT," J Biol Chem, 2007, 282(24):17758-17766.

Nagao et al., "Enhanced ApoA-I-dependent Cholesterol Efflux by ABCA1 from Sphingomyelin-deficient Chinese Hamster Ovary Cells," J Biol Chem, 2007, 282(20):14868-14874.

Charruyer, "Decreased Ceramide Transport Protein (CERT) Function Alters Sphingomyelin Production following UVB Irradiation," J Biol Chem, 2008, 283(24):16682-16692.

Giussani et al., "Ceramide traffic in C6 glioma cells: Evidence for CERT-dependent and independent transport from ER to the Golgi apparatus," BB Acta, 2008,1781 40-51.

Alberts, B, Johnson A, Lewis J, RaffM, Roberts K, Walter P, 2007. Molecular Biology of the Cell, 5th Ed., ISBN: 9780815341055.

Bartek J, Lukas J. 2001. Mammalian G 1- and S-phase checkpoints in response to DNA damage. Curro Opin. Cell. Biol. 13: 738-47.

Benjamini Y, Hochberg Y. 1995. Controlling the False Discovery Rate: a Practical Powerful Approach to Multiple Testing. J R Statist Soc B, 57: 289-300.

Bunz F, Dutriaux A, Lengauer C, Waldman T, Zhou S, Brown JP, Sedivy JM, Kinzler KW, Vogelstein B. 1998. Requirement for p53 and p21 to sustain G2 arrest after DNA damage. Science. 282: 1497-501.

Dean M. 2009. ABC Transporters, Drug Resistance, and Cancer Stem Cells. J. Mammary Gland. Biol. Neoplasia. 14:3-9.

Faizul FM, Abdul Kadir H, Tayyab S. 2008. Spectroscopic studies on the binding of bromocresol purple to different serum albumins and its bilirubin displacing action. J. Photochem. Photobiol. B. 90: 1-7.

Fugmann T, Hausser A, Schoffler P, Schmid S, pfizenmaier K, Olayioye MA. 2007. Regulation of secretory transport by protein kinase D-mediated phosphorylation of the ceramide transfer protein. J. Cell. Biol. 178: 15-22.

Ho MM, Ng AV, Lam S, Hung JY. 2007. Side population in human lung cancer cell lines and tumors is enriched with stem-like cancer cells. Cancer Res. 67: 4827-33.

Kim H, Jang C, Choe J, Sohn J, Kim J. 2012. Phenylbutyric acid induces the cellular senescence through an Akt/p211waf signaling pathway. Biochem. Biophys. Res. Commun. 422: 213-18.

Lai HC, Yeh YC, Ting CT, Lee WL, Lee HW, Wang LC, Wang KY, Lai HC, Wu A, Liu TJ. 2010. Eur. J. Pharmacol. 644:176-87.

Lazebnik YA, Kaufmann SH, Desnoyers S, Poirier GG, Earnshaw WC. 1994. Cleavage of poly(ADP-ribose) polymerase by a proteinase with properties like ICE. Nature. 371: 346-7, 1994.

Mihailidou C, Papazian I, Papavassiliou A, Kiaris H. 2010. CHOP-dependent regulation ofp211wafl during ER stress. Cell. Physiol. Biochem. 25: 761-66.

Pommier Y, Leo E, Zhang H, Marchand C. 2010. DNA topoisomerases and their poisoning by anticancer and antibacterial drugs. Chem. Biol. 17: 421-33.

Raya A, Revert F, Navarro S, Saus J.1999. Characterization of a novel type of serine/threonine kinase that specifically phosphorylates the human goodpasture antigen. J. Biol. Chem. 274: 12642-12649.

Raya A, Revert-Ros F, Martinez-Martinez P, Navarro S, Rosello E, Vieites B, Granero F, Forteza J, Saus J. 2000. Goodpasture antigen-binding protein, the kinase that phosphorylates the Goodpasture antigen, is an alternatively spliced variant implicated in autoimmune pathogenesis. J. Biol. Chem. 275: 40392-9.

(56) References Cited

OTHER PUBLICATIONS

Regala RP, Justilien V, Walsh MP, Weems C, Khoor A, Murray NR, Fields AP. 2011. Matrix metalloproteinase-10 promotes Kras-mediated bronchio-alveolar stem cell expansion and lung cancer formation. PLoS One. 6: e26439.

Revert F, Merino R, Monteagudo C, Macias J, Peydró A, Alcacer J, Muniesa P, Marquina R, Blanco M, Iglesias M, Revert-Ros F, Merino J, Saus J. 2007. Increased Goodpasture antigen-binding protein expression induces type IV collagen disorganization and deposit of immunoglobulin A in glomerular basement membrane. Am. J. Pathol. 171:1419-30.

Revert F, Ventura I, Martinez-Martinez P, Granero-Moltó F, Revert-Ros F, Macias J, Saus J. 2008. Goodpasture antigen-binding protein is a soluble exportable protein that interacts with type IV collagen. Identification of novel membrane-bound isoforms. J. Biol. Chem. 283: 30246-55.

Seoane J, Le HV, Massague J. 2002. Myc suppression of the p21(Cipl) Cdk inhibitor influences the outcome of the p53 response to DNA damage. Nature. 419: 729-34.

Sithanandam G, Fornwald LW, Fields J, Anderson LM. 2005. Inactivation of ErbB3 by siRNA promotes apoptosis and attenuates growth and invasiveness of human lung adenocarcinoma cell line A549. Oncogene. 24: 1847-59.

Swanton C, Marani M, Pardo 0, Warne PH, Kelly G, Sahai E, Elustondo F, Chang J, Temple J, Ahmed AA, Brenton JD, Downward J, Nicke B. 2007. Regulators of mitotic arrest and ceramide metabolism are determinants of sensitivity to paclitaxel and other chemotherapeutic drugs. Cancer Cell. 11: 498-512.

Vasiliou V, Vasiliou K, Nebert DW. 2009. Human ATP-binding cassette (ABC) transporter family. Hum. Genomics. 3:281-90.

Zinszner H, Kuroda M, Wang X, Batchvarova N, Lightfoot RT, Remotti H, Stevens JL, Ron D. 1998. CHOP is implicated in programmed cell death in response to impaired function of the endoplasmic reticulum. Genes Dev. 12:982-95.

ISR for PCT/EP2013/063892, mailed Nov. 13, 2013.

Yin, et al. "Terphenyl-based BAK BH3 alpha-helical proteomimetics as low-molecular-eight antagonists of Bcl-xL," Journal of the American Chemical Society, 2005, 127(29):10191-10196.

Gianni, et al., "Experience at the Istituto Tumori with Paclitaxel in combination with Doxorubicin in women with untreated breast cancer," Seminars in Oncology, 1997, 24(1Supp 3): S1-3.

Lee, et al., "Enhancement of cytotoxicity by the combination of anticancer drugs in human lung adenocarcinoma cell lines," Tuberculosis and Respiratory Diseases, 1997, 44(3): 525-533, abstract.

Kutzki, et al., "Development of a potent Bcl-xL antagonist based on alpha-helix mimicry," Journal of the American Chemical Society, 2002, 124(40): 11838-11839.

Wong, et al., "Navitoclax (ABT-263) reduced Bcl-xL-mediated chemoresistance in ovarian cancer models," Molecular Caner Therapeutics, 2012, 11(4): 1026-1035.

Granero, et al. "A human-specific TNF-responsive promoter for Goodpasture antigen-binding protein," FEBS, 2005, 272(20): 5291-305.

Revert-Ros, et al., "Goodpasture antigen-binding protein (GPBP) directs myofibril formation: identification of intracellular downstream effector 130-kDa GPBP-interacting protein (GIP130)," Journal of Biological Chemistry, 2011, 286(40):35030-43.

Miralem, et al, "Human biliverdin reductase suppresses Goodpasture antigen-binding protein (GPBP) kinase activity: the reductase regulates tumor necrosis factor-alpha-NF-kappaB-dependent GPBP expression," Journal of Biological Chemistry, 2010, 285(17):12551-8.

Granero-Molto, et al., "Goodpasture antigen-binding protein and its spliced variant, ceramide transfer protein, have different functions in the modulation of apoptosis during zebrafish development," Journal of Biological Chemistry, 2008, 283(29): 20495-504.

Hanada et al., "Molecular machinery for non-vesicular trafficking of ceramide," Nature, 2003, 426(18): 803-809.

\* cited by examiner

A

B

GPBP-1 INHIBITION AND ITS THERAPEUTIC USE

CROSS REFERENCE

This application claims priority to U.S. Provisional Patent Application Ser. No. 61/667,057 filed Jul. 2, 2012, incorporated by reference herein in its entirety.

BACKGROUND OF THE INVENTION

The conformation of the non-collagenous (NC1) domain of the α3 chain of the basement membrane collagen IV [α3(IV)NC1] depends in part on phosphorylation. Goodpasture Antigen Binding Protein (GPBP) (WO 00/50607; WO 02/061430) is a non-conventional protein kinase that catalyzes the conformational isomerization of the α3(IV)NC1 domain during its supramolecular assembly, resulting in the production and stabilization of multiple α3(IV)NC1 conformers in basement membranes. Increased expression levels of GPBP-1 (also known as 77 kD GPBP or GPBP) have been associated with the production of aberrant non-tolerized α3(IV)NC1 conformers, which conduct the autoimmune response mediating Goodpasture ("GP") syndrome. In GP patients, autoantibodies against the α3(IV)NC1 domain ("Goodpasture antigen" or "GP antigen") cause a rapidly progressive glomerulonephritis and often lung hemorrhage, the two cardinal clinical manifestations of the GP syndrome. Furthermore, it has been proposed that GPBP regulates inflammation, apoptosis and protein folding, and that increased GPBP expression induces antibody-mediated glomerulonephritis (IgA nephropathy, systemic lupus erythematosus and Goodpasture autoimmune syndrome) and resistance of cancer cells to a number of chemotherapeutic agents including those inducing protein misfolding-mediated endoplasmic reticulum (ER) stress (i.e. paclitaxel). Thus, inhibitors of GPBP are useful for the treatment of antibody-mediated disorders, drug-resistant cancer, inflammation, protein misfolding and ER stress-mediated disorders, and aberrant apoptosis.

SUMMARY OF THE INVENTION

In a first aspect, the present invention provides pharmaceutical compositions, comprising:
(a) an antitumor drug or a pharmaceutically acceptable salt thereof;
(b) a compound of formula:

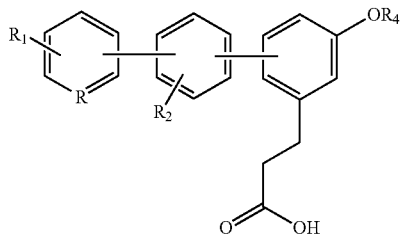

or a pharmaceutically acceptable salt thereof, wherein:
R is selected from N and $CR_3$;
$R_1$ is hydrogen or $C_1$-$C_6$ alkoxy;
$R_2$ is $C_1$-$C_6$ alkyl or halo($C_1$-$C_6$ alkyl);
$R_3$, if present, is halogen, $C_1$-$C_6$ alkyl or halo($C_1$-$C_6$ alkyl); and
$R_4$ is H or $C_1$-$C_6$ alkyl; and
(c) a pharmaceutically acceptable carrier.

In a second aspect, the present invention provides methods for treating a tumor, comprising administering to a subject with a tumor an amount effective to treat the tumor of:
(a) an antitumor drug; and
(b) a compound of formula:

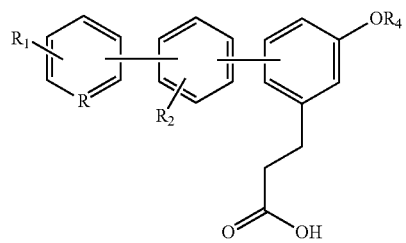

or a pharmaceutically acceptable salt thereof, wherein:
R is selected from N and $CR_3$;
$R_1$ is hydrogen or $C_1$-$C_6$ alkoxy;
$R_2$ is $C_1$-$C_6$ alkyl or halo($C_1$-$C_6$ alkyl);
$R_3$, if present, is halogen, $C_1$-$C_6$ alkyl or halo($C_1$-$C_6$ alkyl); and
$R_4$ is H or $C_1$-$C_6$ alkyl.

In a further embodiment, the invention provides methods for treating a tumor, comprising administering to a subject with a tumor an amount effective to treat the tumor of
(a) an antitumor drug; and
(b) a GPBP-1 inhibitor.

In a further aspect, the present invention provides compounds of formula:

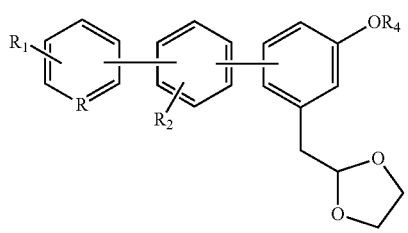

or a pharmaceutically acceptable salt thereof, wherein:
R is selected from N and $CR_3$;
$R_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)($C_1$-$C_6$ alkoxy), —$(CH_2)_{1-5}$—$C(O)NH_2$, (aryl)$C_2$-$C_6$ alkyl, and (heteroaryl)$C_1$-$C_6$ alkyl;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—$C(O)NH_2$, —$(CH_2)_{1-5}$—C(O)NH ($C_1$-$C_6$ alkyl), —$(CH_2)_{1-5}$—C(O)N($C_1$-$C_6$ alkyl)$_2$, —CH=CH—C(O)OH, or —CH=CH—C(O)O($C_1$-$C_6$ alkoxy); and $R_4$ is hydrogen, $C_1$-$C_6$ alkyl, or (aryl)$C_1$-$C_6$ alkyl.

In another aspect, the present invention provides methods for treating a tumor, comprising administering to a subject with a tumor an amount effective to treat the tumor of a compound of formula:

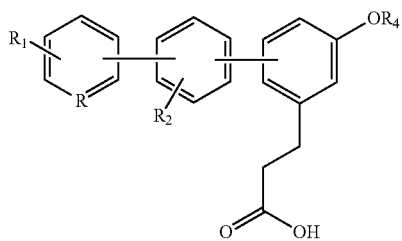

or a pharmaceutically acceptable salt thereof, wherein:
R is selected from N and $CR_3$;
$R_1$ is hydrogen or $C_1$-$C_6$ alkoxy;
$R_2$ is $C_1$-$C_6$ alkyl or halo($C_1$-$C_6$ alkyl);
$R_3$, if present, is halogen, $C_1$-$C_6$ alkyl or halo($C_1$-$C_6$ alkyl); and
$R_4$ is H or $C_1$-$C_6$ alkyl.

DETAILED DESCRIPTION OF THE INVENTION

Figure 1:
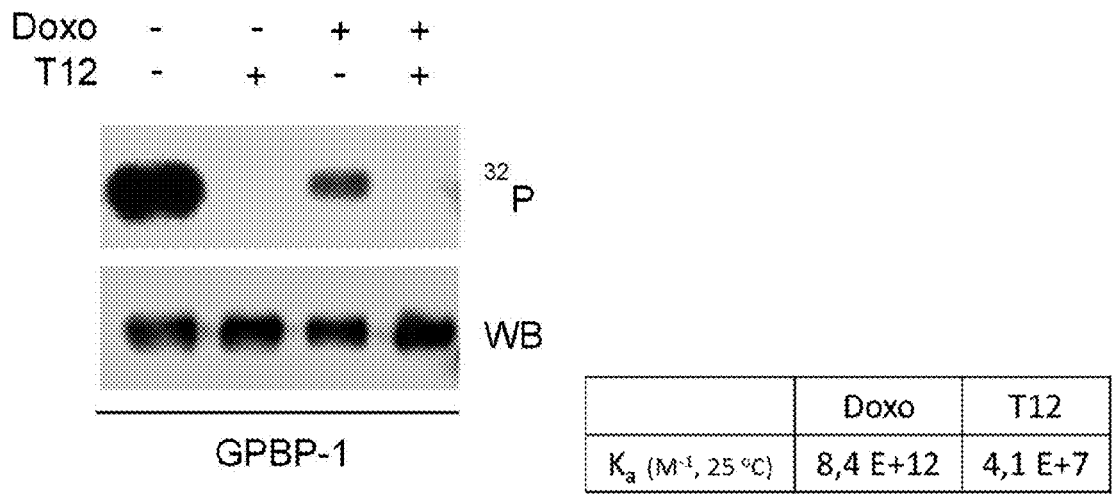
FIG. 1. Doxorubicin inhibits GPBP-1. A, to assess the inhibitory activity of T12 and doxorubicin on GPBP-1 kinase activity and their synergism, approximately 200 ng of yeast FLAG-GPBP-1 from two different preparations with low and high specific activities were incubated with [$\gamma$-$^{32}$P]ATP in the absence (−) or presence (+) of the indicated compounds and concentrations. Mixtures were subjected to Western blot and autoradiographed ($^{32}$P). The levels of GPBP were further analyzed using anti-FLAG (WB). B, in the panel is shown affinity constants of the indicated compounds for recombinant human GPBP-1 produced in insect cells calculated by the Benesi-Hildebrand method.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, $2^{nd}$ Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All common terms between different aspects and embodiments of the invention have the same meaning unless the context clearly dictates otherwise.

Unless clearly indicated otherwise by the context, embodiments disclosed for one aspect of the invention can be used in other aspects of the invention as well, and in combination with embodiments disclosed in other aspects of the invention.

In a first aspect, the present invention provides pharmaceutical compositions, comprising:

(a) an anti-tumor drug, or a pharmaceutically acceptable salt thereof;

(b) a Goodpasture antigen binding protein-1 (GPBP-1) inhibitor, or a pharmaceutically acceptable salt thereof; and (c) a pharmaceutically acceptable carrier.

As used herein the term "GPBP" refers to any polypeptide isoform (such as GPBP-1, -2 and -3 and derived polypeptides) expressed from COL4A3BP gene. As used herein, the term "GPBP-1 inhibitor" means any compound that reduces the expression or activity (such as the kinase activity) of GPBP-1 and which may or may not reduce the expression or activity (such as the kinase activity) of other GPBP isoforms. GPBP-1 is a nonconventional Ser/Thr kinase displaying autophosphorylation activity that binds and phosphorylates the noncollagenous (NC1) domain of human type IV collagen α3 chain [α3(IV)NC1] (Raya et al. 1999 and 2000). GPBP-1 forms large multimeric aggregates whose specific kinase activity is much higher than that of aggregates of lower molecular weight (Raya et al. 2000).

Any suitable GPBP inhibitor may be used in the pharmaceutical compositions of the invention. In one preferred embodiment, the GPBP-1 inhibitor is a compound of formula (A):

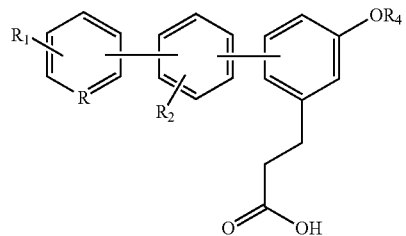

or a pharmaceutically acceptable salt thereof, wherein:
R is selected from N and $CR_3$; $R_1$ is hydrogen or $C_1$-$C_6$ alkoxy; $R_2$ is $C_1$-$C_6$ alkyl or halo($C_1$-$C_6$ alkyl); $R_3$, if present, is halogen, $C_1$-$C_6$ alkyl or halo($C_1$-$C_6$ alkyl); and $R_4$ is H or $C_1$-$C_6$ alkyl.

In one preferred embodiment of the compound of formula (A), $R_1$ is hydrogen or $C_1$-$C_6$ alkoxy; $R_2$ is $C_1$-$C_6$ alkyl or halo($C_1$-$C_6$ alkyl); $R_3$, if present, is $C_1$-$C_6$ alkyl or halo($C_1$-$C_6$ alkyl); and $R_4$ is H or $C_1$-$C_6$ alkyl.

In another preferred embodiment of the compound of formula (A), $R_1$ is hydrogen or methoxy; $R_2$ is methyl, fluoromethyl, or difluoromethyl; $R_3$, if present, is chloro, methyl, or trifluoromethyl; and $R_4$ is H or methyl.

In another preferred embodiment of the compound of formula (A), $R_1$ is hydrogen or methoxy; $R_2$ is methyl, fluoromethyl, or difluoromethyl; $R_3$, if present, is methyl or trifluoromethyl; and $R_4$ is H or methyl.

In various further preferred embodiments, $R_1$ is hydrogen and/or $R_4$ is methyl. In further preferred embodiments, the compound of formula (A) is selected from the group consisting of:

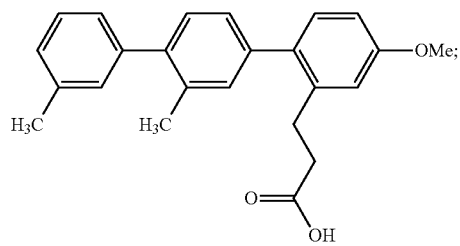 [SMILES: COc1ccc(-c2ccc(-c3cccc(C)c3)c(C)c2)c(CCC(=O)O)c1]

-continued

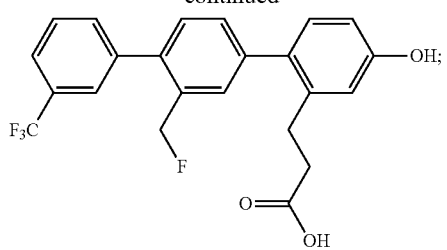

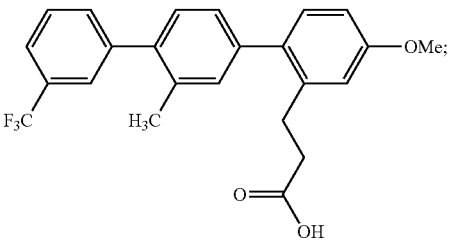

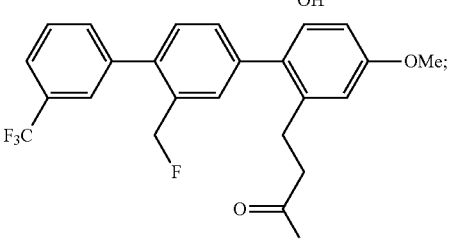

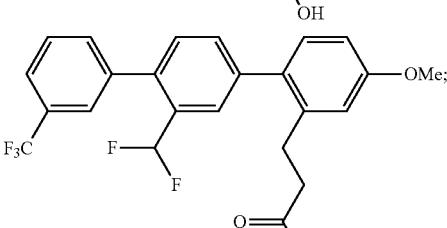

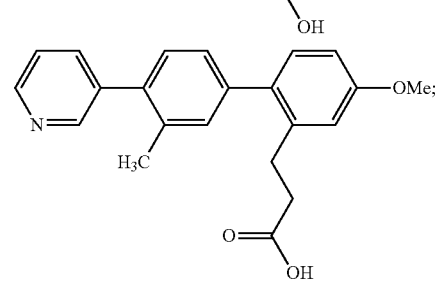

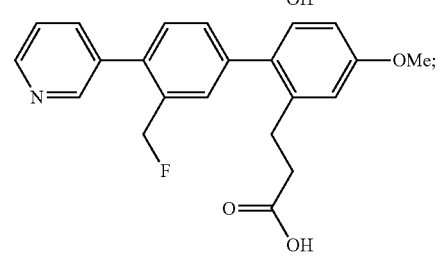

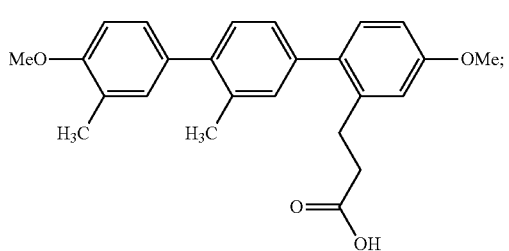

-continued

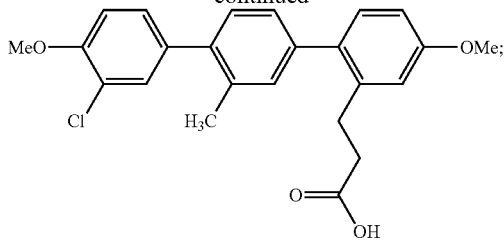

or a pharmaceutically acceptable salt thereof. In a most preferred embodiment, the compound is

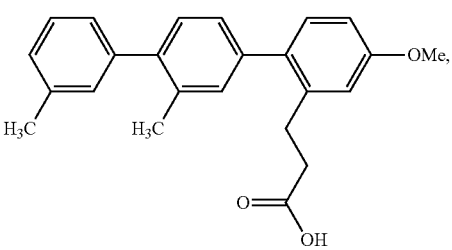

or a pharmaceutically acceptable salt thereof.

The inventors have discovered that the GPBP-1 inhibitors of the invention can act synergistically with anti-tumor agents to provide a more effective therapeutic option for treating tumors, and that the inhibitors of formula A provide particularly good activity. While not being bound by a specific mechanism of action, the inventors believe that GPBP-1 inhibitors, such as those of general formula (A) and embodiments thereof, are synergistic with anti-tumor agents (exemplified by doxorubicin) in treating tumors because both compounds act to inhibit GPBP kinase in a different fashion, and because the GPBP-1 inhibitors reduce viability of cancer stem cells (CSC) in the tumor. CSC are expected to be responsible for drug resistance because they are not likely to be killed by antimitotic drugs since they divide slowly and they have abundant xenobiotic transporters, among other characteristics.

In another preferred embodiment, the GPBP-1 inhibitor is a compound of formula (B):

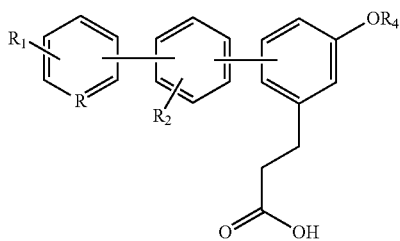

or a pharmaceutically acceptable salt thereof, wherein:
R is selected from N and $CR_3$;
$R_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)

($C_1$-$C_6$ alkoxy), —($CH_2$)$_{1-5}$—C(O)$NH_2$, (aryl)$C_2$-$C_6$ alkyl, and (heteroaryl)$C_1$-$C_6$ alkyl;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), or hydroxy($C_1$-$C_6$ alkyl); and $R_4$ is H, $C_1$-$C_6$ alkyl, —C(O)($C_1$-$C_{20}$ alkyl), or —($CH_2$)$_{1-5}$—C(O)OH.

In another embodiment the GPBP-1 inhibitor of formula B is a compound of formula (C):

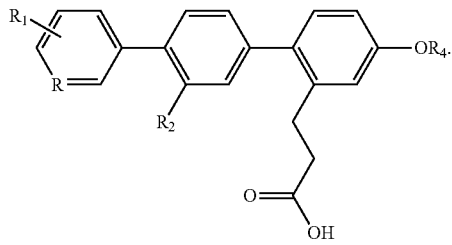

or a pharmaceutically acceptable salt thereof.

In one embodiment of the GPBP-1 inhibitors of formulae (B) or (C), R is selected from N and $CR_3$; $R_3$ is selected from the group consisting of hydrogen, halogen, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, or halo($C_1$-$C_6$ alkoxy); $R_1$ is hydrogen, hydroxy, $C_1$-$C_6$ alkyl, or $C_1$-$C_6$ alkoxy; $R_2$ is $C_1$-$C_6$ alkyl, halo($C_1$-$C_6$ alkyl), or hydroxy($C_1$-$C_6$ alkyl); and $R_4$ is H, $C_1$-$C_6$ alkyl, —C(O)($C_1$-$C_{20}$ alkyl), or —($CH_2$)$_{1-5}$—C(O)OH.

In another embodiment the GPBP-1 inhibitor is a compound having the formula:

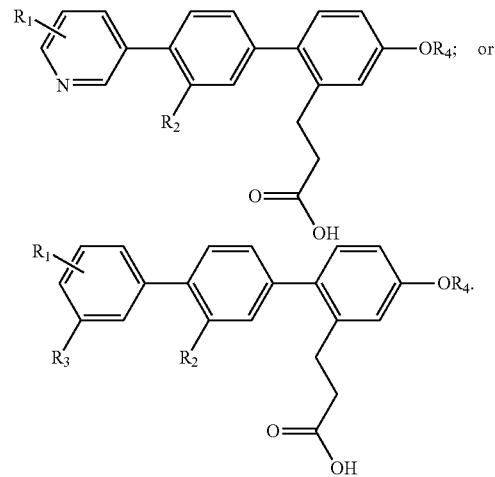

In various embodiments of any embodiment of the compounds of formulae (B) and (C), $R_2$ may be $C_1$-$C_6$ alkyl, halo($C_1$-$C_6$ alkyl), or hydroxy($C_1$-$C_6$ alkyl). For example, $R_2$ may be $C_1$-$C_6$ alkyl, methyl, halo($C_1$-$C_6$ alkyl), fluoromethyl, difluoromethyl, hydroxymethyl, or hydroxy($C_1$-$C_6$ alkyl).

In various further embodiments of any embodiment of the compounds of formulae (B) and (C), $R_4$ may be H, $C_1$-$C_6$ alkyl, methyl, propyl, —C(O)($C_1$-$C_{20}$ alkyl), or —($CH_2$)$_{1-5}$—C(O)OH.

In various further embodiments of any embodiment of the compounds of formulae (B) and (C), $R_1$ may be hydrogen or methoxy.

In various further embodiments of any embodiment of the compounds of formulae (B) and (C), $R_3$ may be halogen, $C_1$-$C_6$ alkyl, halo($C_1$-$C_6$ alkyl), $C_1$-$C_6$ alkoxy, halo($C_1$-$C_6$ alkoxy), chloro, methyl, or trifluoromethyl. In various further embodiments of any embodiment of the compounds of formulae (B) and (C), $R_3$ may be $C_1$-$C_6$ alkyl, halo($C_1$-$C_6$ alkyl), $C_1$-$C_6$ alkoxy, halo($C_1$-$C_6$ alkoxy), methyl, or trifluoromethyl.

In a further embodiment of the compounds of formulae (B) and (C), $R_1$ is hydrogen or $C_1$-$C_6$ alkoxy; $R_2$ is hydroxy($C_1$-$C_6$ alkyl); $R_3$, if present, is halogen, $C_1$-$C_6$ alkyl or halo($C_1$-$C_6$ alkyl); and $R_4$ is H or $C_1$-$C_6$ alkyl. In a further embodiment of the compounds of formulae (B) and (C), $R_1$ is hydrogen or $C_1$-$C_6$ alkoxy; $R_2$ is hydroxy($C_1$-$C_6$ alkyl); $R_3$, if present, is $C_1$-$C_6$ alkyl or halo($C_1$-$C_6$ alkyl); and $R_4$ is H or $C_1$-$C_6$ alkyl.

In another embodiment of the compounds of formulae (B) and (C), $R_1$ is hydrogen or methoxy; $R_2$ is hydroxymethyl; $R_3$, if present, is chloro, methyl or trifluoromethyl; and $R_4$ is H or methyl. In another embodiment of the compounds of formulae (B) and (C), $R_1$ is hydrogen or methoxy; $R_2$ is hydroxymethyl; $R_3$, if present, is methyl or trifluoromethyl; and $R_4$ is H or methyl.

In another embodiment the GPBP-1 inhibitor is a compound of formula (D):

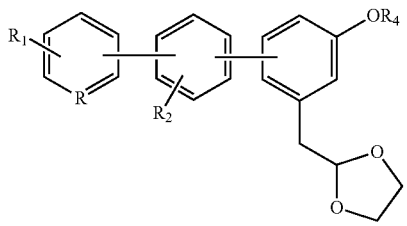

or a pharmaceutically acceptable salt thereof, wherein:
R is selected from N and $CR_3$;
$R_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo ($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O) ($C_1$-$C_6$ alkoxy), —($CH_2$)$_{1-5}$—C(O)$NH_2$, (aryl)$C_2$-$C_6$ alkyl, and (heteroaryl)$C_1$-$C_6$ alkyl;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl ($C_1$-$C_6$ alkyl), ($C_1$-$C_6$ alkyl)sulfanyl($C_1$-$C_6$ alkyl), —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, —($CH_2$)$_{1-5}$—C(O)NH ($C_1$-$C_6$ alkyl), —($CH_2$)$_{1-5}$—C(O)N($C_1$-$C_6$ alkyl)$_2$, —CH=CH—C(O)OH, or —CH=CH—C(O)($C_1$-$C_6$ alkoxy); and $R_4$ is hydrogen, $C_1$-$C_6$ alkyl, or (aryl)$C_1$-$C_6$ alkyl.

In one embodiment, the compound of formula (D) is of the formula:

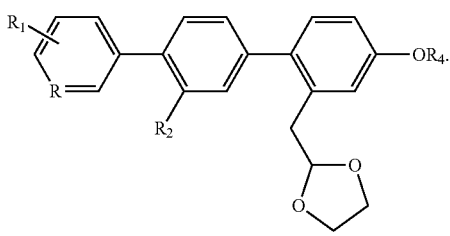

In one embodiment of any embodiment of the compound of formula (D), $R_1$ is hydrogen. In another embodiment of any embodiment of the compound of formula (D) R is $CR_3$, and $R_3$ is formyl($C_1$-$C_6$ alkyl). In another embodiment, $R_3$ is —COH. In various embodiments, $R_2$ may be —CH=CH—C(O)OH; —CH=CH—C(O)($C_1$-$C_6$ alkoxy); or —CH=CH—C(O)(OEt). In various further embodiments, $R_4$ may be (aryl)$C_1$-$C_6$ alkyl; or —$CH_2$-Ph. In a preferred embodiment, the compound of formula D is a compound is of the formula:

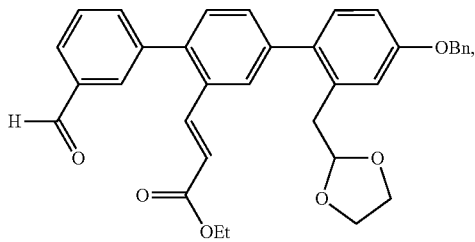 [SMILES: CCOC(=O)/C=C/c1cc(-c2ccc(OCc3ccccc3)cc2CC2OCCO2)ccc1-c1cccc(C=O)c1]

or a pharmaceutically acceptable salt thereof.

In another embodiment, the GPBP1—inhibitors comprise compounds of formula (I):

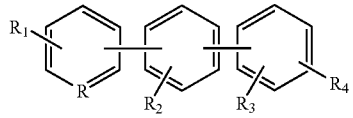

or a pharmaceutically acceptable salt thereof, wherein:
R is selected from N and $CR_5$;
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)($C_1$-$C_6$ alkoxy), —$(CH_2)_{1-5}$—C(O)$NH_2$, (aryl)$C_2$-$C_6$ alkyl, and (heteroaryl)$C_1$-$C_6$ alkyl;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, (aryl)$C_1$-$C_6$ alkyl, or (heteroaryl)$C_1$-$C_6$ alkyl;
$R_3$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), (aryl)$C_1$-$C_6$ alkyl, or (heteroaryl)$C_1$-$C_6$ alkyl; and
$R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O$(CH_2)_{1-5}$—C(O)OH, —O$(CH_2)_{1-5}$—C(O)($C_1$-$C_6$ alkoxy), (aryl)$C_1$-$C_6$ alkyl, or (heteroaryl)$C_1$-$C_6$ alkyl.

In another embodiment, the GPBP-1 inhibitors are compounds of formula (II):

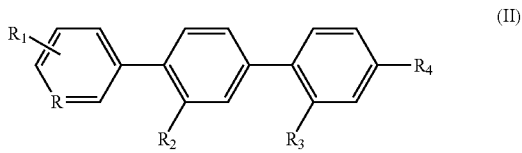

In another embodiment, the GPBP-1 inhibitors are compounds of formulae (I) or (II) wherein:
R is selected from N and $CR_5$;
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)($C_1$-$C_6$ alkoxy), and —$(CH_2)_{1-5}$—C(O)$NH_2$;
$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), or —$(CH_2)_{1-5}$—C(O)$NH_2$;
$R_3$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, or —CH=CH—C(O)($C_1$-$C_6$ alkoxy); and
$R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O$(CH_2)_{1-5}$—C(O)OH, or —O$(CH_2)_{1-5}$—C(O)($C_1$-$C_6$ alkoxy).

In another embodiment, the GPBP-1 inhibitors are compounds of formulae (I) or (II) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)sulfanyl($C_1$-$C_6$ alkyl);

$R_3$ is $C_1$-$C_6$ alkyl, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, or —CH=CH—C(O)($C_1$-$C_6$ alkoxy); and $R_4$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, —CH=CH—C(O)($C_1$-$C_6$ alkoxy), —O$(CH_2)_{1-5}$—C(O)OH, or —O$(CH_2)_{1-5}$—C(O)($C_1$-$C_6$ alkoxy).

In another embodiment, the GPBP-1 inhibitors are compounds of formula (II), wherein R is N. These compounds can be represented by formula (III):

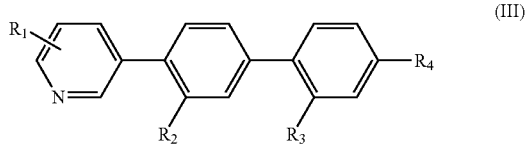

(III)

In yet another embodiment, the GPBP-1 inhibitors are compounds of formula (II), wherein R is $CR_5$. These compounds can be represented by formula (IV):

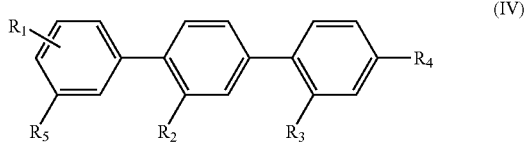

(IV)

In one embodiment, the GPBP-1 inhibitors are compounds as described above with reference to any of formulae (I)-(IV), wherein $R_1$ is hydrogen, hydroxy, or $C_1$-$C_6$ alkoxy. In one embodiment, the GPBP-1 inhibitors are compounds as described above with reference to any of formulae (I)-(IV), wherein $R_1$ is hydrogen. In another embodiment, the GPBP-1 inhibitors are compounds as described above with reference to any of formulae (I)-(IV), wherein $R_2$ is $C_1$-$C_6$ alkyl, halo($C_1$-$C_6$ alkyl), hydroxy($C_1$-$C_6$ alkyl), formyl($C_0$-$C_6$ alkyl), amino($C_1$-$C_6$ alkyl), or sulfanyl($C_1$-$C_6$ alkyl). In yet another embodiment, the GPBP-1 inhibitors are compounds as described above with reference to any of formulae (I)-(IV), wherein $R_2$ is $C_1$-$C_6$ alkyl, halo($C_1$-$C_6$ alkyl), hydroxy($C_1$-$C_6$ alkyl), or formyl($C_0$-$C_6$ alkyl).

In yet another embodiment, the GPBP-1 inhibitors are compounds as described above with reference to any of formulae (I)-(IV), wherein $R_2$ can be $C_1$-$C_6$ alkyl, halo($C_1$-$C_6$ alkyl), or hydroxy($C_1$-$C_6$ alkyl). For example, in certain embodiments $R_2$ can be $C_1$-$C_6$ alkyl such as methyl, ethyl, or isopropyl. In other embodiments, $R_2$ can be halo($C_1$-$C_6$ alkyl) such as fluoromethyl, difluoromethyl, or trifluoromethyl. $R_2$ can, in certain embodiments, be hydroxy($C_1$-$C_6$ alkyl). For example, the hydroxy($C_1$-$C_6$ alkyl) can be hydroxymethyl, 1-hydroxyethyl, or 2-hydroxyethyl.

In another embodiment, the GPBP-1 inhibitors are compounds as described above with reference to any of formulae (I)-(IV), wherein $R_2$ is $C_1$-$C_6$ alkyl. In certain embodiments $R_2$ is methyl. In another embodiment, the GPBP-1 inhibitors are compounds as described above with reference to any of formulae (I)-(IV), wherein $R_3$ is $C_1$-$C_6$ alkyl, —$(CH_2)_{1-5}$—C(O)OH, —$(CH_2)_{1-5}$—C(O)($C_1$-$C_6$ alkoxy), —CH=CH—C(O)OH, or —CH=CH—C(O)($C_1$-$C_6$ alkoxy). In another embodiment, the GPBP-1 inhibitors are compounds as described above with reference to any of formulae (I)-(IV), wherein $R_3$ is —$(CH_2)_{1-5}$—C(O)OH, —$(CH_2)_{1-5}$—C(O)($C_1$-$C_6$ alkoxy), or —$(CH_2)_{1-5}$—C(O)$NH_2$.

In yet another embodiment, the GPBP-1 inhibitors are compounds as described above with reference to any of formulae (I)-(IV), wherein $R_3$ is —$(CH_2)_{1-2}$—C(O)OH, or —$(CH_2)_{1-2}$—C(O)($C_1$-$C_6$ alkoxy). For example, in certain embodiments $R_3$ can be —$(CH_2)_2$—C(O)OH, —$(CH_2)_2$—C(O)(OCH$_3$), —$(CH_2)_2$—C(O)(OCH$_2$CH$_3$), or —$(CH_2)_2$—C(O)(OC(CH$_3$)$_3$). In other embodiments, $R_3$ can be —$(CH_2)_2$—C(O)OH, or —$(CH_2)_2$—C(O)(OCH$_2$CH$_3$).

In another embodiment, the GPBP-1 inhibitors are compounds as described above with reference to any of formulae (I)-(IV), wherein $R_3$ is —$(CH_2)_{1-2}$—C(O)OH. In one embodiment, $R_3$ is —$(CH_2)_2$—C(O)OH. In one embodiment, the GPBP-1 inhibitors are compounds as described above with reference to any of formulae (I)-(IV), wherein $R_4$ is hydroxy, halogen, $C_1$-$C_6$ alkyl, $C_1$-$C_6$ alkoxy, halo($C_1$-$C_6$ alkoxy), or benzyloxy. In another embodiment, the GPBP-1 inhibitors are compounds as described above with reference to any of formulae (I)-(IV), wherein $R_4$ is hydroxy or $C_1$-$C_6$ alkoxy (e.g., methoxy). Preferably $R_4$ is $C_1$-$C_6$ alkoxy. In more preferred embodiment, $R_4$ is methoxy.

In one embodiment, the GPBP-1 inhibitors are compounds as described above with reference to formulae (I), (II), or (IV), wherein $R_5$ is $C_1$-$C_6$ alkyl, halo($C_1$-$C_6$ alkyl), $C_1$-$C_6$ alkoxy, or halo($C_1$-$C_6$ alkoxy). In another embodiment, the GPBP-1 inhibitors are compounds as described above with reference to formulae (I), (II), or (IV), wherein $R_5$ is $C_1$-$C_6$ alkyl, such as methyl. In yet another embodiment, the GPBP-1 inhibitors are compounds as described above with reference to formulae (I), (II), or (IV), wherein $R_5$ is halo($C_1$-$C_6$ alkyl), such as trifluoromethyl.

In certain embodiments, the GPBP-1 inhibitors are compounds of any of formulae (I), (II), or (IV), wherein:

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)thio($C_1$-$C_6$ alkyl);

$R_3$ is —$(CH_2)_{1-2}$—C(O)OH, —$(CH_2)_{1-2}$—C(O)($C_1$-$C_6$ alkoxy), —$(CH_2)_{1-2}$—C(O)$NH_2$, —$(CH_2)_{1-2}$—C(O)NH($C_1$-$C_6$ alkyl), —$(CH_2)_{1-2}$—C(O)N($C_1$-$C_6$ alkyl)$_2$, —CH=CH—C(O)OH, —CH=CH—C(O)($C_1$-$C_6$ alkoxy); and $R_4$ is hydroxy, $C_1$-$C_6$ alkoxy, halo($C_1$-$C_6$ alkoxy), or benzyloxy.

In certain embodiments, the GPBP-1 inhibitors are compounds of any of formula (III), wherein:

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)thio($C_1$-$C_6$ alkyl);

$R_3$ is —$(CH_2)_{1-2}$—C(O)OH, —$(CH_2)_{1-2}$—C(O)($C_1$-$C_6$ alkoxy), —$(CH_2)_{1-2}$—C(O)NH$_2$, —$(CH_2)_{1-2}$—C(O)NH($C_1$-$C_6$ alkyl), —$(CH_2)_{1-2}$—C(O)N($C_1$-$C_6$ alkyl)$_2$, —CH═CH—C(O)OH, —CH═CH—C(O)($C_1$-$C_6$ alkoxy); and $R_4$ is hydroxy, $C_1$-$C_6$ alkoxy, halo($C_1$-$C_6$ alkoxy), or benzyloxy.

In certain embodiments, the GPBP-1 inhibitors are compounds of any of formulae (I), (II), or (IV), wherein $R_1$ is hydrogen; $R_2$ is $C_1$-$C_6$ alkyl, halo($C_1$-$C_6$ alkyl), hydroxy($C_1$-$C_6$ alkyl), or formyl($C_1$-$C_6$ alkyl); $R_3$ is —$(CH_2)_{1-2}$—C(O)OH, —$(CH_2)_{1-2}$—C(O)($C_1$-$C_6$ alkoxy), or —$(CH_2)_{1-2}$—C(O)NH$_2$; $R_4$ is hydroxy or $C_1$-$C_6$ alkoxy; and $R_5$ is $C_1$-$C_6$ alkyl, halo($C_1$-$C_6$ alkyl), $C_1$-$C_6$ alkoxy, or halo($C_1$-$C_6$ alkoxy).

In certain embodiments, the GPBP-1 inhibitors are compounds of any of formula (III), wherein $R_1$ is hydrogen; $R_2$ is $C_1$-$C_6$ alkyl, halo($C_1$-$C_6$ alkyl), hydroxy($C_1$-$C_6$ alkyl), or formyl($C_1$-$C_6$ alkyl); $R_3$ is —$(CH_2)_{1-2}$—C(O)OH, —$(CH_2)_{1-2}$—C(O)($C_1$-$C_6$ alkoxy), or —$(CH_2)_{1-2}$—C(O)NH$_2$; $R_4$ is hydroxy or $C_1$-$C_6$ alkoxy; and $R_5$ is $C_1$-$C_6$ alkyl, halo($C_1$-$C_6$ alkyl), $C_1$-$C_6$ alkoxy, or halo($C_1$-$C_6$ alkoxy).

In certain embodiments, the GPBP-1 inhibitors are compounds of any of formulae (I)-(IV), wherein:

R, if present, is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen;

$R_2$ is $C_1$-$C_6$ alkyl;

$R_3$ is —$(CH_2)_{1-2}$—C(O)OH; and $R_4$ is $C_1$-$C_6$ alkoxy.

In certain embodiments, the GPBP-1 inhibitors are compounds of any of formulae (I)-(IV), wherein:

R, if present, is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen;

$R_2$ is methyl;

$R_3$ is —$(CH_2)_2$—C(O)OH; and $R_4$ is methoxy.

In one embodiment, the compounds of formula (V) are of formula (VI):

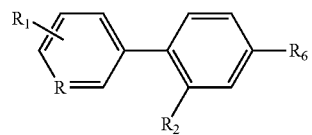

(VI)

In another embodiment, the GPBP-1 inhibitors are compounds of formulae (V) or (VI) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), and —$(CH_2)_{1-5}$—C(O)NH$_2$;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)NH$_2$, —CH═CH—C(O)OH, or —CH═CH—C(O)($C_1$-$C_6$ alkoxy); and $R_6$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)NH$_2$, —$(CH_2)_{1-5}$—C(O)NH($C_1$-$C_6$ alkyl), —$(CH_2)_{1-5}$—C(O)N($C_1$-$C_6$ alkyl)$_2$, —CH═CH—C(O)OH, —CH═CH—C(O)($C_1$-$C_6$ alkoxy), or —OS(O)$_2$CF$_3$.

In another embodiment, the GPBP-1 inhibitors are compounds of formulae (V) or (VI) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —CH═CH—C(O)OH, or —CH═CH—C(O)($C_1$-$C_6$ alkoxy); and $R_6$ is hydroxy, halogen, $C_1$-$C_6$ alkyl, $C_1$-$C_6$ alkoxy, halo($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)NH$_2$, —$(CH_2)_{1-5}$—C(O)NH($C_1$-$C_6$ alkyl), —$(CH_2)_{1-5}$—C(O)N($C_1$-$C_6$ alkyl)$_2$, —CH═CH—C(O)OH, —CH═CH—C(O)($C_1$-$C_6$ alkoxy), or —OS(O)$_2$CF$_3$.

In one embodiment, the GPBP-1 inhibitors are compounds as described above with reference to any of formulae (V)-(VI), wherein $R_1$ is hydrogen.

In another embodiment, the GPBP-1 inhibitors are compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), amino($C_1$-$C_6$ alkyl), sulfanyl($C_1$-$C_6$ alkyl), —CH═CH—C(O)OH, or —CH═CH—C(O)($C_1$-$C_6$ alkoxy).

In yet another embodiment, the GPBP-1 inhibitors are compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), —CH═CH—C(O)OH, or —CH═CH—C(O)($C_1$-$C_6$ alkoxy).

In yet another embodiment, the GPBP-1 inhibitors are compounds as described above with reference to any of formulae (V)-(VI), wherein $R_2$ can be $C_1$-$C_6$ alkyl, halo($C_1$-$C_6$ alkyl), hydroxy($C_1$-$C_6$ alkyl), or —CH═CH—C(O)($C_1$-$C_6$ alkoxy). For example, in certain embodiments $R_2$ can be $C_1$-$C_6$ alkyl such as methyl, ethyl, or isopropyl. In other embodiments, $R_2$ can be halo($C_1$-$C_6$ alkyl) such as fluoromethyl, difluoromethyl, or trifluoromethyl. $R_2$ can, in certain embodiments, be hydroxy($C_1$-$C_6$ alkyl). For example, the hydroxy($C_1$-$C_6$ alkyl) can be hydroxymethyl, 1-hydroxyethyl, or 2-hydroxyethyl.

In another embodiment, the GPBP-1 inhibitors are compounds as described above with reference to any of formulae (V)-(VI), wherein $R_2$ is $C_1$-$C_6$ alkyl. In certain embodiments $R_2$ is methyl.

In one embodiment, the GPBP-1 inhibitors are compounds as described above with reference to any of formulae (V)-(VI), wherein $R_6$ is hydroxy, halogen, $C_1$-$C_6$ alkyl, $C_1$-$C_6$ alkoxy, halo($C_1$-$C_6$ alkoxy), benzyloxy, or —OS(O)$_2$CF$_3$.

In another embodiment, the GPBP-1 inhibitors are compounds as described above with reference to any of formulae (V)-(VI), wherein $R_6$ is hydroxy or $C_1$-$C_6$ alkoxy (e.g., methoxy). In one embodiment, the GPBP-1 inhibitors are compounds as described above with reference to formulae (V)-(VI), wherein $R_5$ is $C_1$-$C_6$ alkyl, halo($C_1$-$C_6$ alkyl), $C_1$-$C_6$ alkoxy, or halo($C_1$-$C_6$ alkoxy). In another embodiment, the GPBP-1 inhibitors are compounds as described above with reference to formulae (V)-(VI), wherein $R_5$ is $C_1$-$C_6$ alkyl, such as methyl. In yet another embodiment, the GPBP-1 inhibitors are compounds as described above with reference to formulae (V)-(VI), wherein $R_5$ is halo($C_1$-$C_6$ alkyl), such as trifluoromethyl.

In certain embodiments, the GPBP-1 inhibitors are compounds of any of formulae (V)-(VI), wherein:

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino ($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)thio ($C_1$-$C_6$ alkyl), or —CH═CH—C(O)($C_1$-$C_6$ alkoxy); and $R_6$ is hydroxy, $C_1$-$C_6$ alkoxy, halo($C_1$-$C_6$ alkoxy), or —OS(O)$_2$CF$_3$.

In certain embodiments, the GPBP-1 inhibitors are compounds of any of formulae (V)-(VI), wherein $R_1$ is hydrogen; $R_2$ is $C_1$-$C_6$ alkyl, halo($C_1$-$C_6$ alkyl), hydroxy($C_1$-$C_6$ alkyl), formyl($C_0$-$C_6$ alkyl), or —CH═CH—C(O)($C_1$-$C_6$ alkoxy); $R_6$ is hydroxy, $C_1$-$C_6$ alkoxy, or —OS(O)$_2$CF$_3$; and $R_5$ is $C_1$-$C_6$ alkyl, halo($C_1$-$C_6$ alkyl), $C_1$-$C_6$ alkoxy, or halo($C_1$-$C_6$ alkoxy).

In various further embodiments, the GPBP-1 inhibitor comprises one or more inhibitors selected from the group consisting of:

(a) an antibody or aptamer selective for GPBP-1;

(c) an inhibitory nucleic acid selective for GPBP mRNA;

(d) a peptide comprising an amino acid sequence of general formula X1-SHCIX2-X3 (SEQ ID NO: 1)

wherein X1 is 0-10 amino acids of the sequence ATTAGILATL (SEQ ID NO: 2);

X2 is E or Q; and

X2 is 0-10 amino acids of the sequence LMVKREDSWQ (SEQ ID NO: 3);

(g) a peptide comprising an amino acid sequence selected from the group consisting of SHCIE (SEQ ID NO: 4), SHCIQ (SEQ ID NO: 5), ILATLSHCIELMVKR (SEQ ID NO: 6), ILATLSHClQLMVKR (SEQ ID NO: 7), and LATLSHCIELMVKR (SEQ ID NO: 8); and (h) 1-20:
RDEVIGILKAEKMDLALLEAQYGFVTP-KKVLEALQRDAFQAKSTPWQEDI YEKPMNELD-KVVEKHKESYRRILGQLLVAEK-SHRQTILELEEEKRKHKEYMEKSD EFICLLEQECERLKKLIDQEIK-SQEEKEQEKEKRVTTLKEELTKLKSFALMVVDEQ QRLTAQLTLQRQKIQELTTNAKETHT-KLALAEARVQEEEQKATRLEKELQTQTTK FHQDQDTIMAKLTNEDSQNRQLQQK-LAALSRQIDELEETNRSLRKAEEE (SEQ ID NO: 9).

Sequences of the polypeptides recited in the above are known in the art; see, for example, U.S. Pat. Nos. 7,326,768; 7,935,492; 6,579,969; and 7,147,855.

Synthesis of the other GPBP-1 inhibitors disclosed herein can be carried out by those of skill in the art, based on the teachings in WO2011/054530.

While the examples that follow focus on doxorubicin as an exemplary anti-tumor agent which inhibits GPBP-1 kinase activity, any suitable anti-tumor agent can be used since all tumors possess populations of CSC and GPBP-1 inhibitors of the invention reduce CSC viability. Thus, combining the GPBP-1 inhibitors of the invention with any anti-tumor agent is likely to provide an improved therapeutic product.

Thus, any suitable anti-tumor drug can be used in the pharmaceutical compositions of the present invention, including but not limited to anthracyclines, alkylating agents (e.g., mitomycin C), alkyl sulfonates, aziridines, ethylenimines, methylmelarmines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Particular examples of known chemotherapeutic agents to which the cancer may have developed resistance include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, cannustine, chlorozotocin, fotemustine, lomustine, nimustine, ranimustine, dacarbazine, mannomiustine, mnitobronitoi, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfomithine, elliptinium acetate, etoglucid, etoposide, flutamide, gallium nitrate, hydroxyurea, interferon-alpha, interferon-beta, interferon-gamma, interleukin-2, lentinan, lonidamine, prednisone, dexamethasone, leucovorin, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2''-trichlorotriethylamine, urethane, vinblastine, vincristine, and vindesine.

In a preferred embodiment, the antitumor drug is selected from the group consisting of paclitaxel, a topoisomerase II inhibitor, 5-fluorouracil (5-FU), and cisplatin. In a preferred embodiment, the antitumor drug is a topoisomerase II inhibitor. In another preferred embodiment, the topisomerase II inhibitor comprises an anthracyclin or podophyllotoxin derivative. In a most preferred embodiment, the anthracyclin drug is doxorubicin and the podophyllotoxin derivative is etoposide.

The inventors have further discovered that GPBP-1 inhibitor synergism with anti-tumor agents may in some cases be reduced by p21, a cyclin-dependent kinase inhibitor that promotes cell cycle arrest in response to DNA damage. Thus, in another embodiment of any of the compositions of the invention, the composition may further comprise a p21 inhibitor. Any suitable p21 inhibitor can be used, including but not limited to p21 antibodies, p21 siRNA, p21 shRNA, and p21 antisense compounds.

As disclosed herein, the inventors have discovered that the ATP-binding cassette transporter 7 (ABCC7) is synergistic with T12 reducing viability of tumor cells raising the possibility that this ABC member may act as a xenobiotic transporter to mediate exclusion of GPBP-inhibitors of the invention at the CSC compartments. Thus, inhibitors of ABCC7 expression and/or activity can be used for reducing chemoresistance of a tumor. Thus, in another embodiment of any of the compositions of the invention, the composition may further comprise an inhibitor of ATP-binding cassette transporter 7 (ABCC7). Any suitable ABCC7 inhibitor may be used, including but not limited to ABCC7 antibodies, ABCC7 siRNA, ABCC7 shRNA, ABCC7 antisense compounds and ABCC7 expression inhibitors including but not limited to 3-[(3-Trifluoromethyl)phenyl]-5-[(4-carboxyphenyl)methylene]-2-thioxo-4-thiazolidinone (172, Calbiochem, EMD Millipore), 7,9-Dimethyl-11-phenyl-6-(5-methylfuran-2-yl)-5,6-dihydro-pyrimido-[4',5'-3,4]pyrrolo[1,2-a]quinoxaline-8,10-(7H,9H)-dione (PPQ-102, Calbiochem, EMD Millipore), 1-[(2,4-Dichlorophenyl)methyl]-1H-indazole-3-carboxylic acid (Lonidamine, Tocris Bioscience), trans-N-[6-Cyano-3,4-dihydro-3-hydroxy-2,2-dimethyl-2H-1-benzopyran-4-yl]-N-methyl-ethanesulfonamide (Chromanol 293B, Tocris Bioscience), 1-[[p-[2-(5-chloro-o-anisamido)ethyl]phenyl]sulfonyl]-3-cyclo-hexylurea (Glibenclamide, Santa Cruz Biotechnology), and N-(2-Naphthalenyl)-((3,5-dibromo-2,4-dihydroxyphenyl)methylene)glycine hydrazide (GlyH-101, Calbiochem, EMD Millipore), or pharmaceutically acceptable salts thereof.

The compounds in the pharmaceutical composition include pharmaceutically acceptable salts, esters, amides, and prodrugs thereof, including but not limited to carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

Examples of pharmaceutically acceptable, non-toxic esters of the compounds of this invention include $C_1$-$C_6$ alkyl esters, wherein the alkyl group is a straight or branched, substituted or unsubstituted, $C_5$-$C_7$ cycloalkyl esters, as well as arylalkyl esters such as benzyl and triphenylmethyl. $C_1$-$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$-$C_6$ alkyl amines and secondary $C_1$-$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

In one embodiment, the disclosure provides pharmaceutical compositions comprising a compound as described above with reference to any one of formulae (I)-(VI) and at least one pharmaceutically acceptable carrier, solvent, adjuvant or diluent.

For administration, the compositions are ordinarily combined with one or more adjuvants appropriate for the indicated route of administration. The compositions may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compositions of this invention may be provided in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The compositions may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

The compositions of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. The compositions include one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The pharmaceutical compositions of the present invention may also be prepared in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Pharmaceutical compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

In a second aspect, the present invention provides methods for treating a tumor, comprising administering to a subject with a tumor an amount effective to treat the tumor of (i) an antitumor drug, and (ii) a compound of formula (A):

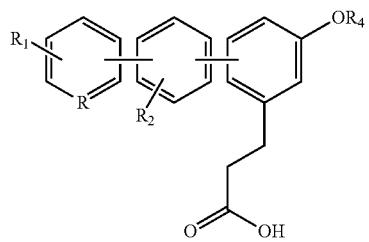

or a pharmaceutically acceptable salt thereof, wherein:

R is selected from N and $CR_3$; $R_1$ is hydrogen or $C_1$-$C_6$ alkoxy; $R_2$ is $C_1$-$C_6$ alkyl or halo($C_1$-$C_6$ alkyl); $R_3$, if present, is halogen, $C_1$-$C_6$ alkyl or halo($C_1$-$C_6$ alkyl); and $R_4$ is H or $C_1$-$C_6$ alkyl.

As discussed above, the inventors have discovered that the GPBP-1 inhibitors of the invention can act synergistically with anti-tumor agents to provide a more effective therapeutic option for treating tumors. While not being bound by a specific mechanism of action, the inventors believe that GPBP-1 inhibitors, such as those of general formula (A) and embodiments thereof, are synergistic with anti-tumor agents (exemplified by doxorubicin) in treating tumors because both compounds act to inhibit GPBP kinase in a different fashion, and because the GPBP-1 inhibitors reduce viability of CSC in the tumor. CSC are expected to be responsible for drug resistance because they are not likely to be killed by antimitotic drugs since they divide slowly and they have abundant xenobiotic transporters, among other characteristics.

In a preferred embodiment of the compound of formula (A), $R_1$ is hydrogen or methoxy; $R_2$ is methyl, fluoromethyl, or difluoromethyl; $R_3$, if present, is chloro, methyl or trifluoromethyl; and $R_4$ is H or methyl. In another preferred embodiment of the compound of formula (A), $R_1$ is hydrogen or methoxy; $R_2$ is methyl, fluoromethyl, or difluoromethyl; $R_3$, if present, is methyl or trifluoromethyl; and $R_4$ is H or methyl.

In various further preferred embodiments, $R_1$ is hydrogen and/or $R_4$ is methyl. In further preferred embodiments, the compound of formula (A) is selected from the group consisting of:

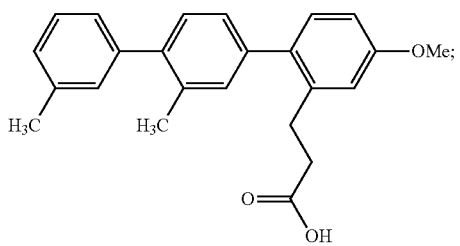

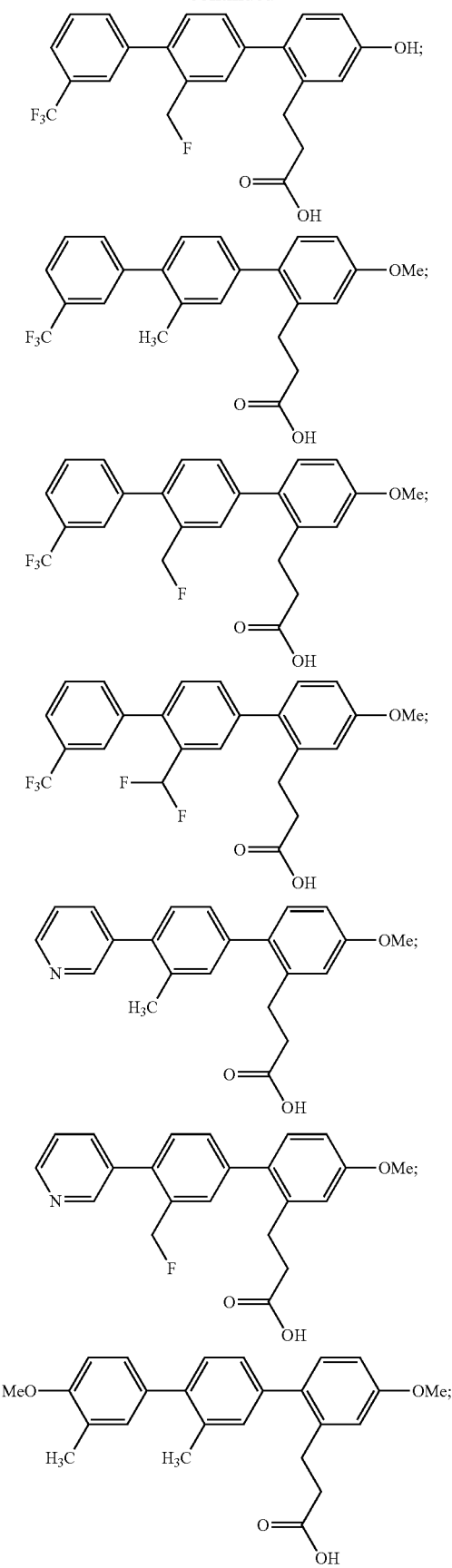

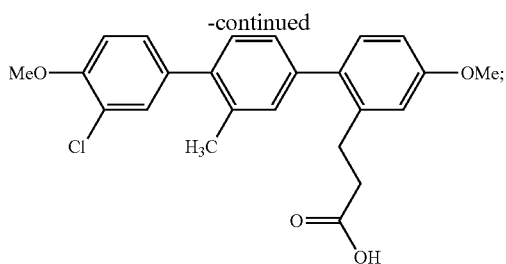

or a pharmaceutically acceptable salt thereof. In a most preferred embodiment, the compound is

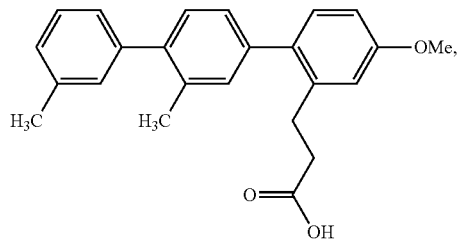

or a pharmaceutically acceptable salt thereof.

In another embodiment of this second aspect, the methods comprise administering to a subject with a tumor an amount effective to treat the tumor of (i) an antitumor drug, and (ii) a GPBP-1 inhibitor according to any embodiment or combination of embodiments disclosed herein, including any embodiment or combination of embodiments of the compounds of general formulae (B), (C), (D), and (I-VI).

Any suitable anti-tumor drug can be used in the methods of the invention, including but not limited to anthracyclines, alkylating agents (e.g., mitomycin C), alkyl sulfonates, aziridines, ethylenimines, methylmelarmines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Particular examples of known chemotherapeutic agents to which the cancer may have developed resistance include, but are not limited to, busulfan, improsulfan, pipo-sulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, cannustine, chlorozotocin, fotemustine, lomustine, nimustine, ranimustine, dacarbazine, mannomiustine, mnitobronitoi, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfomithine, elliptinium acetate, etoglucid, etoposide, flutamide, gallium nitrate, hydroxyurea, interferon-alpha, interferon-beta, interferon-gamma, interleukin-2, lentinan, lonidamine, prednisone, dexamethasone, leucovorin, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethane, vinblastine, vincristine, and vindesine.

In a preferred embodiment, the antitumor drug is selected from the group consisting of paclitaxel, a topoisomerase II inhibitor, 5-fluorouracil (5-FU), and cisplatin. In a preferred embodiment, the antitumor drug is a topoisomerase II inhibitor. In another preferred embodiment, the topisomerase II inhibitor comprises an anthracyclin or podophyllotoxin derivative. In a most preferred embodiment, the anthracyclin drug is doxorubicin and the podophyllotoxin derivative is etoposide.

While not being bound by a specific mechanism of action, the inventors believe that any tumor will benefit of the therapeutic effect of the GPBP-1 inhibitors and methods of the invention. In a preferred embodiment, the tumor shows significant expression of GPBP and/or increases GPBP expression in response to a chemotherapeutic agent. Thus, in a preferred embodiment, the tumor expresses GPBP (i.e.: a "GPBP expressing tumor"). Such "expression" can be any amount of increased expression relative to control cells (such as tumor reference cells known not to express GPBP). In a further preferred embodiment, the tumor overexpresses GPBP in response to chemotherapeutic agent. Such "overexpression" can be any amount of overexpression relative to control cells (such as tumor reference cells known not to overexpress GPBP in response to chemotherapeutic agent), for example, 5%, 10%, 15%, 20%, 25%, 50%, 75%, 100%, or greater. GPBP protein expression can be determined via any suitable technique. Methods for determining circulating GPBP levels are known in the art (See U.S. Pat. No. 7,935, 492).

In a further embodiment of any of these embodiments of the methods of the invention, the methods may further comprise administering to the subject an amount effective of a p21 inhibitor to inhibit p21 expression and/or activity in the tumor. Any suitable inhibitor of p21 can be used, including but not limited to compounds that downregulate p21 expression, p21 antibodies, p21 siRNA, p21 shRNA, and p21 antisense compounds. Any suitable inhibitor of p21 expression can be used, including but not limited to 2-(2-Chlorophenyl)-5,7-dihydroxy-8-[(3S,4R)-3-hydroxy-1-methylpiperidin-4-yl]-4H-chromen-4-one (Flavopiridol), (1R,2R,4S)-4-[(2R)-2-[(1R,9S,12S,15R,16E,18R,19R,21R,23S,24E,26E,28E, 30S,32S,35R)-1,18-dihydroxy-19,30-dimethoxy-15,17,21, 23,29,35-hexamethyl-2,3,10,14,20-pentaoxo-11,36-dioxa-4-azatricyclo[30.3.1.0^ {4,9}]hexatriaconta-16,24,26,28-tetraen-12-yl]propyl]-2-methoxycyclohexyl 3-hydroxy-2-(hydroxymethyl)-2-methylpropanoate (Temsirolimus), (3R, 4S,5S,6R,7R,9R,11S,12R,13S,14R)-6-{[(2S,3R,4S,6R)-4-(dimethylamino)-3-hydroxy-6-methyloxan-2-yl]oxy}-14-ethyl-7,12,13-trihydroxy-4-{[(2R,4R,5S,6S)-5-hydroxy-4-methoxy-4,6-dimethyloxan-2-yl]oxy}-3,5,7,9,11,13-hexamethyl-10-(2,4,7-trioxa-1-azaoctan-1-ylidene)-1-oxacyclotetradecan-2-one (Roxithromycin), 6-Hydroxy-2-(4-hydroxyphenyl)benzo[b]thien-3-yl][4-[2-(1-piperidinyl)ethoxy]phenyl]methanone hydrochloride (Raloxifene hydrochloride), (7S,9E,11S,12R,13S,14R,15R,16R,17S, 18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.$^{14,7}$.$0^{5,28}$]triaconta-1(28),2,4,9,19,21,25(29),26-octaen-13-yl acetate (Rifampicin), [(8R,9S,10R,13S,14S,17R)-17-acetyl-6,10,13-trimethyl-3-oxo-2,8,9,11,1214,15,16-octahydro-1H-cyclopenta[a]phenanthren-17-yl] acetate (Megestrol Acetate), 8-(4-Amino-1-methylbutylamino)-6-methoxyquinoline diphosphate salt (Primaquine diphosphate), Potassium; [2-butyl-5-chloro-3-[[4-[2-(1,2,3-triaza-4-azanidacyclopenta-2,5-dien-5-yl)phenyl]phenyl]methyl]imidazol-4-yl]methanol (Losartan potassium), (2S)-3-methyl-2-[pentanoyl-[[4-[2-(2H-tetrazol-5-yl)phenyl]phenyl]methyl]amino]butanoic acid (Valsartan), (Z)-but-2-enedioic acid; 2-(2,2-dicyclohexylethyl)piperidine (Perhexyline maleate), 3-O-methyl 5-O-(2-methylpropyl) 2,6-dimethyl-4-(2-nitrophenyl)-1,4-dihydropyridine-3,5-dicarboxylate (Nisoldipine), or pharmaceutically acceptable salts thereof. Such compounds are available from a number of commercial sources, such as Sigma-Aldrich, Santa Cruz Biotechnology, and Merck.

In a further embodiment of any of these embodiments of the methods of the invention, the methods may further comprise administering to the subject an amount effective of an inhibitor of ATP-binding cassette transporter 7 (ABCC7) to inhibit ABCC7 expression and/or activity in the tumor. Any suitable inhibitor of ABCC7 expression and/or activity can be used, including but not limited to ABCC7 antibodies, ABCC7 siRNA, ABCC7 shRNA, ABCC7 antisense compounds and ABCC7 expression inhibitors including but not limited to 3-[(3-Trifluoromethyl)phenyl]-5-[(4-carboxyphenyl)methylene]-2-thioxo-4-thiazolidinone (172), 7,9-Dimethyl-11-phenyl-6-(5-methylfuran-2-yl)-5,6-dihydro-pyrimido-[4',5'-3,4]pyrrolo[1,2-a]quinoxaline-8,10-(7H,9H)-dione (PPQ-102), 1[(2,4-Dichlorophenyl)methyl]-1H-indazole-3-carboxylic acid (Lonidamine), trans-N-[6-Cyano-3,4-dihydro-3-hydroxy-2,2-dimethyl-2H-1-benzopyran-4-yl]-N-methyl-ethanesulfonamide (Chromanol 293B), 1-[[p-[2-(5-chloro-o-anisamido)ethyl]phenyl]sulfonyl]-3-cyclohexylurea (Glibenclamide), and N-(2-Naphthalenyl)-((3,5-dibromo-2,4-dihydroxyphenyl)methylene)glycine hydrazide (GlyH-10), or pharmaceutically acceptable salts thereof.

In a further embodiment of the methods of the invention, the methods may comprise treating the subject with a pharmaceutical composition according to any embodiment or combination of embodiments of the invention.

As used herein, "treat" or "treating" means accomplishing one or more of the following: (a) reducing tumor size; (b) reducing tumor growth; (c) reducing or limiting development and/or spreading of metastases; (d) reducing the amount of antitumor drug required to maintain therapeutic objective for subject receiving treatment; and (e) depleting CSC in the tumor.

Thus, in one embodiment, treating the tumor comprises depleting CSC in the tumor. The inventors have discovered that the GPBP-1 inhibitors can reduce viability of CSC in tumors. CSC are expected to be responsible for drug resistance because they are not likely to be killed by antimitotic drugs since they divide slowly and they have abundant xenobiotic transporters, among other characteristics.

In another embodiment, treating the tumor comprises reducing tumor metastasis. "Inhibiting" tumor cell metastasis may comprise any amount of inhibition compared to no treatment. In various non-limiting embodiments, the methods may comprise inhibiting tumor cell metastasis, by 5%, 10%, 25%, 50%; 100%, or more compared to control (such as no treatment).

The different active compounds can be formulated as separate compositions that are given at the same time or different times, or the therapeutic agents can be given as a single composition, such as in the pharmaceutical compositions of the invention.

Appropriate dosage levels of the anti-tumor drugs and compounds can be determined by those of skill in the art in light of the teachings herein as well as other clinical factors. Exemplary dosage levels of the order of from about 0.01 mg to about 50 mg per kilogram of body weight per day, and more preferably between 0.1 mg to about 50 mg per kilogram of body weight per day, are generally useful in the treatment of the above-indicated conditions. The amount of active ingredient that may be combined with the carrier materials to produce a single dosage form will vary depending upon the subject treated and the particular mode of administration. Dosage unit forms will generally contain between from about 1 mg to about 500 mg of an active ingredient.

Compounds or pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the invention. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

The methods may be used to treat a subject with any suitable tumor, including but not limited to lung adenocarcinoma, lung epidermoid carcinoma, cervical carcinoma, colon carcinoma, and breast adenocarcinoma. In a preferred embodiment, the tumors are not chemoresistant tumors. In a further preferred embodiment, the tumor expresses significant amount of GPBP and/or increase GPBP expression in response to a chemotherapeutic agent. Thus, in a preferred embodiment, the tumor expresses GPBP (i.e.: a "GPBP expressing tumor"). Such "expression" can be any amount of increased expression relative to control cells (such as tumor reference cells known not to express GPBP). In a further preferred embodiment, the tumor overexpresses GPBP in response to chemotherapeutic agent. Such "overexpression" can be any amount of overexpression relative to control cells (such as tumor cells known not to overexpress GPBP in response to chemotherapeutic agent), for example, 5%, 10%, 15%, 20%, 25%, 50%, 75%, 100%, or greater.

In a third aspect, the present invention provides compounds of formula (D):

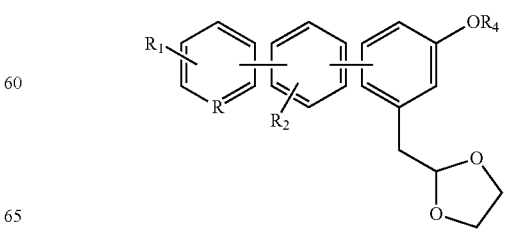

or a pharmaceutically acceptable salt thereof, wherein:
R is selected from N and $CR_3$;
  $R_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo ($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O) ($C_1$-$C_6$ alkoxy), —$(CH_2)_{1-5}$—$C(O)NH_2$, (aryl)$C_2$-$C_6$ alkyl, and (heteroaryl)$C_1$-$C_6$ alkyl;
  $R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);
  $R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl ($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—$C(O)NH_2$, —$(CH_2)_{1-5}$—C(O)NH ($C_1$-$C_6$ alkyl), —$(CH_2)_{1-5}$—C(O)N($C_1$-$C_6$ alkyl)$_2$, —CH=CH—C(O)OH, or —CH=CH—C(O)($C_1$-$C_6$ alkoxy); and
  $R_4$ is hydrogen, $C_1$-$C_6$ alkyl, or (aryl)$C_1$-$C_6$ alkyl.

Compounds according to this aspect of the invention can act synergistically with anti-tumor agents to provide a more effective therapeutic option for treating tumors, and thus can be used in the pharmaceutical compositions and methods of the invention, as disclosed herein In one embodiment, the compound of formula (D) is of the formula:

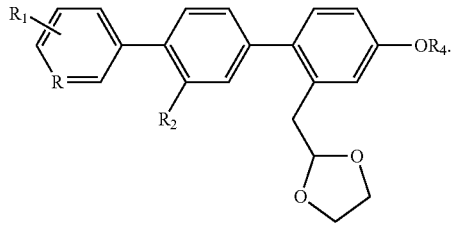

In one embodiment of any embodiment of the compound of formula (D), $R_1$ is hydrogen. In another embodiment of any embodiment of the compound of formula (D) R is $CR_3$, and $R_3$ is formyl($C_1$-$C_6$ alkyl). In another embodiment, $R_3$ is —COH. In various embodiments, $R_2$ may be —CH=CH—C(O)OH; —CH=CH—C(O)($C_1$-$C_6$ alkoxy); or —CH=CH—C(O)(OEt). In various further embodiments, $R_4$ may be (aryl)$C_1$-$C_6$ alkyl; or —$CH_2$-Ph. In a preferred embodiment, the compound of formula D is a compound is of the formula:

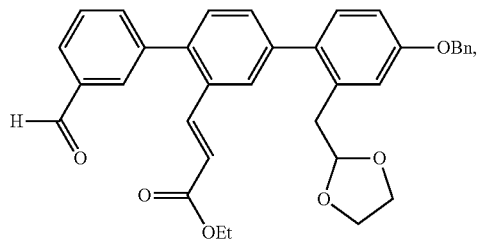

or a pharmaceutically acceptable salt thereof.

In a fourth aspect, the present invention provides methods for reducing chemoresistance of a tumor, comprising administering to a subject with a tumor that is to be treated with a chemotherapeutic an amount effective of an inhibitor of p21, or a pharmaceutically acceptable salt thereof, to inhibit p21 expression and/or activity in the tumor. As disclosed herein, the inventors have discovered that downregulation of p21 expression is synergistic with T12 and doxorubicin reducing viability of tumor cells. Thus, inhibitors of p21 expression and/or activity can be used for reducing chemoresistance of a tumor. Any suitable p21 inhibitor can be used in the method of the present invention, including but not limited to 2-(2-Chlorophenyl)-5,7-dihydroxy-8-[(3S,4R)-3-hydroxy-1-methylpiperidin-4-yl]-4H-chromen-4-one (Flavopiridol), (1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^{4,9}]hexatriaconta-16,24,26,28-tetraen-12-yl]propyl]-2-methoxycyclohexyl 3-hydroxy-2-(hydroxymethyl)-2-methylpropanoate (Temsirolimus), (3R,4S,5S,6R,7R,9R,11S,12R,13S,14R)-6-{[(2S,3R,4S,6R)-4-(dimethylamino)-3-hydroxy-6-methyloxan-2-yl]oxy}-[4-ethyl-7,12,13-trihydroxy-4-{[(2R,4R,5S,6S)-5-hydroxy-4-methoxy-4,6-dimethyloxan-2-yl]oxy}-3,5,7,9,11,13-hexamethyl-10-(2,4,7-trioxa-1-azaoctan-1-ylidene)-1-oxacyclotetradecan-2-one (Roxithromycin), 6-Hydroxy-2-(4-hydroxyphenyl)benzo[b]thien-3-yl][4-[2-(1-piperidinyl)ethoxy]phenyl]methanone hydrochloride (Raloxifene hydrochloride), (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.$1^{4,7}$.$0^{5,28}$]triaconta-1(28),2,4,9,19,21,25(29),26-octaen-13-yl acetate (Rifampicin), [(8R,9S,10R,13 S,14S,17R)-17-acetyl-6,10,13-trimethyl-3-oxo-2,8,9,11,1214,15,16-octahydro-1H-cyclopenta[a]phenanthren-17-yl]acetate (Megestrol Acetate), 8-(4-Amino-1-methylbutylamino)-6-methoxyquinoline diphosphate salt (Primaquine diphosphate), Potassium; [2-butyl-5-chloro-3-[[4-[2-(1,2,3-triaza-4-azanidacyclopenta-2,5-dien-5-yl)phenyl]phenyl]methyl]imidazol-4-yl] methanol (Losartan potassium), (2S)-3-methyl-2-[pentanoyl-[[4-[2-(2H-tetrazol-5-yl)phenyl]phenyl]methyl] amino]butanoic acid (Valsartan), (Z)-but-2-enedioic acid; 2-(2,2-dicyclohexylethyl)piperidine (Perhexyline maleate), 3-O-methyl 5-O-(2-methylpropyl) 2,6-dimethyl-4-(2-nitrophenyl)-1,4-dihydropyridine-3,5-dicarboxylate (Nisoldipine), or pharmaceutically acceptable salts thereof.

In a fifth aspect, the present invention provides methods for reducing chemoresistance of a tumor, comprising administering to a subject with a tumor that is to be treated with a chemotherapeutic an amount effective of an inhibitor of ATP-binding cassette transporter 7 (ABCC7), or a pharmaceutically acceptable salt thereof, to inhibit ABCC7 expression and/or activity in the tumor. As disclosed herein, the inventors have discovered that the ATP-binding cassette transporter 7 (ABCC7) is synergistic with T12 reducing viability of tumor cells raising the possibility that this ABC member may act as a xenobiotic transporter to mediate exclusion of GPBP-inhibitors of the invention at the CSC compartments. Thus, inhibitors of ABCC7 expression and/or activity can be used for reducing chemoresistance of a tumor. Any suitable ABCC7 inhibitor can be used in the method of the present invention, including but not limited to ABCC7 antibodies, ABCC7 siRNA, ABCC7 shRNA, ABCC7 antisense compounds and ABCC7 expression inhibitors including but not limited to 3-[(3-Trifluoromethyl)phenyl]-5-[(4-carboxyphenyl)methylene]-2-thioxo-4-thiazolidinone (172), 7,9-Dimethyl-11-phenyl-6-(5-methylfuran-2-yl)-5,6-dihydro-pyrimido-[4',5'-3,4]pyrrolo[1,2-a]quinoxaline-8,10-(7H,9H)-dione (PPQ-102), 1[(2,4-Dichlorophenyl)methyl]-1H-indazole-3-carboxylic acid (Lonidamine), trans-N-[6-Cyano-3,4-dihydro-3-hydroxy-2,2-dimethyl-2H-1-benzopyran-4-yl]-N-methyl-ethanesulfonamide (Chromanol 293B), 1-[[p-[2-(5-chloro-o-anisamido)ethyl]phenyl]sulfonyl]-3-cyclo-hexylurea (Glibenclamide), and N-(2-Naphthalenyl)-((3,5-dibromo-2,4-dihydroxyphenyl)methylene)glycine hydrazide (GlyH-10), or pharmaceutically acceptable salts thereof.

In a further aspect, the present invention provides methods for treating a tumor, comprising administering to a subject with a tumor an amount effective to treat the tumor of a compound of formula:

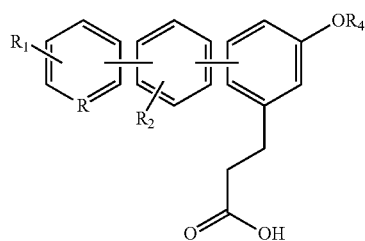

or a pharmaceutically acceptable salt thereof, wherein:
R is selected from N and $CR_3$;
$R_1$ is hydrogen or $C_1$-$C_6$ alkoxy;
$R_2$ is $C_1$-$C_6$ alkyl or halo($C_1$-$C_6$ alkyl);
$R_3$, if present, is halogen, $C_1$-$C_6$ alkyl or halo($C_1$-$C_6$ alkyl); and
$R_4$ is H or $C_1$-$C_6$ alkyl.

As shown in the examples that follow, certain compounds disclosed herein are effective to target CSC and thus to treat tumors in general, whether alone or in combination with other anti-tumor therapies.

In one embodiment, $R_1$ is hydrogen or methoxy; $R_2$ is methyl, fluoromethyl, or difluoromethyl; $R_3$, if present, is chloro, methyl or trifluoromethyl; and $R_4$ is H or methyl. In another embodiment, $R_1$ is hydrogen. In another embodiment, $R_1$ is hydrogen or methoxy; $R_2$ is methyl, fluoromethyl, or difluoromethyl; $R_3$, if present, is methyl or trifluoromethyl; and $R_4$ is H or methyl. In a further embodiment, $R_4$ is methyl. In a further embodiment, the compound is selected from the group consisting of

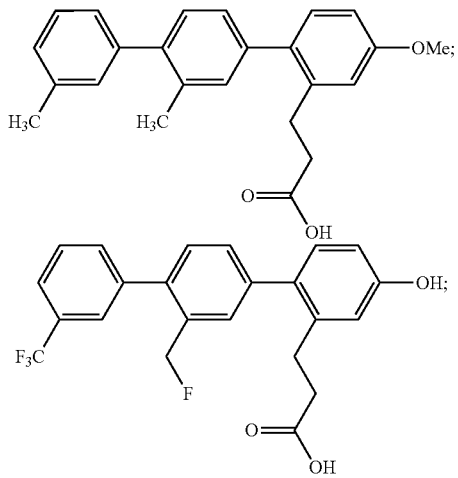

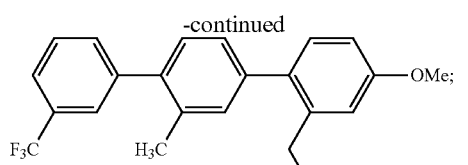

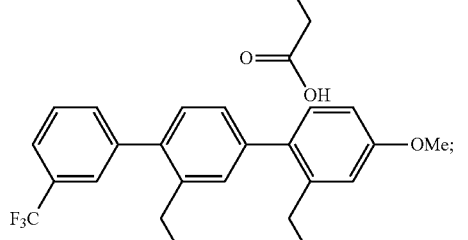

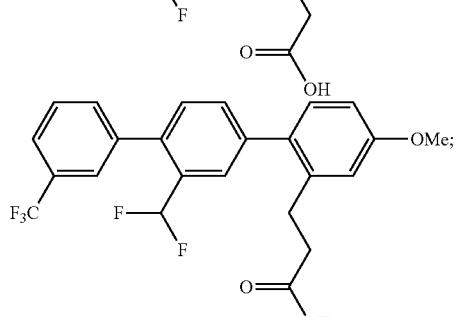

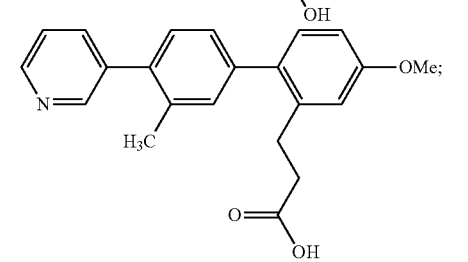

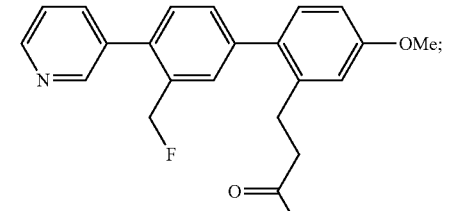

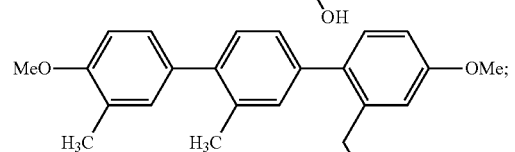

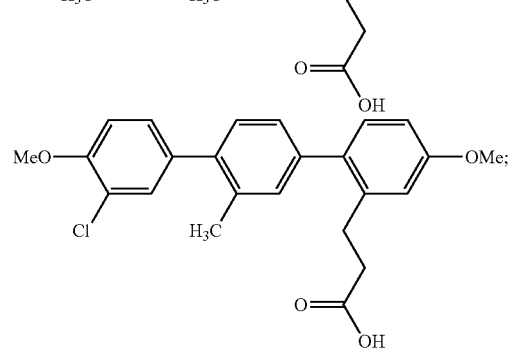

or a pharmaceutically acceptable salt thereof. Most preferably, the compound is

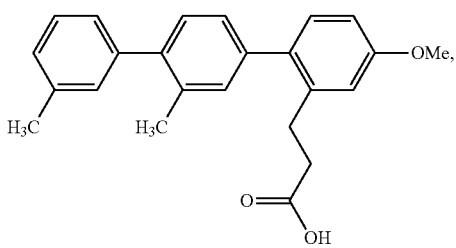 [SMILES: COc1ccc(-c2ccc(-c3cccc(C)c3)c(C)c2)c(CCC(=O)O)c1]

or a pharmaceutically acceptable salt thereof.

DEFINITIONS

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl. The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "halo" or "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4 (5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

The present invention may be better understood with reference to the accompanying examples that are intended for purposes of illustration only and should not be construed to limit the scope of the invention.

EXAMPLES

COL4A3BP gene in 5q13 expresses at least three polypeptides: 1) GPBP-1 (GPBP or 77 kD GPBP), a 624-residue-long polypeptide that is secreted and found in the extracellular space associated with type IV collagen (Raya et al. 1999; Revert et al. 2007; Revert et al. 2008); 2) GPBP-2 (as also known as GPBPA26 or CERT), a 598-residue-long cytosolic isoform mainly intracellular generated by mRNA alternative exon splicing (Raya et al. 2000; Revert et al. 2008); and 3) GPBP-3 (also known 91 kD GPBP), a membrane-bound 91-kD variant arising from alternative non canonical mRNA translation initiation (Revert et al. 2008).

GPBP-1 is a nonconventional Ser/Thr kinase displaying autophosphorylation activity that binds and phosphorylates the noncollagenous (NC1) domain of human type IV collagen α3 chain [α3(IV)NC1] (Raya et al. 1999 and 2000).

GPBP-1 forms large multimeric aggregates whose specific kinase activity is much higher than that of aggregates of lower molecular weight (Raya et al. 2000).

A five-residue-long motif $^{260}$SHCIE$^{264}$ (SEQ ID NO: 4) is the core of a motive which is critical for native GPBP-1 multimer assembly. An isolated peptide ($Q_2$) representing $^{260}$SHCIE$^{264}$ (SEQ ID NO: 4) and flanking regions (LATLSHCIELMVKR (SEQ ID NO: 8)) efficiently inhibits GPBP-1 kinase activity (Saus et al. 2008). Finally, organic compounds mimicking $Q_2$ ($Q_2$ peptidomimetics) also inhibit GPBP-1 kinase activity (Saus et al. 2010).

It is widely accepted that two main cell compartments exist in any type of tumor, cancer progenitor stem cells also known as side population (CSC/SP) and cancer transit-amplifying cells also known as major population (CTAC/MP). CSC/SP compartment contains self-renewing lineage with unusual unique ability to remain and perpetuate through time in the organism since they do not display replicative senescence. Typically, CSC/SP display low proliferation and apoptosis and high ability to efflux xenobiotic. CTAC/MP derive from CSC/SP but contrary to its progenitor these cells display limited ability to self-renewing and to remain and perpetuate in the organism since undergo replicative senescence. Still in contrast to CSC/SP, CTAC/MP are highly proliferating and display lower capacity to pump xenobiotic. Multiple evidence support that conventional chemotherapy mainly targets CTAC/MP since exploits the higher proliferating rates and low xenobiotic clearance of this compartment; however, because CSC/SP is reluctant to conventional treatments, relapsing of cancer commonly results from a novel CTAC/MP lineage displaying drug resistance and being fatal. Thus mounting evidence supports that drugs targeting CSC/SP rather than CTAC/MP compartment are needed to treat cancer and drug resistance more efficiently (for a review see Alberts et al. 2007)

We show that $Q_2$ peptidomimetic 3-[4"-methoxy-3,2'-dimethyl-(1,1';4',1")terphenyl-2"-yl] propionic acid, a GPBP kinase inhibitor called here T12, is synergistic with conventional drugs in treating cancer. Therapeutic effect of T12 results from selective targeting of CSC/SP compartment whose homeostasis is particularly dependent on GPBP expression.

Methods and Experimental Design

Chemicals

For cell culture assays doxorubicin hydrochloride and CFTR inhibitor-172 were purchased from Sigma, alamarBlue® from Invitrogen and BD™ Calcein AM Fluorescent Dye from BD Biosciences. For in vivo assays doxorubicin was purchased as injectable 2 mg/mL solution from Pfizer.

Terphenyl-12 (T12) was synthesized as previously described (compound 22b in WO2011/054530). T12 was suspended in water and neutralized with 1 M NaOH. The resulting solution was stirred at room temperature for 1 h and then freeze-dried to yield T12 sodium salt as a white powder.

Terphenyl-16 (T16) was synthesized according to the following procedure:

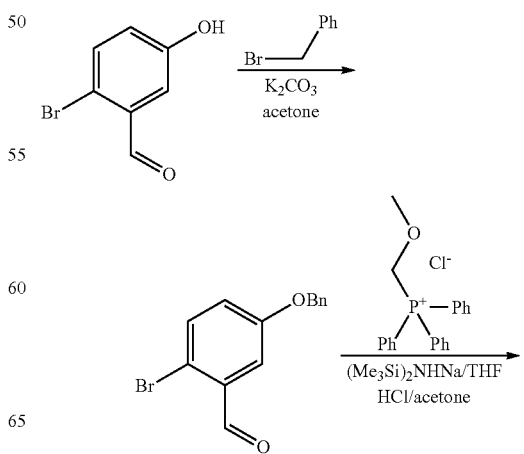

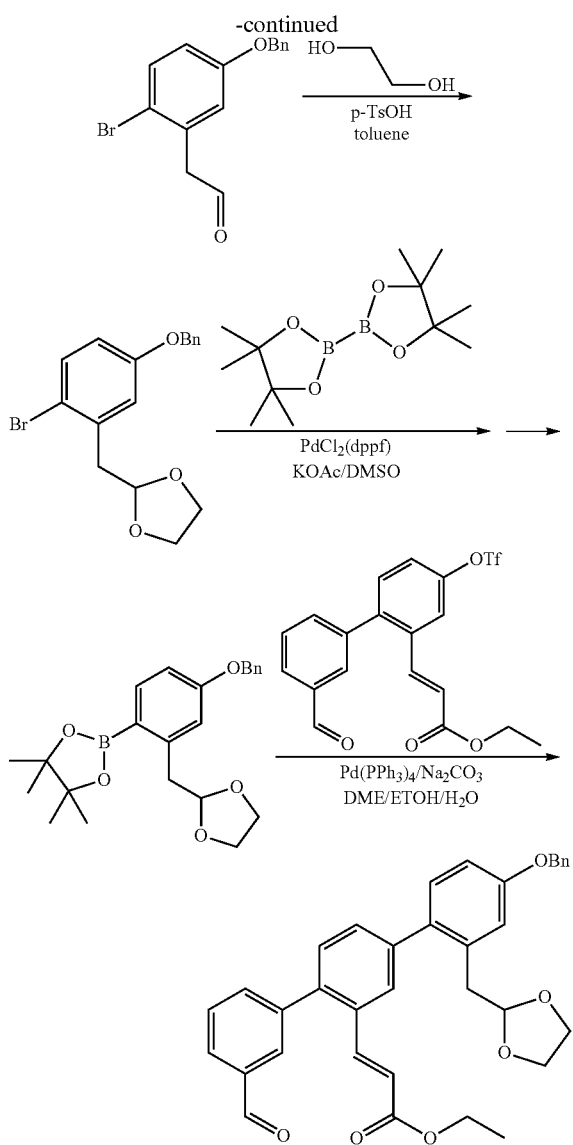

Specifically, to a solution of 2-bromo-5-hydroxybenzaldehyde (1.0 eq.) in anhydrous acetone were added potassium carbonate (2 eq.) and benzyl bromide (1.1 eq.).

The reaction mixture was stirred overnight at room temperature (r.t.), filtered and the solvent was removed under reduced pressure. The resulting crude reaction product was suspended in water and extracted with AcOEt. The combined organic layers were dried over $Na_2SO_4$, filtered and the volatiles were removed in vacuo to yield 5-(benzyloxy)-2-bromobenzaldehyde.

To a suspension of methoxymethyltriphenylphosphonium chloride (1.0 eq.) in dry THF cooled to 0° C., NaHMDS (1 M solution in THF, 1.0 eq.) was added, and resulting orange solution was stirred at 0° C. for 30 min. The reaction was cooled to −78° C. and a solution of 5-(benzyloxy)-2-bromobenzaldehyde (1.0 eq.) in THF was added dropwise, and the resulting mixture was warmed to r.t. and stirred for 1.30 h. Thereafter the reaction was quenched with water and the aqueous phase was extracted with dichloromethane and the collected organic layer dried over $Na_2SO_4$. The solvent was evaporated and the residue was purified by flash chromatography (hexane/AcOEt 50:1) to give the corresponding enolether as brownish oil; 6 N hydrochloric acid was added dropwise to a solution of the above compound in acetone and the resulting mixture was stirred at r.t. until consumption of the starting material. Thereafter water was added and the aqueous phase was extracted with dichloromethane, the collected organic layers were dried over $Na_2SO_4$, and the solvent evaporated to give the crude 2-[5-(benzyloxy)-2-bromobenzyl]-1,3-dioxolane as a yellowish oil which was immediately used for the next reaction.

2-[5-(benzyloxy)-2-bromobenzyl]-1,3-dioxolane (1.0 eq.), bis(pinacolato)diboron (1.1 eq.), potassium acetate (3.0 eq.), and [1,1′-bis(diphenylphosphino)ferrocene]dichloropalladium (II) complex with dichloromethane (0.03 eq.) were dissolved in anhydrous dimethylsulfoxide and the resulting mixture was heated overnight at 110° C. under inert atmosphere. Then, solvent was removed under reduced pressure and the residue was suspended in water and extracted with AcOEt. The organic layers were dried over $Na_2SO_4$, filtered, and evaporated. The crude reaction product was purified by flash chromatography on silica gel (hexane/AcOEt 20:1) to give 2-[(1,3-dioxolan-2-yl]-4-benzyloxyphenyl-4,4,5,5-tetramethyl-1,3,2-dioxaborolane.

Ethyl (E)-3-[3′-formyl-4-(trifluoromethanosulfonyloxy)biphenyl-2-yl]acrylate (1 eq.), 2-[(1,3-dioxolan-2-yl]-4-benzyloxyphenyl-4,4,5,5-tetramethyl-1,3,2-dioxaborolane (1.2 eq.) and palladium tetrakistriphenylphosfine (0.03 eq.) were dissolved in DME/EtOH (9:1). Then, a 2 M aq. $Na_2CO_3$ solution (2 eq.) was added to this yellow solution and the resulting mixture was refluxed overnight. After concentrating the mixture in vacuo the residue was taken up in water and extracted with AcOEt. The combined organic fractions were dried over $Na_2SO_4$, filtered, and evaporated. The crude reaction product was purified by means of flash chromatography on silica gel (hexane/AcOEt 5:1) to yield compound T16.

Terphenyl-55 (T55) was synthesized according to the following procedure:

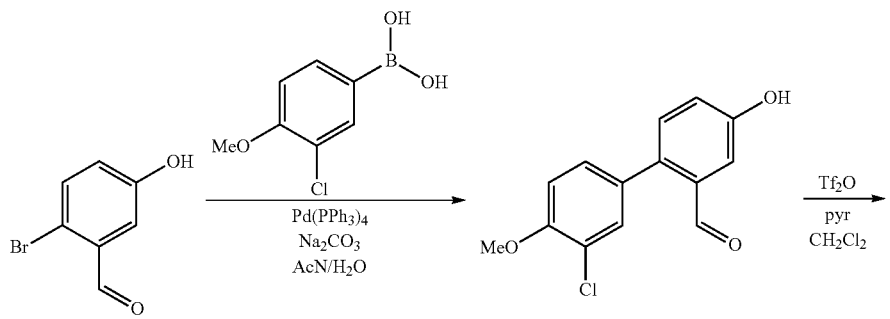

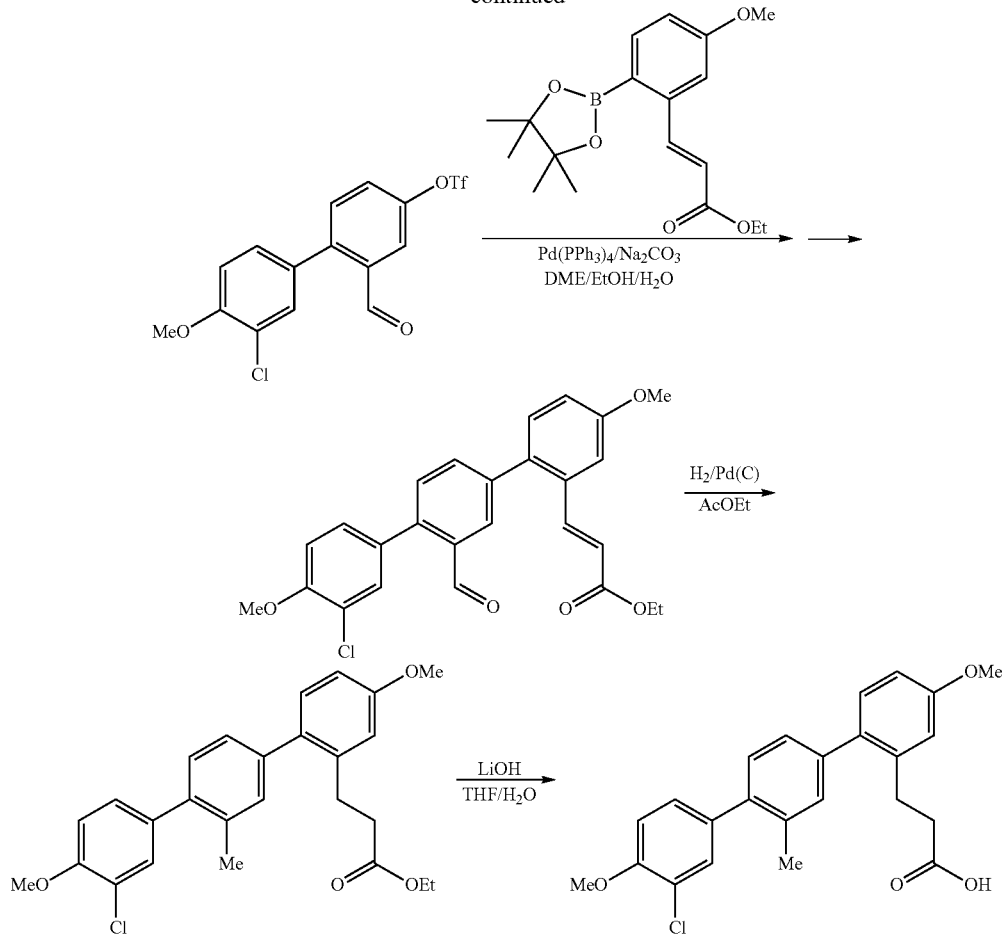

2-bromo-5-hydroxybenzaldehyde (1 mmol), 3-chloro-4-methoxyphenylboronic acid (1 mmol) and Na$_2$CO$_3$ (2 mmol) were dissolved in AcN/H$_2$O (7:3). Then, palladium tetrakistriphenylphosfine (0.03 mmol) was added and the resulting mixture was refluxed until completion. After concentrating the mixture in vacuo the residue was taken up in water and extracted with AcOEt. The combined organic fractions were dried over Na$_2$SO$_4$, filtered, and evaporated. The crude reaction product was purified by means of flash chromatography on silica gel (hexane/AcOEt 5:1) to yield 3'-chloro-4-hydroxy-4'-methoxybiphenyl-2-carbaldehyde as a white solid (93%); m.p.: 168-170° C.

A solution of 3'-chloro-4-hydroxy-4'-methoxybiphenyl-2-carbaldehyde (0.93 mmol) and pyridine (2.78 mmol) in dry CH$_2$Cl$_2$ was cooled at 0° C. Then a solution of triflic anhydride (1.02 mmol) in dry CH$_2$Cl$_2$ was added dropping under nitrogen atmosphere. The mixture was stirred at room temperature (r.t.) until consumption of the starting material. Then, it was quenched with NaHCO$_3$ saturated solution and extracted with CH$_2$Cl$_2$. The combined organic layers were dried over Na$_2$SO$_4$, filtered, concentrated in vacuo and purified by flash chromatography on silica gel (hexane/AcOEt 10:1) to give 3'-chloro-2-formyl-4'-methoxybiphenyl-4-yl trifluoromethanesulfonate as a yellowish oil (93%).

3'-chloro-2-formyl-4'-methoxybiphenyl-4-yltrifluoromethanesulfonate (2.24 mmol), (E)-ethyl 3-[5-methoxy-2-(4,4,5,5-tetramethyl-1,3,2-dioxaborolan-2-yl)phenyl]acrylate (2.46 mmol) and palladium tetrakistriphenylphosfine (0.06 mmol) were dissolved in DME/EtOH (9:1). Then, a 2 M Na$_2$CO$_3$ aqueous solution (4.48 mmol) was added to this yellow solution and the resulting mixture was refluxed until completion. Solvents were concentrated in vacuo and the residue was taken up in water and extracted with AcOEt. The combined organic fractions were dried over Na$_2$SO$_4$, filtered, and evaporated. The crude reaction product was purified by means of flash chromatography on silica gel (hexane/AcOEt 5:1) to yield ethyl (E)-3-[3-chloro-2'-formyl-4,4"-dimethoxy-(1,1';4',1")terphenyl-2"-yl]acrylate as a white solid (54%); m.p.: 150-152° C.

To a solution of ethyl (E)-3-[3-chloro-2'-formyl-4,4"-dimethoxy-(1,1';4',1")terphenyl-2"-yl]acrylate (1.22 mmol) in AcOEt, 10% palladium on carbon as catalyst (25% w/w) was added and it was hydrogenated overnight at 25 atm of pressure and r.t. Thereafter, the mixture was filtered over Celite and the filtrates concentrated in vacuo. The crude reaction product was purified by chromatography on silica gel (hexane/AcOEt 20:1) to give ethyl 3-[3-chloro-2'-methyl-4,4"-dimethoxy-(1,1';4',1")terphenyl-2"-yl]propionate as a transparent oil (63%).

To a solution of ethyl 3-[3-chloro-2'-methyl-4,4"-dimethoxy-(1,1';4',1")terphenyl-2"-yl]propionate (0.70 mmol) in a 4:1 tetrahydrofuran/water mixture, monohydrated lithium hydroxide (2.1 mmol) was added and the reaction was stirred at r. t. until consumption of the starting material. Then THF was removed under reduced pressure, the aqueous layer was acidified with 1 M HCl solution, and extracted with AcOEt. The organic layers were combined, dried over Na$_2$SO$_4$, filtered and removed in vacuo under reduced pressure to yield T55 compound as a white solid (98%); m.p.: 135-137° C. $^1$H RMN (300 MHz, CDCl$_3$) δ ppm: 7.51 (d, J=2.1 Hz, 1H), 7.37-7.20 (m, 5H), 7.09 (d, J=8.4 Hz, 1H), 6.95 (d, J=2.4 Hz, 1H), 6.93 (dd, J=8.4 Hz, J=2.4 Hz, 1H), 4.06 (s, 3H), 3.94 (s, 3H), 3.07 (t, J=8.0 Hz, 2H), 2.63 (t, J=8.0 Hz, 2H), 2.40 (s, 3H); $^{13}$C RMN (75 MHz, CDCl$_3$) δ ppm: 178.9, 158.9, 153.9, 140.2, 138.9, 138.7, 135.2, 135.0, 134.2, 131.3, 131.0, 129.6, 128.5, 126.8, 122.0, 114.5, 111.7, 111.6, 56.2, 55.3, 35.1, 28.2, 20.5; HRMS (EI) m/z: calcd for C$_{24}$H$_{23}$ClO$_4$: 428.1623 (M+NH$_4$). found: 428.1632.

Recombinant GPBP and In Vitro Assays

Recombinant yeast GPBP-1 was expressed in *Pichia pastoris* and affinity-purified as previously described (Raya et al. 1999, raya et al. 2000). To express and purify recombinant FLAG-GPBP-1 from SF9 insect cells, the cDNA of FLAG-GPBP-1 was cloned in the baculovirus expression vector pFastBac1. The plasmid was transformed into DH10Bac competent cells and the recombinant baculovirus was produced following manufacturer's recommendations (Bac-to-Bac™ Baculovirus Expression System, Invitrogen, Life Technologies). Baculovirus was used to infect SF9 cells and GPBP-1 in the supernatant of culture media was purified by affinity chromatography using anti-FLAG agarose (Sigma-Aldrich) following manufacturer's recommendations. GPBP-1 phosphorylation assays were performed as previously described (Raya et al. 1999).

Affinity constants of T12 and doxorubicin for GPBP-1 were calculated by the Benesi-Hildebrand method (Faizul et al. 2008).

Cell Cultures

A549 human lung adenocarcinoma cancer cells (CLS Cell Lines Service) were used as an ex vivo model for the assessment of anti-tumor activity of specific compounds. Unless otherwise indicated A549 cells were cultured in DMEM: Ham's F12 medium supplemented with 2 mM L-glutamine and 10% fetal bovine serum. A549 cells resistant to doxorubicin (A549-DR) were obtained treating cells with 1 µM for 4 weeks. A549 cells were transfected with a plasmid that expresses GPBP-1 and further selected with G418 (Invitrogen) to obtain a cell line (A549-GPBP) that constitutively expresses GPBP-1.

JLSM cells were obtained from a human lung epidermoid carcinoma biopsy following standard procedures. Specifically, biopsy was cut lengthways and 2 mm explants were deposited in a 6 well plate coated with collagen (Sigma-Aldrich) and kept in a humidified 37° C. incubator with 5% (v/v) CO$_2$ for 15 minutes to facilitate cellular binding to collagen I matrix. Subsequently, explants were further incubated with 1 mL per well of serum-free B-ALI™ air-liquid interface medium from Clonetics™ (B-ALI medium). When cells started to grow, explants were removed and cells passed to a collagen I coated flask with fresh medium. Cultures were kept in a humidified 37° C. incubator with 5% (v/v) CO2 and 95% (v/v) air.

Cytotoxicity Assays

Cytotoxicity assays were performed with alamarBlue® reagent (Invitrogen) according to manufacturer's instructions. A549 cells were seeded on 96-well culture plates (7,500 cells/well) and allowed to settle during 4 h. Then, cells were cultured with individual peptidomimetics at concentrations ranging from 0 to 50 µM, in presence of doxorubicin at concentrations ranging from 0 to 10 µM for 36 h. JLSM cells were harvested by treatment with 0.25% trypsin (Lonza) and plated on collagen I coated 96-well black culture plate (Perkin Elmer) at a density of 10.000 cells per cm$^2$. After 4 h settling, cells were treated with different peptidomimetics (with or without doxorubicin) for 36 h. Subsequently alamarBlue® reagent was added and incubation maintained for 3 h. Fluorescence was measured using 560EX nm/590EM nm filter settings with a SpectraMax GeminiXPS (Molecular Devices). Blank wells containing media were used to determine background fluorescence.

RNA Extraction and Taqman™ Gene Expression Analysis

Total RNA from cell samples was extracted using Ilustra RNAspin™ Mini (Ge Healthcare) according to the manufacturer's instructions. One µg of total RNA from each sample was converted to cDNA (RT) using the High Capacity cDNA Reverse Transcription Kit (Applied Biosystems). For Real-Time PCR (qPCR), 1.5 µl of cDNA was mixed with TaqMan™ Gene Expression Master Mix and the specific TaqMan™ probes and primers for COL4A3BP/GPBP, DDIT3/CHOP, CDKN1A/p21, PROM1/CD133, NANOG, MMP10 and HPRT1, all from Applied Biosystems. Hypoxanthine-guanine phosphoribosyltransferase (HPRT1) primer was used as endogenous control. qPCR was performed on a StepOnePlus™ Real-Time PCR system (Applied Biosystems) according to manufacturer's recommendations. The relative levels of mRNAs were calculated with the ΔΔCt method using untreated samples as reference (the comparative Ct method).

siRNA Transfection

Chemically synthesized p21 siRNA (5' CAAGGAGUCAGACAUUUUAtt 3')'(SEQ ID NO: 12) and siRNA negative control were designed and purchased from Ambion Inc. In vitro transient transfection was done using MagnetoFection™ (Ozbiosciences) following the manufacturer's procedures.

PCR Array Studies

RNA was purified from cells using the Ilustra RNAspin Mini (GE Healthcare) and the cDNA was prepared using RT$^2$ First Strand™ cDNA kit (Qiagen). The cDNA from treated or untreated cells was used to screen the Cell Cycle RT$^2$ Profiler™ PCR Array for human (PAHS-020Z, Qiagen), following manufacturer's procedures (Qiagen). qPCR was performed using RT$^2$ SYBR® Green ROX™ qPCR Mastermix (Qiagen) and the StepOnePlus™ Real-Time PCR System (Applied Biosystems). qPCR data were analyzed using manufacturer software.

Microarrays Analysis

For mRNA expression analysis, A549, A549-DR and A549-GPBP cells were lysed and total RNA was extracted with RNeasy™ Protect mini kit (Qiagen) according to manufacturer's recommendations. RNA was quantified by spectrometry with a NanoDrop ND1000 (NanoDrop Technologies) and quality confirmed by RNA 6000 Nano Bioanalyzer (Agilent Technologies) assay. Briefly, 150 ng of total RNA were used to produce Cyanine 3-CTP-labeled cRNA using the Low Input Quick Amp Labelling Kit One-Color (Agilent) according to the manufacturer's instructions. Following 'One-Color Microarray-Based Gene Expression Analysis' protocol Version 6.0 (Agilent), 1.6 µg of labeled cRNA were hybridized with the Whole Human Genome Oligo Microarray Kit (Agilent) containing 41,000+ unique human genes and transcripts. Arrays were scanned in an Agilent Microarray Scanner according to the manufacturer's instructions and data extracted using Agilent Feature Extraction Software 10.7.1 following the Agilent protocol GE1_107_Sep09, grid template 014850_D_F_20100430 and the QC Metric Set GE1_QCMT_Sep09.

Raw data files were background corrected using supplier's methodology and intensity signal standardized across arrays via quantile normalization algorithm. Differential gene expression assessment of all comparisons was carried out using limma moderated t-statistics. Conventional adjustment for multiple testing proposed by Benjamini Hochberg (Benjamini et al. 1995) was used to derive adjusted P-values.

Flow Cytometry Analysis of Cleaved PARP

Caspase-3 activation in A549 cells was evaluated by flow cytometry using a human anti-cleaved PARP antibody conjugated to PE (BD Biosciences). Briefly, after treatment, the cells were collected by centrifugation and suspended in Perm/Wash™ (BD Biosciences) buffer for 20 min, washed and then incubated for 30 min with the antibody. Subsequently, the cells were rinsed and further analyzed by flow cytometry (BD FacsVerse™ cytometer, BD Biosciences).

Migration Assays

Migration assays were performed using modified Boyden chambers (Transwell inserts, 6.5 mm diameter; Corning). Inserts containing polycarbonate membranes with 8 µm pores were placed into the lower chambers containing 400 µl media (DMEM:F-12 supplemented with 10% FBS, 1% penicillin-streptomycin and 2 mM glutamine). Serum-starved A549 cells were removed from culture dishes with Hanks' balanced salt solution containing 0.5% trypsin and 0.2% EDTA (Sigma), washed and suspended in media without serum (DMEM:F-12, 1% penicillin-streptomycin and 2 mM glutamine) at $10^6$ cells/mL. Two-hundred fifty thousand (250,000) cells in 250 µL media without serum were added to the top of each migration chamber and allowed to migrate to the underside of the porous membrane for 16 h. T12 and doxorubicin were present in the media of both top and bottom compartments throughout the assay. The non-migratory cells on the upper membrane surface were removed, and the migratory cells attached to the bottom surface of the membrane were detached with Hanks' balanced salt solution containing 0.5% trypsin and 0.2% EDTA. The detached cells were labeled with Calcein AM Fluorescent Dye (4 µg/ml) for 90 min at 37° C. and the fluorescence was measured at 494/517 nm (Abs/Em).

Side Population Staining

A549 cells were suspended at $10^6$ cells/mL in culture medium containing 10 mM Hepes (previously warmed at 37° C.). Hoechst 33342 was added at 5 µg/mL and cells incubated in a 37° C. bath with shaking for 90 min in the dark. Before incubation (and after staining) an aliquot of 1 mL was taken and verapamil (50 µM) and fumitremorgin C (10 µM) added. Cells were centrifuged at 300×g for 5 min at 4° C. and suspended in cold medium with 10 mM Hepes. Cells were kept at 4° C. until analysis. Analysis of Hoechst 33342 efflux was assessed using a Flow Cytometer with incident 350 nm ultraviolet light. The resulting fluorescence was measured at two wavelengths using 424/44 BP and 675 LP filters that allow detection of Hoechst blue and red, respectively. Side population shows low emission of fluorescence at both blue and red channels, whereas major population (MP) displays higher emission. Doxorubicin content in either population was estimated with incident 488 nm blue light and 585/40 filter. Verapamil and fumitremorgin C werer used to identify SP region.

Mouse Xenografts Studies

Ten-week old nude mice (NMRi-Foxn1$^{nu}$/Foxn1$^{nu}$) (Janvier) were used for xenograft studies. Three-million A549 cells were suspended in 100 µL of culture medium, mixed with 200 µL Matrigel (BD) and subcutaneously injected on the flank of individual mouse (n=40). Tumor size was periodically measured with a digital caliper and volumes were calculated with the formula Volume=(Length×Width)/2. When tumors reached ~400 mm$^3$ mice were randomly separated into four groups (n=10 for each group) and subjected to treatments with: 1) 2.5 mg/kg doxorubicin per week (i. p); 2) 20 mg/kg T12 per day administered with drinking water, considering a daily water intake of 6 mL per mouse); 3) 2.5 mg/kg/week doxorubicin and 20 mg/kg/day T12; and 4) vehicles. After three weeks mice were sacrificed, tumor xenografts excised and either fixed with formalin and paraffin-embedded or frozen and RNA extracted.

Sections of paraffin-embedded tumor samples were subjected to hematoxylin and eosin and Masson's trichrome standard stainings. Frozen tumor samples were ground with a mortar in liquid nitrogen and total RNA extracted as above indicated.

Results

Doxorubicin Inhibits GPBP-1 Kinase Activity in a Different Fashion than T12 and Both Inhibitors Display Synergistic Biological Activity (Reduction of Cancer Cell Viability).

To explore the possibility that doxorubicin, an anti-tumor agent targeting topoisomerase II (Pommier et al. 2010), operates through GPBP-1, human recombinant GPBP-1 (Raya et al. 1999) was subjected to in vitro autophosphorylation in the presence or absence of doxorubicin and T12 (FIG. 1A). Doxorubicin efficiently inhibited GPBP-1 autophosphorylation and inhibitory activity was synergistic with T12. This supports the notion that doxorubicin and T12 target GPBP-1 in a different fashion. Accordingly, analysis of individual inhibitor binding to GPBP-1 revealed major differences in the affinity constant of individual inhibitors (FIG. 1B). Thus doxorubicin bound to GPBP-1 by ~$10^5$-fold stronger than T12, revealing that doxorubicin bound GPBP-1 in a virtually "irreversible" manner whereas T12 displayed a significantly more light-moderated affinity and therefore is expected to display more "reversible" binding. In addition, consistent with the notion that inhibitors bound to GPBP-1 in different sites, T12 reduced doxorubicin LC50 for A549 cells in a dose-dependent manner (FIG. 2). Interestingly, A549 cells increased GPBP cell expression in response to doxorubicin and this was associated to development of doxorubicin-resistance (see below). In contrast, ovarian cancer cells (OVCAR-3) which did not increase GPBP expression in response to doxorubicin were not responsive to T12. Interestingly, recombinant expression of GPBP-1 in OVCAR-3 cells increases doxorubicin LC50 and sensitized these cells to T12 treatment, indicating that chemoresistance can be induced by increased GPBP-1 expression and counteracted by $Q_2$ peptidomimetics (data not shown).

Similar results were observed using etoposide, an independent anti-neoplastic with a similar mechanism of action of doxorubicin (topoisomerase II poisoning) (Pommier et al. 2010). Similar results were seen with other compounds of the invention, for example, 15b, 22f, 22h, 22j, and 32 (Table 1).

TABLE 1
| STRUCTURE | Mr | Activity as enhancer of doxorubicin-induced cell death (factor of reduction of doxo LC50 |
|---|---|---|
| 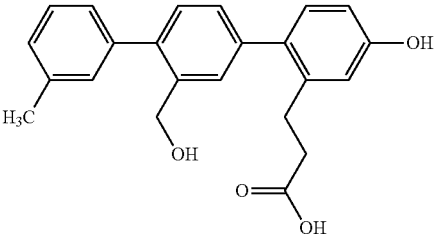<br>1a | 362.42 | −/+<br>50 μM, 1.6 |
| 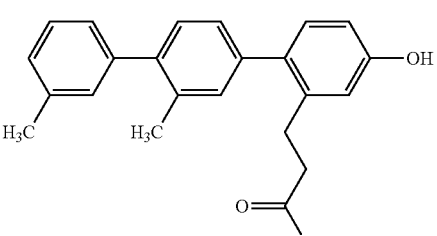<br>12a | 346.42 | ++<br>50 μM, 2.9 |
| 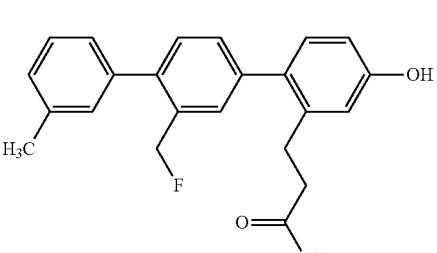<br>15a | 364.41 | ++<br>50 μM, 3.2 |
| 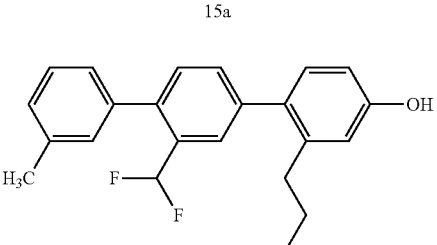<br>20a | 382.40 | ++<br>50 μM, 2.7 |
| 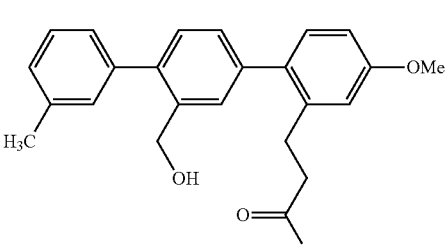<br>22a | 376.44 | −/+<br>50 μM, 1.6 |

TABLE 1-continued
| STRUCTURE | Mr | Activity as enhancer of doxorubicin-induced cell death (factor of reduction of doxo LC50 |
|---|---|---|
| 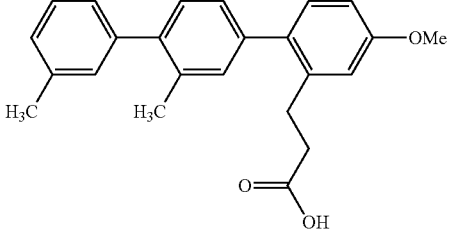 [SMILES: COc1ccc(-c2ccc(-c3cccc(C)c3)c(C)c2)c(CCC(=O)O)c1]<br>T-12<br>22b | 360.45 | +++<br>50 µM, 4.0 |
| 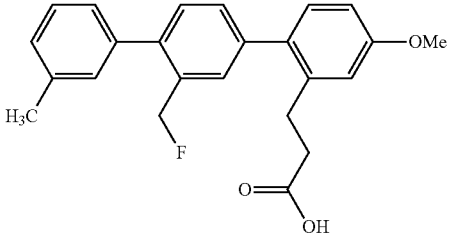<br>22c | 378.44 | ++/+++<br>50 µM, 3.3 |
| 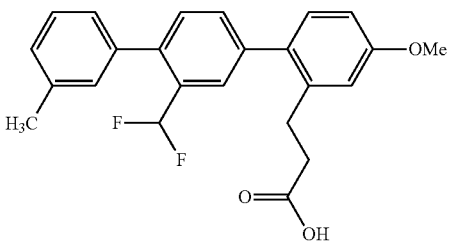<br>22d | 396.43 | ++/+++<br>50 µM, 3.2 |
| 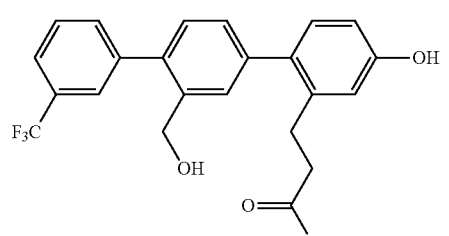<br>1b | 416.39 | –<br>50 µM, 1.4 |
| 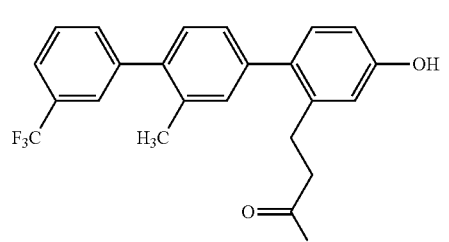<br>12b | 400.39 | +<br>50 µM, 2.0 |

TABLE 1-continued

| STRUCTURE | Mr | Activity as enhancer of doxorubicin-induced cell death (factor of reduction of doxo LC50 |
|---|---|---|
| 15b | 418.38 | ++++<br>50 µM, 4.7 |
| 20b | 436.37 | ++<br>50 µM, 3.0 |
| 22e | 430.42 | +<br>50 µM, 2.0 |
| 22f | 414.42 | +++<br>50 µM, 3.4 |
| 22g | 432.41 | ++/+++<br>50 µM, 4.0 |

TABLE 1-continued

| STRUCTURE | Mr | Activity as enhancer of doxorubicin-induced cell death (factor of reduction of doxo LC50 |
|---|---|---|
| 22h | 450.40 | ++/+++<br>50 µM, 4.0 |
| 1c | 349.38 | +<br>50 µM, 2.4 |
| 13c | 377.43 | +<br>10 µM, 1.7 |
| 15c | 397.41 | +<br>50 µM, 1.8 |
| 20c | 369.36 | +<br>50 µM, 1.8 |

TABLE 1-continued

| STRUCTURE | Mr | Activity as enhancer of doxorubicin-induced cell death (factor of reduction of doxo LC50 |
|---|---|---|
| T-42 | 363.41 | –<br>50 μM, 1.0 |
| T-6<br>22i | 363.41 | –<br>50 μM, 1.0 |
| 22j | 347.41 | ++++<br>50 μM, 5.8 |
| 22k | 365.40 | +++<br>50 μM, 4.0 |
| 22l | 383.39 | ++/+++<br>50 μM, 3.2 |

TABLE 1-continued
| STRUCTURE | Mr | Activity as enhancer of doxorubicin-induced cell death (factor of reduction of doxo LC50 |
|---|---|---|
| 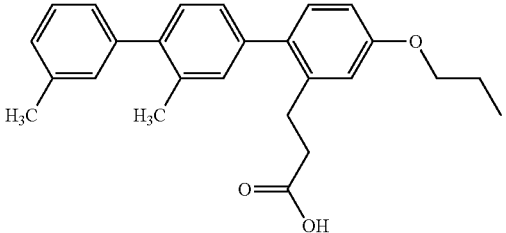 24a | 388.50 | ++<br>25 μM, 2.6 |
| 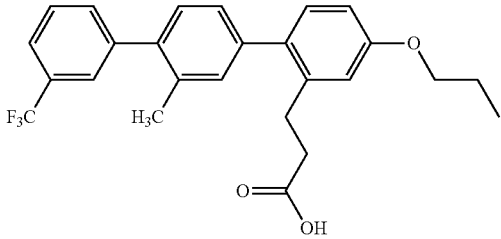 24c | 442.47 | ++<br>10 μM, 1.8 |
| 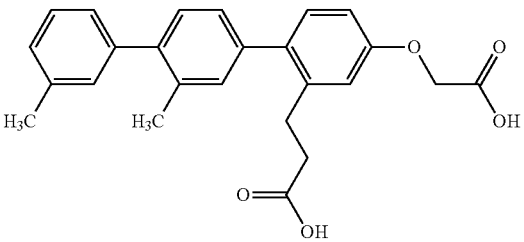 24b | 404.46 | −<br>50 μM, 1.0 |
| 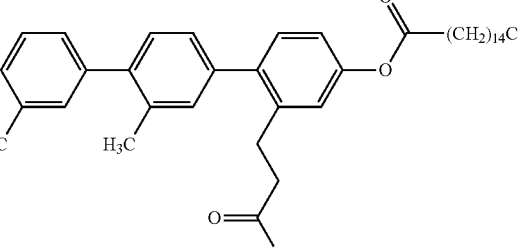 T-43 | 584.83 | −<br>50 μM, 1.0 |
| 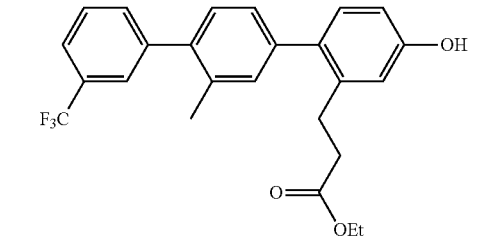 11b | 428.44 | −? |

TABLE 1-continued

| STRUCTURE | Mr | Activity as enhancer of doxorubicin-induced cell death (factor of reduction of doxo LC50 |
|---|---|---|
| T-16 | 548.62 | ++/+++<br>50 µM, 3.5 |
| 2a | 374.47 | +<br>50 µM, 1.5 |
| T-45 | 376.44 | +<br>50 µM, 2.0 |
| 32 | 390.47 | ++++<br>50 µM, 5.2 |
| T-55 | 410.89 | ++++<br>25 µM, 5.2 |

Table 1.

The activity shown for each compound in Table 1 is the factor by which doxorubicin LC50 is reduced by the compound at a 50-µM concentration in A549 cell cultures. For example, if the LC50 is 0.9 µM for doxorubicin in A549 cultures, and the activity factor for 50 µM compound 22b (T12) is 4.0, that means that in presence of 50 µM compound 22b, the doxorubicin LC50 becomes 0.9/4=0.225 µM. For some compounds (13c, 24a, 24c) lower concentrations have been used for assessment of doxorubicin-enhancing activities because the compounds are significantly toxic by themselves at 50 μM. The symbols –, –/+, +, ++, +++, ++++ in the third column are used to show relative activities of compounds in a simplified way.

T12 Enhances the Induction of CDKN1A and DDIT3 Genes in Response to Chemotherapeutic Agents GPBP-1 recombinant expression induced CDKN1A gene expression (Table 2). CDKN1A encodes for p21 (SEQ ID NOS: 10 (cDNA) and 11 (protein), a cyclin-dependent kinase inhibitor that promotes cell cycle arrest in response to DNA damage (Bartek & Lukas 2001).

Figure 3:
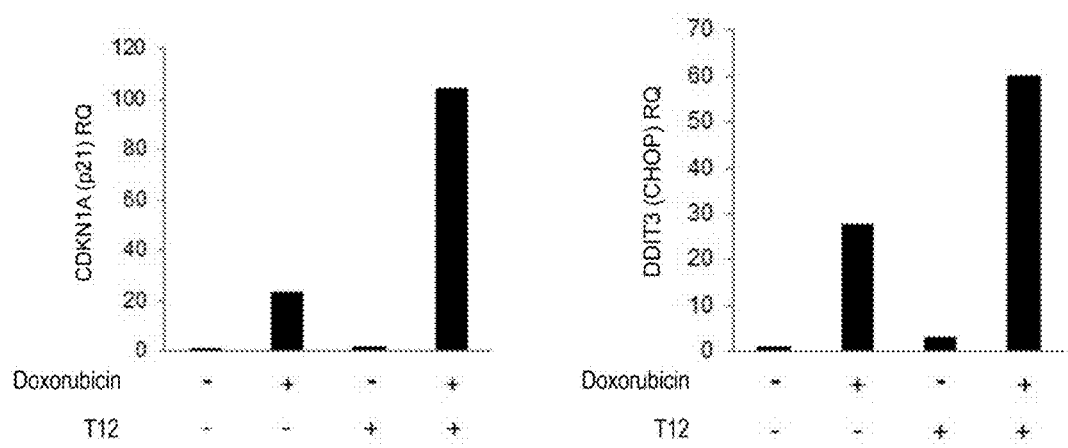
FIG. 3. T12 enhances doxorubicin-induced expression of CDKN1A (p21) and DDIT3 (CHOP) genes in A549 cells. Cells were treated with doxorubicin (1 µM) and/or T12 (50 µM) for 24 h. Total RNA was isolated, reverse-transcribed, and CDKN1A (p21) and DDIT3 (CHOP) mRNA levels assessed by qPCR using TaqMan™ commercial probes and primers. Results are expressed as relative quantity (RQ) respect to untreated cells. A representative assay is shown.

Moreover, doxorubicin has been reported to enhance the expression of DDIT3 (Lai et al. 2010). DDIT3 encodes for CHOP, a transcription factor mediating cell death induced by unfolded protein response (Zinszner et al. 1998). So we assessed the involvement of CDKN1A (p21) and DDIT3 (CHOP) in the response of A549 cells to doxorubicin and/or T12 using a qPCR approach (FIG. 3). In our assays conditions T12 was synergistic with doxorubicin inducing both CDKN1A (p21) and DDIT3 (CHOP) expression.

CDKN1A/p21 Counteracts T12-Induced Cell Death

Figure 4:
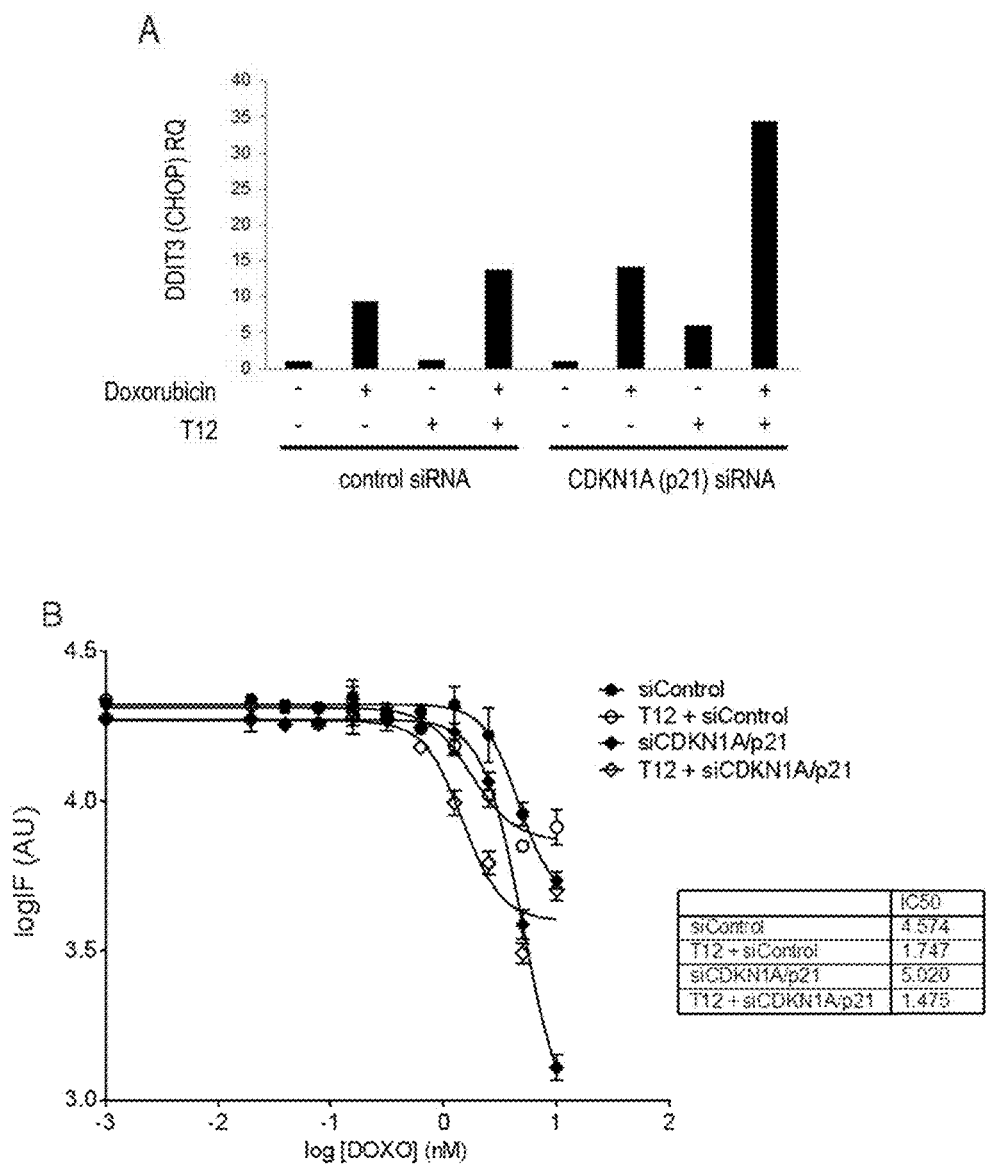
FIG. 4. p21 counteracts T12 and doxorubicin synergistic biological activity. A549 cells were magnetofected with p21-targeting siRNA or with a control siRNA for 24 h. A, transfected cells were treated with doxorubicin (1 µM) and/or T12 (50 µM) for 24 h. Subsequently, total RNA was isolated, reverse-transcribed, and mRNA levels of DDIT3 (CHOP) gene were assessed by qPCR as in FIG. 3. Results are expressed as relative values (RQ) respect to untreated cells transfected with control siRNA. A representative assay is shown. B, transfected cells were seeded in 96-well plates and treated and analyzed as in FIG. 2. Lethal concentration 50 (LC50) for each combination is indicated in the table. Two-way ANOVA test indicates that differences among combinations are statistically significant (P<0.0001).

Previous studies have shown that DDIT3/CHOP down regulates CDKN1A/p21 expression (Mihailidou et al. 2010 and Kim et al. 2012). Now we demonstrate that down-regulation of CDKN1A/p21 increased DDIT3/CHOP expression (FIG. 4A) and cell death (FIG. 4B) in doxorubicin and T12-treated A549 cells, suggesting that T12 synergism is mediated by CHOP and counteracted by p21.

T12 Enhances Doxorubicin-Induced Caspase-3-Mediated Apoptosis

Figure 5:
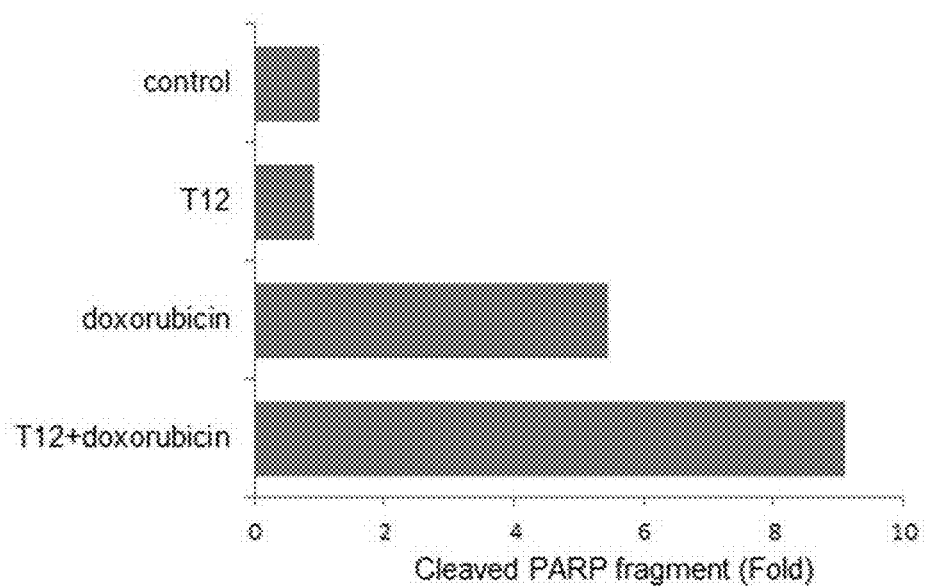
FIG. 5. T12 enhances doxorubicin-induced caspase 3-mediated apoptosis. A549 cells were incubated with doxorubicin (1 µM) and/or T12 (50 µM) for 36 h. Subsequently, cells were stained with a PE conjugated antibody specific for human PARP-cleaved fragments and further analyzed by flow cytometry. Data are expressed as fold respect to untreated control cells. Shown is a representative experiment.

It has been shown that poly (ADP-ribose) polymerase (PARP) undergoes cleavage during cell apoptosis (Sithanandam et al. 2005). PARP cleavage was typically performed by apoptotic effector caspase-3 (Lazebnik et al. 2004) and thus PARP cleavage can be used to monitor caspase-3-mediated apoptosis. Interestingly, T12 enhanced doxorubicin-induced PARP cleavage in A549 cultured cells, suggesting that caspase-3-dependent apoptosis mediates T12 and doxorubicin synergism reducing cell viability (FIG. 5). T12 enhanced both CHOP expression (see FIG. 3 above) and PARP cleavage in doxorubicin-treated A549 cells indicating that T12 up-regulated UPR-associated apoptosis.

Doxorubicin and T12 Induce a Similar Transcriptional Profile of the Cell Cycle-Related Genes in A549 Cells.

Figure 6:
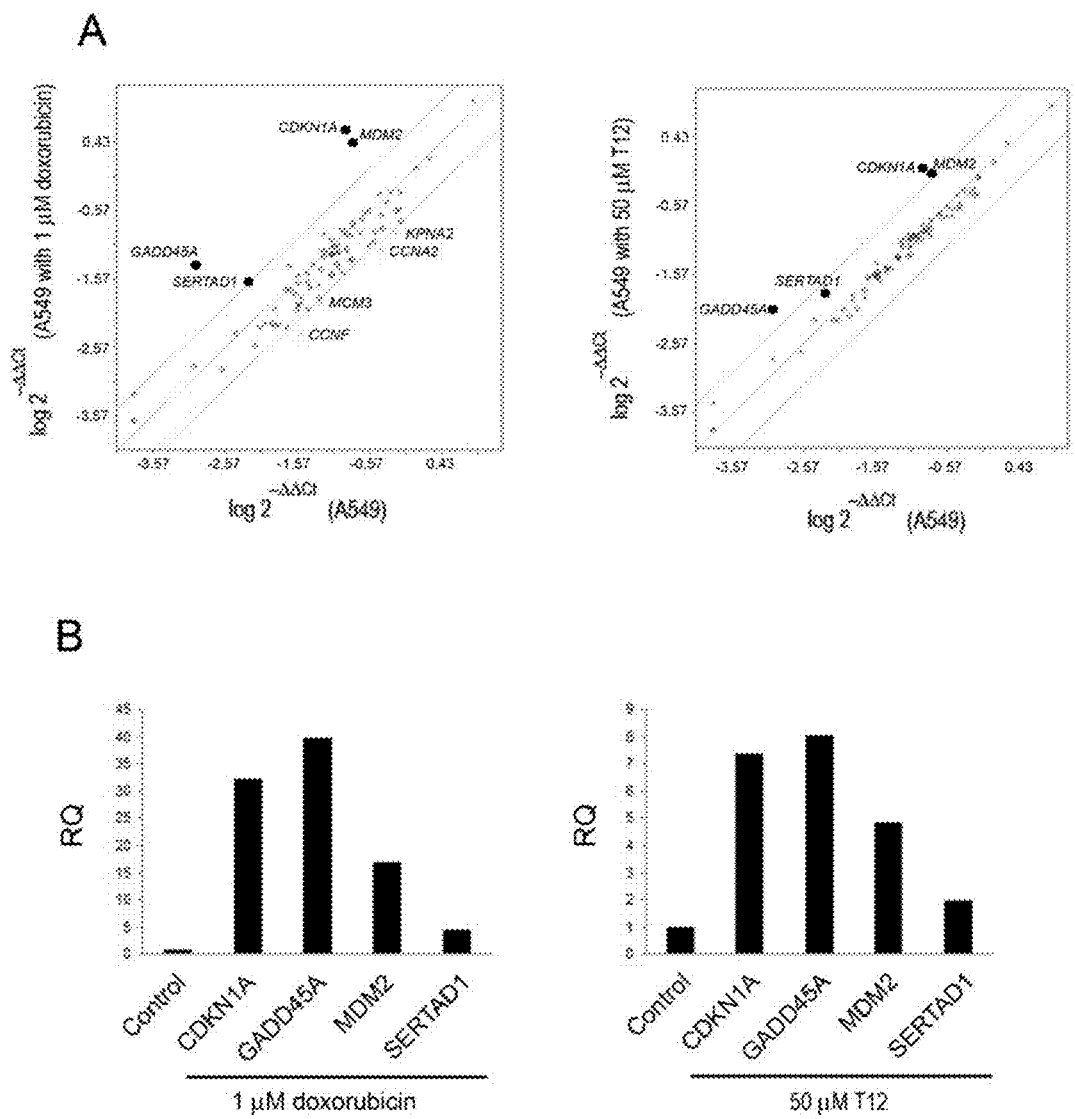
FIG. 6. T12 and doxorubicin activate cell cycle-related genes in a similar fashion. A549 cells were treated doxorubicin (1 µM) or T12 (50 µM) for 24 h. Total RNA was purified, reverse-transcribed and subjected to Cell Cycle RT$^2$ Profiler PCR Array. A, shown are logarithmic scatter plots of relative mRNA levels of treated vs untreated cells. Dots above and below the middle line denote genes being up- or down-regulated in response to treatment, respectively. B, shown are bar plots of the relative expression (RQ) of the over-expressed genes indicated in A. Results are shown in fold expression respect to untreated cells.

Using Cell Cycle RT² Profiler PCR Arrays (Qiagen) we explored doxorubicin or T12 induced gene expression in A549 cells (FIG. 6). CDKN1A (p21), GADD45A (growth arrest and DNA-damage-inducible, alpha), p53 inhibitor MDM2, and SERTAD1 were all up-regulated in either doxorubicin- or T12-treated cells. Although the induction was more prominent in doxorubicin-than in T12-treated cells the relative expression among individual genes for each individual treatment was similar. These results suggested that doxorubicin and T12 operated through coincidental pathways in A549 cells.

CFTR/ABCC7 Counteracts the Cytotoxic Effects of T12

Figure 7:
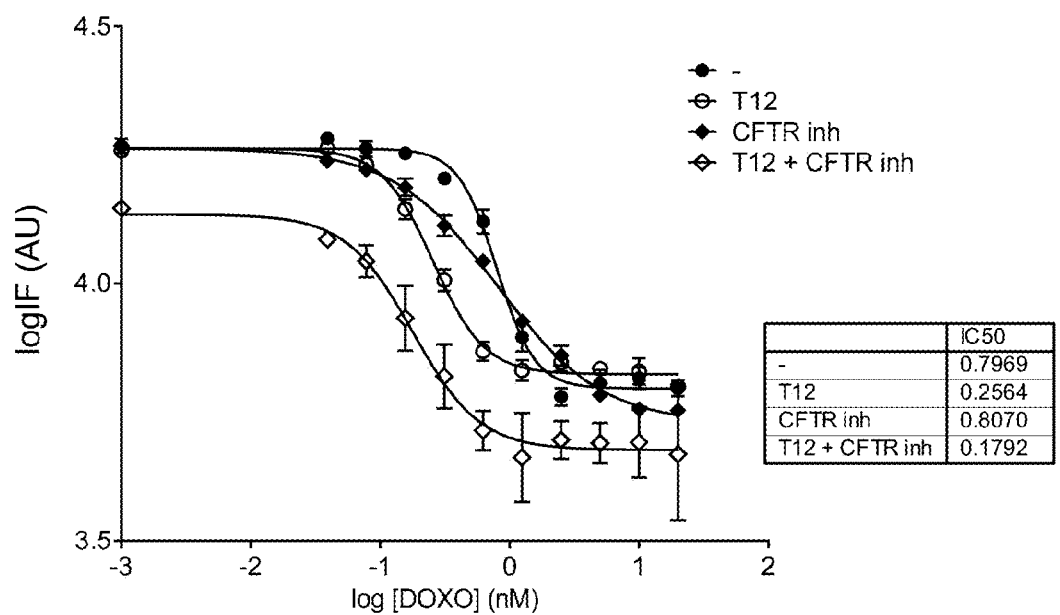
FIG. 7. CFTR inhibition reduces cell viability of A549 cultures treated with T12. A549 cells were seeded on 96-well culture plates and after 4 h were treated with the indicated concentrations of doxorubicin in absence or presence of T12 (50 µM) and/or CFTR-inhibitor-172 (25 µM). Cells were cultured for additional 36 h and cell viability assessed as in FIG. 2. Lethal concentration 50 (LC50) for each combination of compounds is indicated in the table. Two-way ANOVA test indicates that differences among combinations of compounds are statistically significant (P<0.0001).

In qPCR studies we found that A549 cells co-treated with doxorubicin and T12 underwent up-regulation of CFTR gene (data not shown). CFTR encodes for an ATP-binding cassette transporter (ABCC7). ABC transporters are membrane proteins that mediate xenobiotic exclusion from cells and are involved in resistance of cancer cells to drugs (Dean 2009). CFTR/ABCC7 has not yet been described as a xenobiotic transporter but as a chloride channel (Vasiliou et al. 2009). However, the up-regulation of CFTR/ABCC7 mRNA in cells treated with doxorubicin and T12 prompted us to check its possible involvement in the response of A549 cells to drug treatments. Thus we used CFTR/ABCC7 inhibitor 172 in cell viability assays (FIG. 7). CFTR/ABCC7 inhibition significantly reduced cell viability in cultures treated with T12 with or without doxorubicin but not in cultures treated with doxorubicin alone. These results suggested CFTR/ABCC7 counteracts the effects of T12 on cells and inhibition of CFTR/ABCC7 is expected to enhance the therapeutic effects of T12.

Doxorubicin Enhances T12-Mediated Cancer Cell Migration Inhibition

Figure 8:
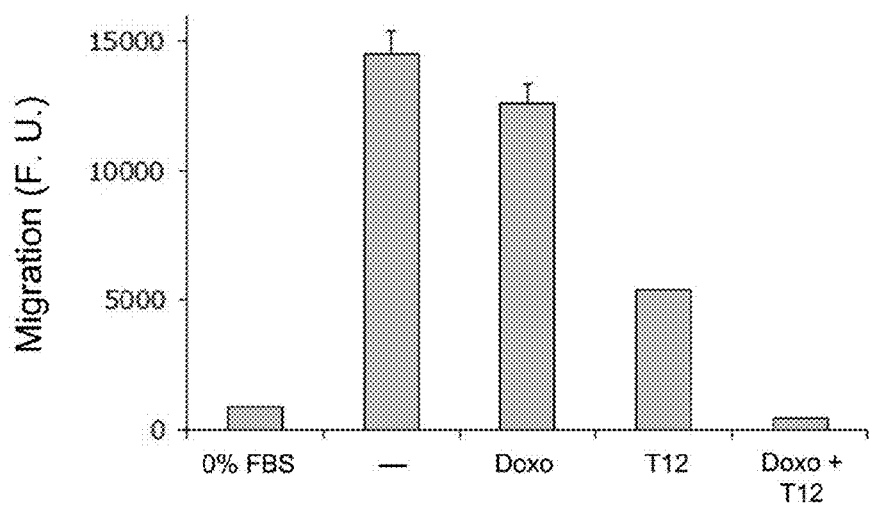
FIG. 8. T12 inhibits cancer cell migration. A modified Boyden chamber was used to measure migration as described in Methods and Experimental Design. Doxorubicin was used at 1 µM and T12 at 50 µM.

Using transwell migration chambers we found that T12 sharply inhibited cell migration of A549 cells and additional treatment with doxorubicin virtually arrested cell migration (FIG. 8).

T12 Enhances Doxorubicin-Mediated CSC/SP Depletion

Cancer cell line cultures typically contain a side-population (SP) of cells with characteristics of cancer stem cells (CSC) (Ho et al. 2007). This compartment stained with Hoescht 33342 and analyzed by flow cytometry show low dye content due to a high xenobiotic exportation activity. Incubation of cells with an exportation inhibitor (i.e. verapamil and fumitremorgin C) makes CSC/SP cells to increase dye content and thus allows identification and subsequent quantification of these cells (FIG. 9A). Treatment of A549 cells with either doxorubicin or T12 caused a reduction in the cell content of the CSC/SP compartment. Interestingly, co-treatment further shrank this compartment up to one fourth of the untreated cultures (FIG. 9B).

T12 Induces Doxorubicin Accumulation in CSC/SP Compartment

A549 cells treated with doxorubicin and T12 showed higher doxorubicin content than cells treated only with doxorubicin (FIG. 10A). However, T12-induced doxorubicin accumulation was not uniformly distributed in the culture and thus CSC/SP accumulated more doxorubicin than CTAC/MP compartment (FIG. 10B), suggesting that T12 impacted preferentially CSC/SP compartment.

T12 Enhances Anti-Tumor Activities of Doxorubicin In Vivo

Figure 11:
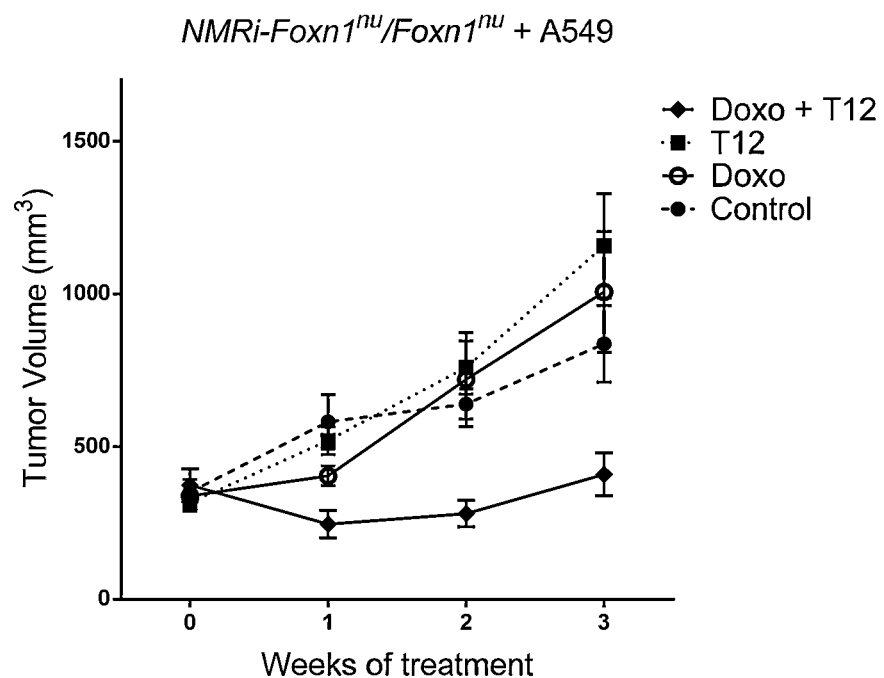
FIG. 11. T12 and doxorubicin are synergistic arresting growth of A549-based tumors. Nude mice bearing A549 xenografts were treated with the indicated compounds as indicated in Methods and Experimental Design. Indicated are the tumor size at the indicated times. In the table we present statistical analysis revealing that only combined treatment significantly reduced mean tumor volume (n=10 per group).
Figure 12:
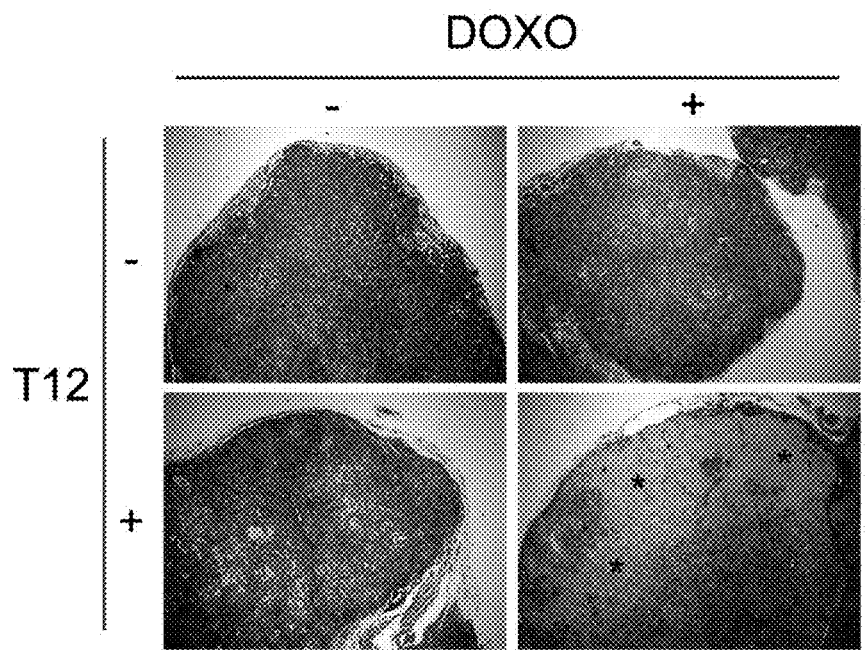
FIG. 12. T12 and doxorubicin are synergistic necrotizing A549-based tumors. Tumor samples from mice used in FIG. 11 were fixed in formalin, paraffin-embedded, subjected to Masson's trichrome staining and observed by optical microscopy. Necrotic areas are indicated with asterisks. Shown are representative images.

Nude mice were used for xenograft assays using human A549 cancer cells. At doses that either doxorubicin or T12 did not impaired tumor growth, the combined administration of these compounds resulted in tumor arrest (FIG. 11). After three weeks mice were sacrificed and tumors were dissected for analysis. Samples were fixed and embedded in paraffin for histological studies. Interestingly, the necrotic areas within the tumors were more extensive in mice which received combined treatment (FIG. 12). Moreover, combined treatment resulted in tumors that expressed lower levels of matrix metalloproteinase 10 (MMP-10) (FIG. 13), a biomarker associated with CSC/SP expansion and metastasis (Regala et al. 2011).

T12 Displays Major Biological Activity in Residual Cancer Cells

Figure 14:
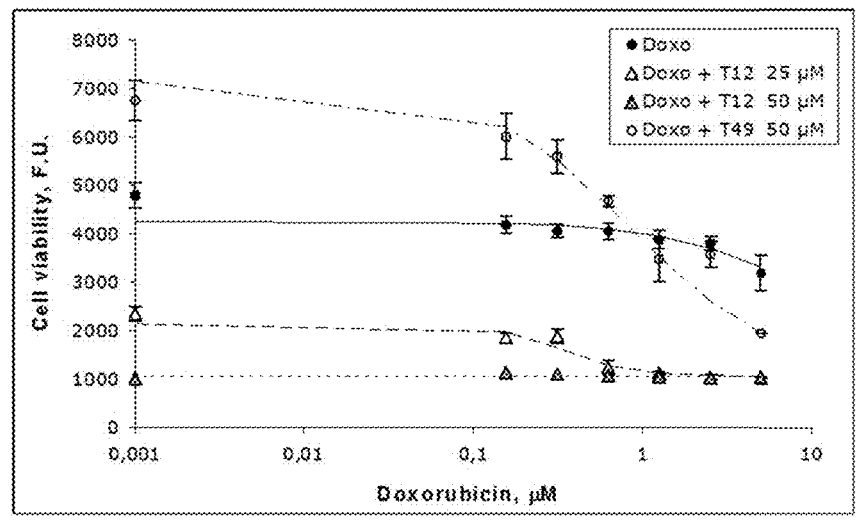
FIG. 14. T12 sharply reduce JLSM cell viability. A and B, JLSM cells were seeded (10.000 cells per $cm^2$) on collagen-I coated 96-well culture plate. Cells were settled for 4 h and subjected to the indicated treatments and cellular viability assayed after 36 h. Control bars represent cells without T12 or T49.
Figure 14:
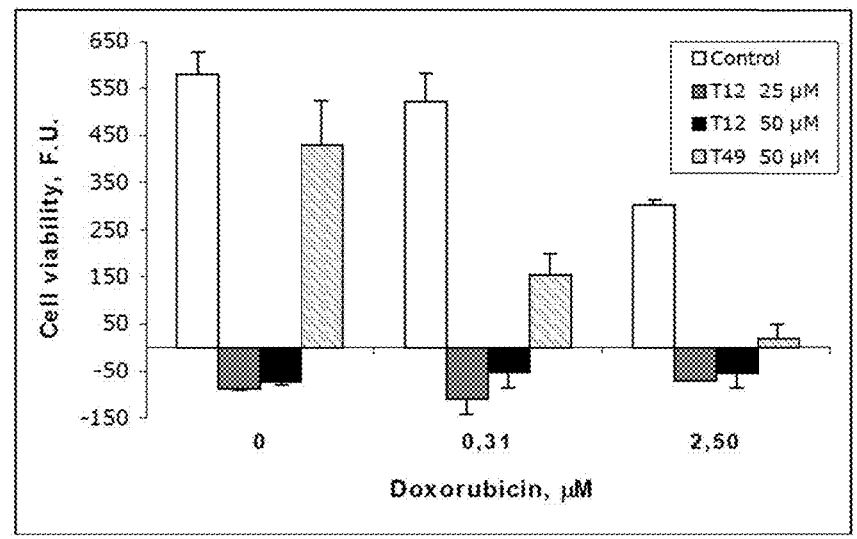

Collectively our data demonstrate that T12 is synergistic with doxorubicin in treating cancer because both compounds are inhibiting GPBP kinase activity in a different fashion. Furthermore, the evidence also suggests that synergism results from "unique" ability of T12 in reducing viability of cells at CSC/SP compartment. To further investigate this we established a cell line (JLSM) from a patient diagnosed of lung epidermoid carcinoma after three-round cisplatin-based chemotherapy which reduced tumor volume by ~50% and therefore expected to consist primarily in CSC/SP compartment (Alberts et al. 2007). Accordingly, immunohistochemical analysis of primary tumor supported this assumption since revealed that chemotherapy resulted in an increased number of cells expressing MRP/ABCC1 in the tumor and JLSM derived primary cultures expressed abundantly ABC family members (data not shown) which expression has been associated to CSC/SP compartment (Dean, 2009). As expected, JLSM primary cultures were highly sensitive to T12 and virtually resistant to doxorubicin (FIG. 14), further supporting lung cancer CSC/SP sensitivity to T12. In contrast related T49 (compound 22j in PCT/EP2010/006757 and WO 2011/054530) displayed no biological activity unless administered in combination with doxorubicin (FIG. 14).

Resistance to Doxorubicin and Expansion of CSC/SP Compartment in A549 Cultures are Associated with Increased GPBP Expression.

Figure 15:
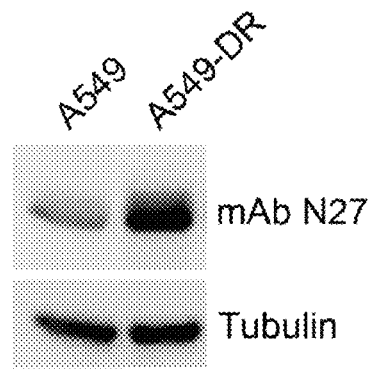
FIG. 15. GPBP is over-expressed in A549 cells resistant to doxorubicin. A549 cells treated for 4 weeks with 1 μM doxorubicin (A549-DR). Fifty μg of cellular lysates of A549 and A549-DR cells were analyzed by Western blot to assess the levels of GPBP using GPBP-specific mAb N27. Tubulin was stained with specific antibodies and used as loading control.

The data above suggest that doxorubicin resistance in A549 is mediated by increased GPBP expression. This was assessed by selecting A549 cells with doxorubicin and analyzed GPBP expression by Western blot (FIG. 15). Doxorubicin treatment and selection of A549 cells resulted in a cell lineage expressing high levels of GPBP. Consistent with these proposals, both doxorubicin-resistant A549 cells and A549 cells expressing increased recombinant GPBP displayed increased CDKN1A/p21 (cell cycle down regulator) and ABCC1 (xenobiotic transporter) expression (Table 2).

TABLE 2

|  | ID | statistic | p, adjusted |
|---|---|---|---|
| A549-GPBP | CDKN1A | 38.3488025 | 8.32E−05 |
|  | ABCC1 | 14.7277087 | 0.00075046 |
| A549-DR | CDKN1A | 33.5738597 | 0.00095941 |
|  | ABCC1 | 8.5582451 | 0.01077121 |

Table 2.

CDKNJA and ABCC1 expression is up-regulated in A549-cells expressing recombinant GPBP and in A549-DR cells. The table indicates the relative expression (statistic) and the statistical signification (p, adjusted) of the indicated genes and cell types respect wild type A549.

Chemoresistance is widely accepted to depend on epigenetic changes occurring at the CSC/SP compartment (Alberts et al. 2007). Accordingly GPBP-mediated doxorubicin resistance is expected to occur on CSC/SP compartment. To test this we cultured A549 cells in the absence of serum using culture conditions known to expand CSC/SP compartment. Expansion of CSC/SP compartment associated with increased GPBP expression (FIG. 16) and increased sensitivity to T12 biological action (LC50 of 15 µM vs 125 µM) (data not shown).

Discussion

Figure 2:
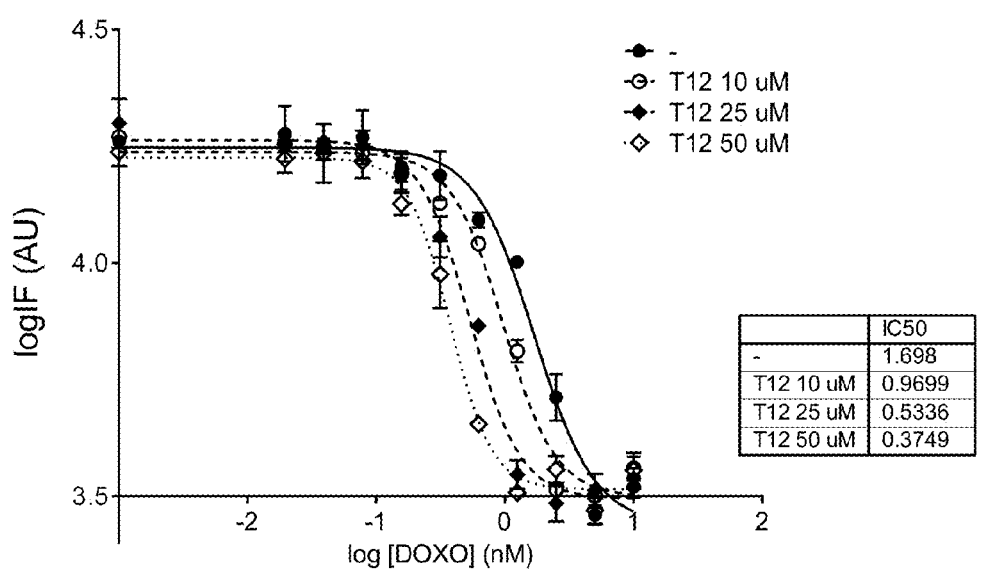
FIG. 2. T12 is synergic with doxorubicin reducing A549 cells viability. Cells were seeded in 96-well plates and treated with the indicated compound combinations. The cellular viability (cell number) was measured with alamarBlue® and arbitrary units of fluorescence after 36 h of treatment (vertical axis). T12 did not alter cell viability and it was synergic with doxorubicin in a dose dependent fashion. Each combination was analyzed in quadruplicate, and shown are the mean and standard deviation of each combination on a logarithmic plot and the best fitting curves. Lethal concentration 50 (LC50) for each combination of compounds is indicated in the table. Two-way ANOVA test indicates that differences among combinations of compounds are statistically significant (P<0.0001).
Figure 9:
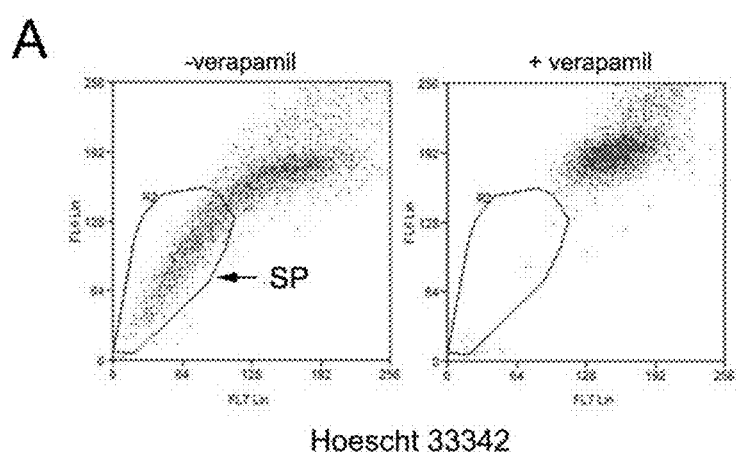
FIG. 9. T12 depletes the CSC/SP compartment of A549 cell cultures. A, cultures of A549 cells were incubated with Hoescht 33342 in the absence (−) or presence (+) of verapamil (50 µM) and fumitremorgin C (10 µM). Circled area (R2) denotes the region containing the flow cytometry events representing CSC/SP cells. B, shown are the relative abundance of CSC/SP cells (%) in cell cultures untreated (control) or treated with the indicated compounds.
Figure 9:
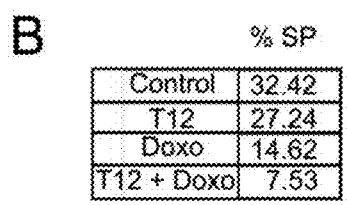
Figure 13:
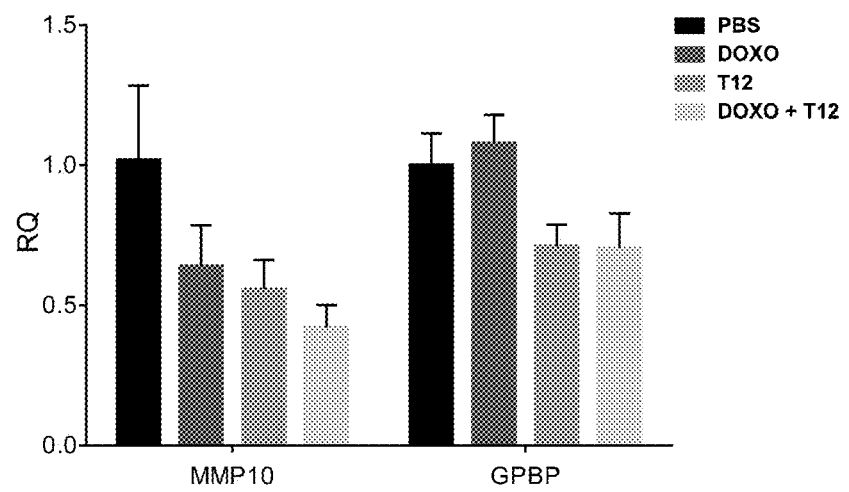
FIG. 13. T12 and doxorubicin are synergistic reducing MMP10 expression in A549-based tumors. mRNA extracted from tumor samples of mice used in FIG. 11 were analyzed by qPCR for assessment of MMP10 and COL4A3BP (GPBP) expression (n=5).

Both doxorubicin and T12 are inhibitors of GPBP kinase activity, however, doxorubicin displays much higher affinity for GPBP than T12 likely binding a different region in GPBP (FIG. 1). Doxorubicin and T12 are synergistic reducing cell viability (biological activity) of tumor cells (FIG. 2) and this collaborative effect is due, at least in part, to doxorubicin down regulating GPBP kinase activity. Moreover, doxorubicin biological activity is exerted at both CSC/SP (FIG. 9) and CTAC/MP (FIG. 2) compartments whereas T12 only displayed biological activity at CSC/SP compartment (FIGS. 2, 9 and 14). Interestingly, T12 enhanced biological activity of doxorubicin at both CSC/SP (FIG. 9) and CTAC/MP (FIG. 2) compartments. Collectively, the data suggest that GPBP is critical for cancer cell homeostasis and differences in biological activity between T12 and doxorubicin relay on differential GPBP binding site/affinity. Several lines of evidence indicate that high-affinity inhibition of GPBP results in a rebound effect on GPBP synthesis (FIG. 15 and PCT/EP12/052923 WO 2012/113785). In contrast, no evidence for increased expression of GPBP has been associated with T12 treatment of A549 cells when cultured either in vitro or in vivo (FIG. 13 and data not shown). Therefore reduction of doxorubicin LC50 when treating A549 cells in the presence of T12 (FIG. 2) is expected to prevent reactive GPBP expression and occurrence of chemoresistance. The administration of T12 to animal models using sub-therapeutic doses of doxorubicin supports these conclusions (FIGS. 11-13).

Figure 10:
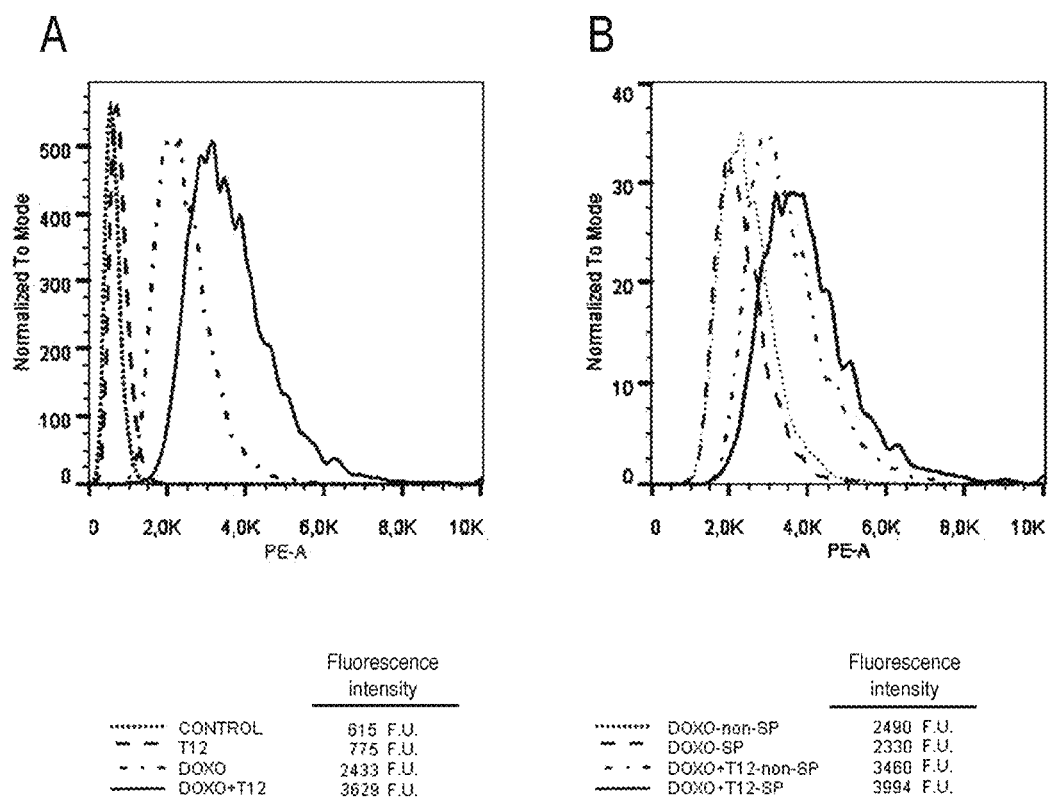
FIG. 10. T12 enhances doxorubicin accumulation, preferentially in CSC/SP cells. A549 cultures were untreated (control) or treated with doxorubicin (1 µM) and/or T12 (50 µM). A, doxorubicin content was measured by flow cytometry using the PE channel. Represented are fluorescence intensity values. The increased amount of doxorubicin is evidenced by the rightwards displacement of the fluorescence peak. B, CSC/SP and CTAC/MP compartments were identified as in FIG. 9 and the doxorubicin content of cells was determined as in A.

Low-affinity GPBP inhibition (T12) was sufficient to exert biological activity at CSC/SP compartment (FIGS. 9 and 14). This suggests that GPBP expression is more critical maintaining cell homeostasis at CSC/SP than at CTAC/MP compartment. GPBP promotes protein secretion (Fugmann et al. 2007) and therefore also protein translocation to plasma membrane. It has been proposed that the unique ability of CSC/SP cells to pump xenobiotic outside makes cells from this compartment especially resistant to drugs (Dean 2009). The evidence indicates that in the presence of T12 cancer cells accumulates doxorubicin. However, this effect was comparatively more evident at CSC/SP than at CTAC compartment (FIG. 10). Doxorubicin increases the expression of CFTR/ABCC7 (data not shown), a chloride channel structurally related with ABC xenobiotic transporter family. ABC transporter family is typically more expressed at the CSC/SP compartment and this has been related with the resistance of CSC/SP to conventional antitumor drugs (Dean 2009, Vasiliou et al. 2009). Interestingly, T12 enhances doxorubicin-dependent increased CFTR/ABCC7 expression (data not shown) and a specific inhibitor of CFTR/ABCC7 enhanced biological activity of T12 in the absence of doxorubicin (FIG. 7), suggesting that T12 and transporter inhibitor collaborate in reducing cell viability at the CSC/SP compartment.

Our data indicate that T12 displays an "unexpected" low-affinity inhibition of GPBP but does not induce the expression of GPBP or CFTR/ABCC7. In contrast, doxorubicin which also "unexpectedly" displays high-affinity inhibition of GPBP induces the expression of both GPBP and CFTR/ABCC7 and renders cancer cells resistant to treatment. Combination of doxorubicin with T12 severely decreases both chemoresistance and cancer cell viability at both CSC/SP (FIG. 9) and CTAC/MP (FIG. 2) compartment and therefore efficiently impairs tumor growth in animal models. Furthermore, combination of T12 and CFTR/ABCC7-172 inhibitor, which is expected to severely impact cell viability at the CSC/SP compartment, provides a novel strategy to treat cancer.

The data discussed above mainly refers to human lung carcinoma cell line A549 and derived tumors. In order to explore the scope of our findings in the clinical setting we analyzed primary cultures derived from a patient with lung epidermoid carcinoma after the patient underwent three-round cisplatin-based chemotherapy that reduced tumor size by 50% (data not shown). Culture was expected to be enriched in CSC/SP since conventional chemotherapy exerts biological activity mainly at CTAC/MP compartment. Interestingly, the corresponding primary cultures were highly sensitive to T12 and virtually resistant to doxorubicin (FIG. 14), further supporting lung cancer CSC/SP sensitivity to T12.

T12 showed biological activity against patient's cancer cells in contrast with doxorubicin and related T49 (compound 22j in PCT/EP2010/006757 and WO 2011/054530) which displayed no biological activity (FIG. 14). However, T49 and doxorubicin were synergistic and combined displayed biological activity on these cells (FIG. 14). The latter suggests that GPBP binding affinity of individual $Q_2$ peptidomimetics will be critical in regulating biological activity at CSC/SP compartment.

Figure 16:
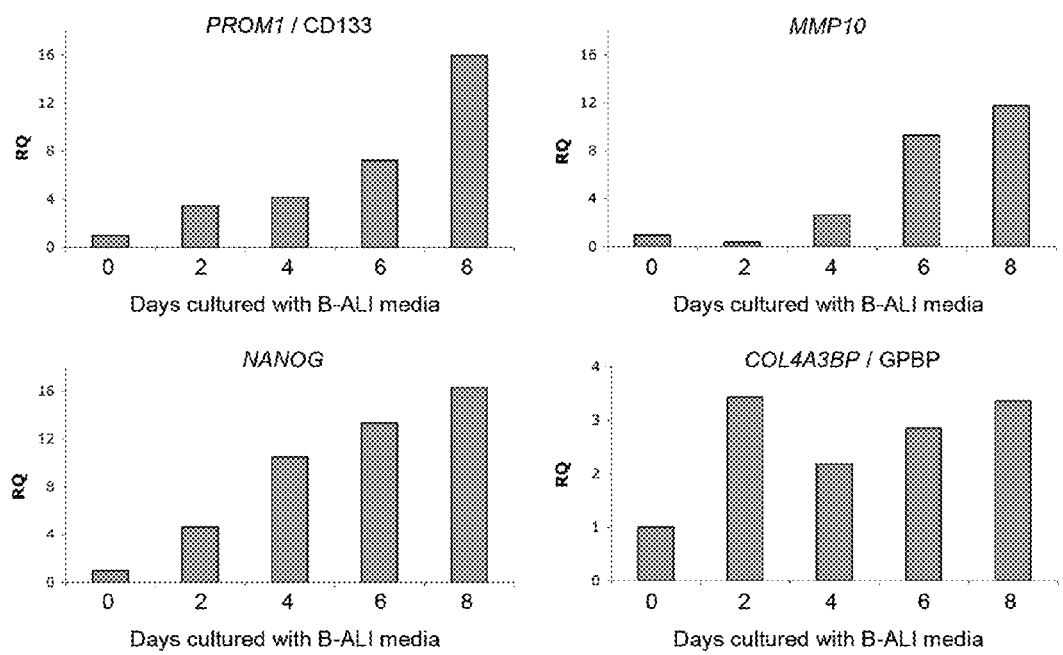
FIG. 16. GPBP is over-expressed in A549 cells grown in B-ALI media that allows CSC/SP expansion. Bars represent the relative expression of the indicated genes in A549 cells grown with the indicated culture medium during the indicated times. A549 cells grown in DMEM: Ham's F12 medium supplemented with 2 mM L-glutamine and 10% fetal bovine serum (day 0) were used as reference.

Doxorubicin-resistant A549 cells and A549 expressing recombinant GPBP were found to express increased CDKN1A/p21 (cyclin-dependent kinase inhibitor 1A) and MRP/ABCC1 (multidrug resistance-associated protein 1) mRNA levels (Table 2). Pathological analysis of patient tumor showed increased expression of CDKN1A/p21 and MRP/ABCC1 polypeptides in primary tumor upon cisplatin treatment (data not shown). CDKN1A/p21 expression increases in response to DNA damage (Bunz et al. 1998) and its down-regulation enhances cell cycle progression (Seoane et al. 2002). Consequently, reactive GPBP expression in response to chemotherapy is expected to mediate CDKN1A/p21-dependent cell cycle arrest and chemoresistance against antimitotic drugs. Inhibition of GPBP is expected to reduce translocation of ABC transporters to the plasma membrane and reduce capacity of cancer cells to pump out chemotherapeutic drugs. Thus data suggest that a general mechanism of chemoresistance results from an increase GPBP expression which up regulates CDKN1A/p21 and arrest cell division, making cells resistant to anti-mitotic agents. Similarly, through up regulation of MRP/ABCC1, GPBP also enhances drug-efflux to the extracellular compartment making cells more resistant to anti-cancer treatments. A lower proliferation rate and increased expression of ABC transporters are characteristic of CSC/SP compartment, suggesting that in tumors major GPBP expression occurs in CSC/SP compartment. Consistently, in culture conditions in which A549 cells expand CSC/SP compartment we found progressive increase of GPBP expression (FIG. 16).

Collectively our data indicate that any chemotherapeutic treatment which increases GPBP expression at CSC/SP compartment will benefit of treatment with T12 and related compounds. While the examples have focused on doxorubicin as the anti-tumor agent, we have seen that CSC derived from a uterine cancer were highly sensitive to a GPBP-1 inhibitor related to T12 (T55), another peptidomimetic we have tested (data not shown). Furthermore we generated data indicating that T12 also was synergistic with paclitaxel, which has a different mechanism of action than topoII inhibitors doxorubicin and etoposide.

REFERENCES

Alberts B, Johnson A, Lewis J, Raff M, Roberts K, Walter P, 2007. Molecular Biology of the Cell, 5th Ed., ISBN: 9780815341055

Bartek J, Lukas J. 2001. Mammalian G1- and S-phase checkpoints in response to DNA damage. *Curr. Opin. Cell. Biol.* 13: 738-47.

Benjamini Y, Hochberg Y. 1995. Controlling the False Discovery Rate: a Practical Powerful Approach to Multiple Testing. J R Statist Soc B, 57: 289-300.

Bunz F, Dutriaux A, Lengauer C, Waldman T, Zhou S, Brown J P, Sedivy J M, Kinzler K W, Vogelstein B. 1998. Requirement for p53 and p21 to sustain G2 arrest after DNA damage. *Science.* 282: 1497-501.

Dean M. 2009. ABC Transporters, Drug Resistance, and Cancer Stem Cells. *J. Mammary Gland. Biol. Neoplasia.* 14: 3-9.

Faizul F M, Abdul Kadir H, Tayyab S. 2008. Spectroscopic studies on the binding of bromocresol purple to different serum albumins and its bilirubin displacing action. *J. Photochem. Photobiol. B.* 90:1-7.

Fugmann T, Hausser A, Schoffler P, Schmid S, Pfizenmaier K, Olayioye M A. 2007. Regulation of secretory transport by protein kinase D-mediated phosphorylation of the ceramide transfer protein. *J. Cell. Biol.* 178: 15-22.

Ho M M, Ng A V, Lam S, Hung J Y. 2007. Side population in human lung cancer cell lines and tumors is enriched with stem-like cancer cells. *Cancer Res.* 67: 4827-33.

Kim H, Jang C, Choe J, Sohn J, Kim J 2012. Phenylbutyric acid induces the cellular senescence through an Akt/p21/waf signaling pathway. *Biochem. Biophys. Res. Commun.* 422: 213-18.

Lai H C, Yeh Y C, Ting C T, Lee W L, Lee H W, Wang L C, Wang K Y, Lai H C, Wu A, Liu T J. 2010. *Eur. J. Pharmacol.* 644: 176-87.

Lazebnik Y A, Kaufmann S H, Desnoyers S, Poirier G G, Earnshaw W C. 1994. Cleavage of poly(ADP-ribose) polymerase by a proteinase with properties like ICE. *Nature.* 371: 346-7.

Mihailidou C, Papazian I, Papavassiliou A, Kiaris H. 2010. CHOP-dependent regulation of p21/waf1 during ER stress. *Cell. Physiol. Biochem.* 25: 761-66.

Pommier Y, Leo E, Zhang H, Marchand C. 2010. DNA topoisomerases and their poisoning by anticancer and antibacterial drugs. Chem. Biol. 17: 421-33.

Raya A, Revert F, Navarro S, Saus J. 1999. Characterization of a novel type of serine/threonine kinase that specifically phosphorylates the human goodpasture antigen. *J. Biol. Chem.* 274: 12642-12649.

Raya A, Revert-Ros F, Martinez-Martinez P, Navarro S, Rosello E, Vieites B, Granero F, Forteza J, Saus J. 2000. Goodpasture antigen-binding protein, the kinase that phosphorylates the Goodpasture antigen, is an alternatively spliced variant implicated in autoimmune pathogenesis. *J. Biol. Chem.* 275: 40392-9.

Regala R P, Justilien V, Walsh M P, Weems C, Khoor A, Murray N R, Fields A P. 2011. Matrix metalloproteinase-10 promotes Kras-mediated bronchio-alveolar stem cell expansion and lung cancer formation. *PLoS One.* 6: e26439.

Revert F, Merino R, Monteagudo C, Macias J, Peydró A, Alcácer J, Muniesa P, Marquina R, Blanco M, Iglesias M, Revert-Ros F, Merino J, Saus J. 2007. Increased Goodpasture antigen-binding protein expression induces type IV collagen disorganization and deposit of immunoglobulin A in glomerular basement membrane. *Am. J. Pathol.* 171: 1419-30.

Revert F, Ventura I, Martinez-Martinez P, Granero-Moltó F, Revert-Ros F, Macías J, Saus J. 2008. Goodpasture antigen-binding protein is a soluble exportable protein that interacts with type IV collagen. Identification of novel membrane-bound isoforms. *J. Biol. Chem.* 283: 30246-55.

Saus J, Revert F, Revert-Ros F. 2008. Goodpasture antigen-binding protein isoforms and protein misfolded-mediated disorders. U.S. Pat. No. 7,326,768.

Saus J, Fustero S, Sanz-Cervera J F, Pérez-Payá E, Blasco R, Revert-Ros F, Revert F. 2010. GPBP inhibition using $Q_2$ peptidomimetics. U.S. patent application Ser. No. 12/940, 598.

Seoane J, Le H V, Massague J. 2002. Myc suppression of the p21(Cip1) Cdk inhibitor influences the outcome of the p53 response to DNA damage. Nature. 419: 729-34.

Sithanandam G, Formwald L W, Fields J, Anderson L M. 2005. Inactivation of ErbB3 by siRNA promotes apoptosis and attenuates growth and invasiveness of human lung adenocarcinoma cell line A549. *Oncogene.* 24: 1847-59.

Swanton C, Marani M, Pardo O, Warne P H, Kelly G, Sahai E, Elustondo F, Chang J, Temple J, Ahmed A A, Brenton J D, Downward J, Nicke B. 2007. Regulators of mitotic arrest and ceramide metabolism are determinants of sensitivity to paclitaxel and other chemotherapeutic drugs. *Cancer Cell.* 11: 498-512.

Vasiliou V, Vasiliou K, Nebert D W. 2009. Human ATP-binding cassette (ABC) transporter family. *Hum. Genomics.* 3: 281-90.

Zinszner H, Kuroda M, Wang X, Batchvarova N, Lightfoot R T, Remotti H, Stevens J L, Ron D. 1998. CHOP is implicated in programmed cell death in response to impaired function of the endoplasmic reticulum. *Genes Dev.* 12: 982-95.

We claim:

1. A pharmaceutical composition, comprising:
   (a) an antitumor drug or a pharmaceutically acceptable salt thereof, wherein the antitumor drug is selected from the group consisting of paclitaxel, a topoisomerase II inhibitor, 5-fluorouracil (5-FU), and cisplatin;
   (b) a compound of formula:

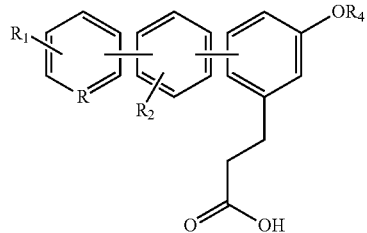

or a pharmaceutically acceptable salt thereof, wherein:
   R is selected from N and $CR_3$;
   $R_1$ is hydrogen or $C_1$-$C_6$ alkoxy;
   $R_2$ is $C_1$-$C_6$ alkyl or halo($C_1$-$C_6$ alkyl);
   $R_3$, if present, is halogen, $C_1$-$C_6$ alkyl, or halo($C_1$-$C_6$ alkyl); and
   $R_4$ is H or $C_1$-$C_6$ alkyl; and
   (c) a pharmaceutically acceptable carrier.

2. The pharmaceutical composition of claim 1, wherein:
   $R_1$ is hydrogen or methoxy;
   $R_2$ is methyl, fluoromethyl, or difluoromethyl;
   $R_3$, if present, is chloro, methyl or trifluoromethyl; and
   $R_4$ is H or methyl.

3. The pharmaceutical composition of claim 2, wherein $R_1$ is hydrogen.

4. The pharmaceutical composition of claim 3, wherein $R_4$ is methyl.

5. The pharmaceutical composition of claim 1, wherein the compound is:

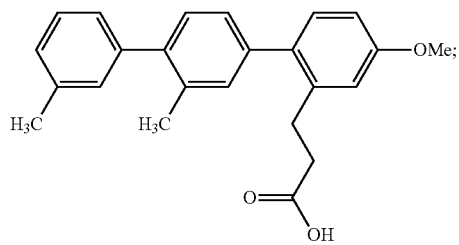 [SMILES: COc1ccc(-c2ccc(-c3cccc(C)c3)c(C)c2)c(CCC(=O)O)c1]

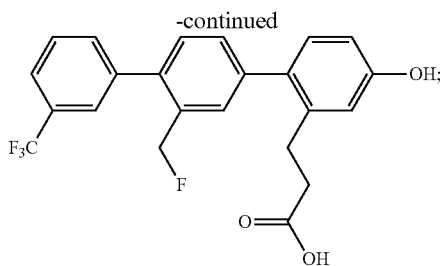

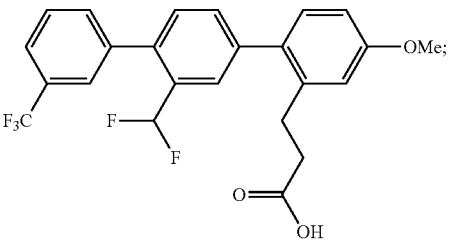

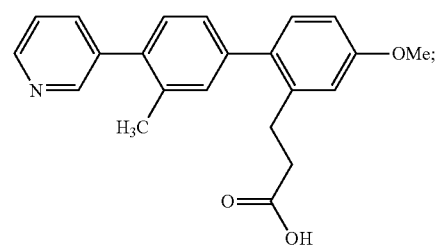

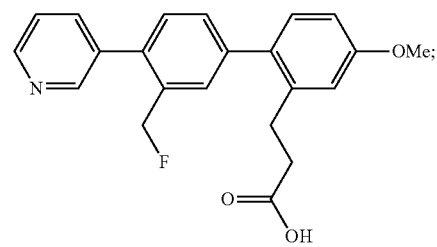

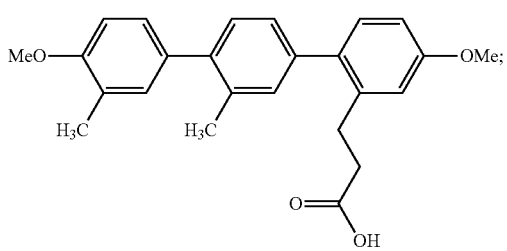

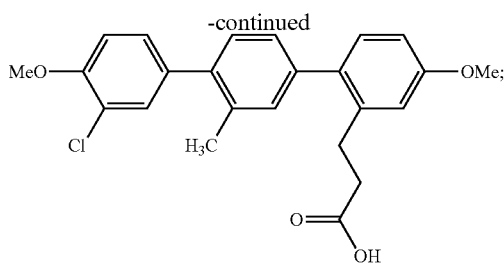

or a pharmaceutically acceptable salt thereof.

6. The pharmaceutical composition of claim 1, wherein the compound is:

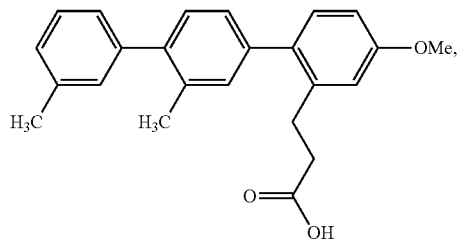

or a pharmaceutically acceptable salt thereof.

7. The pharmaceutical composition of claim 1, wherein the antitumor drug is a topoisomerase II inhibitor.

8. The pharmaceutical composition of claim 7, wherein the topisomerase II inhibitor comprises an anthracyclin drug.

9. The pharmaceutical composition of claim 1, wherein the antitumor drug is selected from the group consisting of doxorubicin and etoposide.

10. The pharmaceutical composition of claim 1, further comprising a p21 inhibitor.

11. The pharmaceutical composition of claim 10, wherein the p21 inhibitor is selected from the group consisting of p21 antibodies, p21 siRNA, p21 shRNA, p21 antisense compounds and p21 expression inhibitors selected from the group consisting of 2-(2-Chlorophenyl)-5,7-dihydroxy-8-[(3S,4R)-3-hydroxy-1-methylpiperidin-4-yl]-4H-chromen-4-one (Flavopiridol), (1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^{4,9}]hexatriaconta-16,24,26,28-tetraen-12-yl]propyl]-2-methoxycyclohexyl 3-hydroxy-2-(hydroxymethyl)-2-methylpropanoate (Temsirolimus), (3R,4S,5S,6R,7R,9R,11S,12R,13S,14R)-6-{[(2S,3R,4S,6R)-4-(dimethylamino)-3-hydroxy-6-methyloxan-2-yl]oxy}-14-ethyl-7,12,13-trihydroxy-4-{[(2R,4R,5 S,6S)-5-hydroxy-4-methoxy-4,6-dimethyloxan-2-yl]oxy}-3,5,7,9,11,13-hexamethyl-10-(2,4,7-trioxa-1-azaoctan-1-ylidene)-1-oxacyclotetradecan-2-one (Roxithromycin), 6-Hydroxy-2-(4-hydroxyphenyl)benzo[b]thien-3-yl][4-[2-(1-piperidinyl)ethoxy]phenyl]methanone hydrochloride (Raloxifene hydrochloride), (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.1^{4,7}.0^{5,28}]triaconta-1(28),2,4,9,19,21,25(29),26-octaen-13-yl acetate (Rifampicin), [(8R,9S,10R,13S,14S,17R)-17-acetyl-6,10,13-trimethyl-3-oxo-2,8,9,11,1214,15,16-octahydro-1H-cyclopenta[a]phenanthren-17-yl]acetate (Megestrol Acetate), 8-(4-Amino-1-methylbutylamino)-6-methoxyquinoline diphosphate salt (Primaquine diphosphate), Potassium; [2-butyl-5-chloro-3-[[4-[2-(1,2,3-triaza-4-azanidacyclopenta-2,5-dien-5-yl)phenyl]phenyl]methyl]imidazol-4-yl]methanol (Losartan potassium), (2S)-3-methyl-2-[pentanoyl-[[4-[2-(2H-tetrazol-5-yl)phenyl]phenyl]methyl]amino]butanoic acid (Valsartan), (Z)-but-2-enedioic acid; 2-(2,2-dicyclohexylethyl)piperidine (Perhexiline maleate), 3-O-methyl 5-O-(2-methylpropyl) 2,6-dimethyl-4-(2-nitrophenyl)-1,4-dihydropyridine-3,5-dicarboxylate (Nisoldipine), or pharmaceutically acceptable salts thereof.

12. The pharmaceutical composition of claim 1, further comprising an inhibitor of ATP-binding cassette transporter 7 (ABCC7).

13. The pharmaceutical composition of claim 12, wherein the ABCC7 inhibitor is selected from the group consisting of 3-[(3-Trifluoromethyl)phenyl]-5-[(4-carboxyphenyl)methylene]-2-thioxo-4-thiazolidinone (172), 7,9-Dimethyl-11-phenyl-6-(5-methylfuran-2-yl)-5,6-dihydro-pyrimido-[4',5'-3,4]pyrrolo[1,2-a]quinoxaline-8,10-(7H,9H)-dione (PPQ-102), 1-[(2,4-Dichlorophenyl)methyl]-1H-indazole-3-carboxylic acid (Lonidamine), trans-N-[6-Cyano-3,4-dihydro-3-hydroxy-2,2-dimethyl-2H-1-benzopyran-4-yl]-N-methyl-ethanesulfonamide (Chromanol 293B), 1-[[p-[2-(5-chloro-o-anisamido)ethyl]phenyl]sulfonyl]-3-cyclohexylurea (Glibenclamide), and N-(2-Naphthalenyl)-((3,5-dibromo-2,4-dihydroxyphenyl)methylene)glycine hydrazide (GlyH-10), or pharmaceutically acceptable salts thereof.

14. A method of treating a tumor, comprising administering to a subject with a tumor an amount effective to treat the tumor of:
(a) an antitumor drug or a pharmaceutically acceptable salt thereof, wherein the antitumor drug is selected from the group consisting of paclitaxel, a topoisomerase II inhibitor, 5-fluorouracil (5-FU), and cisplatin; and
(b) a compound of formula:

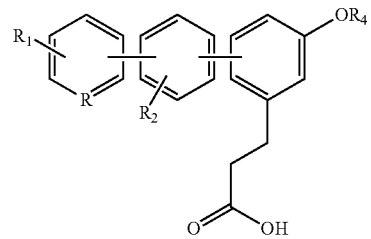

or a pharmaceutically acceptable salt thereof, wherein:
R is selected from N and $CR_3$;
$R_1$ is hydrogen or $C_1$-$C_6$ alkoxy;
$R_2$ is $C_1$-$C_6$ alkyl or halo($C_1$-$C_6$ alkyl);
$R_3$, if present, is halogen, $C_1$-$C_6$ alkyl, or halo($C_1$-$C_6$ alkyl); and
$R_4$ is H or $C_1$-$C_6$ alkyl.

15. The method of claim 14, further comprising administering to the subject an amount effective of a p21 inhibitor to inhibit p21 expression and/or activity in the tumor.

16. The method of claim 15, wherein the p21 inhibitor is selected from the group consisting of p21 antibodies, p21 siRNA, p21 shRNA, p21 antisense compounds and p21 expression inhibitors selected from the group consisting of 2-(2-Chlorophenyl)-5,7-dihydroxy-8-[(3S,4R)-3-hydroxy-1-methylpiperidin-4-yl]-4H-chromen-4-one (Flavopiridol), (1R,2R,4S)-4-[(2R)-2-[(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20- pentaoxo-11,36-dioxa-4-azatricyclo[30.3.1.0^{4,9}] hexatriaconta-16,24,26,28-tetraen-12-yl]propyl]-2-methoxycyclohexyl 3-hydroxy-2-(hydroxymethyl)-2-methylpropanoate (Temsirolimus), (3R,4S,5S,6R,7R,9R,11S,12R,13S,14R)-6-{[(2S,3R,4S,6R)-4-(dimethylamino)-3-hydroxy-6-methyloxan-2-yl]oxy}-14-ethyl-7,12,13-trihydroxy-4-{[(2R,4R,5S,6S)-5-hydroxy-4-methoxy-4,6-dimethyloxan-2-yl]oxy}-3,5,7,9,11,13-hexamethyl-10-(2,4,7-trioxa-1-azaoctan-1-ylidene)-1-oxacyclotetradecan-2-one (Roxithromycin),6-Hydroxy-2-(4-hydroxyphenyl)benzo[b]thien-3-yl][4-[2-(1-piperidinyl)ethoxy]phenyl]methanone hydrochloride (Raloxifene hydrochloride), (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.$^{14,7}$.0$^{5,28}$]triaconta-1(28),2,4,9,19,21,25(29),26-octaen-13-yl acetate (Rifampicin), [(8R,9S,10R,13S,14S,17R)-17-acetyl-6,10,13-trimethyl-3-oxo-2,8,9,11,1214,15,16-octahydro-1H-cyclopenta[a]phenanthren-17-yl]acetate (Megestrol Acetate), 8-(4-Amino-1-methylbutylamino)-6-methoxyquinoline diphosphate salt (Primaquine diphosphate), Potassium; [2-butyl-5-chloro-3-[[4-[2-(1,2,3-triaza-4-azanidacyclopenta-2,5-dien-5-yl)phenyl]phenyl]methyl]imidazol-4-yl]methanol (Losartan potassium), (2S)-3-methyl-2-[pentanoyl-[[4-[2-(2H-tetrazol-5-yl)phenyl]phenyl]methyl]amino]butanoic acid (Valsartan), (Z)-but-2-enedioic acid; 2-(2,2-dicyclohexylethyl)piperidine (Perhexiline maleate), 3-O-methyl 5-O-(2-methylpropyl) 2,6-dimethyl-4-(2-nitrophenyl)-1,4-dihydropyridine-3,5-dicarboxylate (Nisoldipine), or pharmaceutically acceptable salts thereof.

17. The method of claim 14, further comprising administering to the subject an amount effective of an inhibitor of ATP-binding cassette transporter 7 (ABCC7) to inhibit ABCC7 expression and/or activity in the tumor.

18. The method of claim 17, wherein the ABCC7 inhibitor is selected from the group consisting of ABCC7 antibodies, ABCC7 siRNA, ABCC7 shRNA, ABCC7 antisense compounds and ABCC7 expression inhibitors selected from the group consisting of 3-[(3-Trifluoromethyl)phenyl]-5-[(4-carboxyphenyl)methylene]-2-thioxo-4-thiazolidinone (172), 7,9-Dimethyl-11-phenyl-6-(5-methylfuran-2-yl)-5,6-dihydro-pyrimido-[4',5'-3,4]pyrrolo[1,2-a]quinoxaline-8,10-(7H,9H)-dione (PPQ-102), 1-[(2,4-Dichlorophenyl)methyl]-1H-indazole-3-carboxylic acid (Lonidamine), trans-N-[6-Cyano-3,4-dihydro-3-hydroxy-2,2-dimethyl-2H-1-benzopyran-4-yl]-N-methyl-ethanesulfonamide (Chromanol 293B), 1-[[p-[2-(5-chloro-o-anisamido)ethyl]phenyl]sulfonyl]-3-cyclo-hexylurea (Glibenclamide), and N-(2-Naphthalenyl)-((3,5-dibromo-2,4-dihydroxyphenyl)methylene)glycine hydrazide (GlyH-10), or pharmaceutically acceptable salts thereof.

19. The method of claim 14, wherein treating the tumor comprises reducing tumor metastasis.

20. The method of claim 14, wherein treating the tumor comprises depleting cancer stem cells in the tumor.

21. A method for treating a tumor, comprising administering to a subject with a tumor an amount effective to treat the tumor of
(a) an antitumor drug, wherein the antitumor drug is selected from the group consisting of paclitaxel, a topoisomerase II inhibitor, 5-fluorouracil (5-FU), and cisplatin; and
(b) a GPBP-1 inhibitor.

22. The method of claim 21, wherein the GPBP-1 inhibitor is a compound of formula:

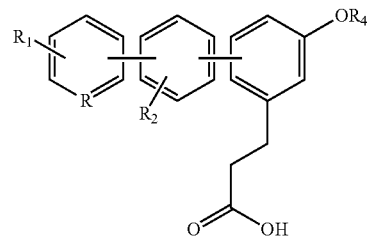

or a pharmaceutically acceptable salt thereof, wherein:
R is selected from N and CR$_3$;
R$_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —(CH$_2$)$_{1-5}$—C(O)($C_1$-$C_6$ alkoxy), —(CH$_2$)$_{1-5}$—C(O)NH$_2$, (aryl)$C_2$-$C_6$ alkyl, and (heteroaryl)$C_1$-$C_6$ alkyl;
R$_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl ($C_1$-$C_6$ alkyl);
R$_2$ is $C_1$-$C_6$ alkyl, halo($C_1$-$C_6$ alkyl), or hydroxy($C_1$-$C_6$ alkyl); and
R$_4$ is H, $C_1$-$C_6$ alkyl, —C(O)($C_1$-$C_{20}$ alkyl), or —(CH$_2$)$_{1-5}$—C(O)OH.

23. A method for reducing chemoresistance of a tumor, comprising administering to a subject with a tumor that is to be treated with a chemotherapeutic an amount effective of an inhibitor of ATP-binding cassette transporter 7 (ABCC7), or a pharmaceutically acceptable salt thereof, to inhibit ABCC7 expression and/or activity in the tumor.

24. A compound of formula:

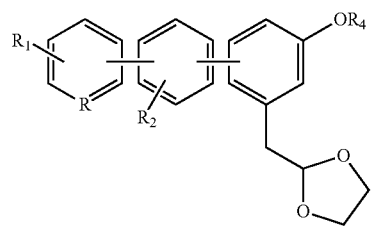

or a pharmaceutically acceptable salt thereof, wherein:
R is selected from N and CR$_3$;
R$_3$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —(CH$_2$)$_{1-5}$—C(O)($C_1$-$C_6$ alkoxy), —(CH$_2$)$_{1-5}$—C(O)NH$_2$, (aryl)$C_2$-$C_6$ alkyl, and (heteroaryl)$C_1$-$C_6$ alkyl;
R$_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl ($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C(O)OH, or —CH=CH—C(O)($C_1$-$C_6$ alkoxy); and $R_4$ is hydrogen, $C_1$-$C_6$ alkyl, or (aryl)$C_1$-$C_6$ alkyl.

25. A method of treating a tumor, comprising administering to a subject with a tumor an amount effective to treat the tumor of a compound of claim 24.

26. A method for reducing chemoresistance of a tumor, comprising administering to a subject with a tumor that is to be treated with a chemotherapeutic an amount effective of an inhibitor of p21, or a pharmaceutically acceptable salt thereof, to inhibit p21 expression and/or activity in the tumor.

27. The compound of claim 24, wherein $R_1$ is hydrogen or methoxy.

28. The compound of claim 24 wherein $R_2$ is methyl, fluoromethyl, or difluoromethyl.

29. The compound of claim 24 wherein $R_3$ is present, and is chloro, methyl or trifluoromethyl.

30. The compound of claim 24 wherein $R_4$ is H or methyl.

31. The compound of claim 24 wherein, $R_1$ is hydrogen.

32. The compound of claim 24 wherein $R_1$ is hydrogen or methoxy; $R_2$ is methyl, fluoromethyl, or difluoromethyl; $R_3$, if present, is methyl or trifluoromethyl; and $R_4$ is H or methyl.

33. The compound of claim 24 wherein $R_4$ is methyl.

34. A compound of the formula

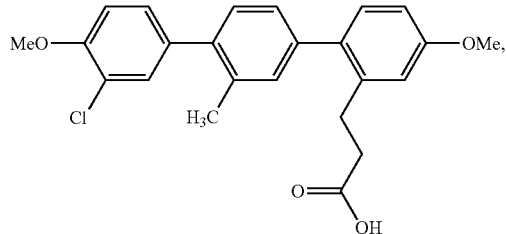 [SMILES: COc1ccc(-c2ccc(-c3ccc(OC)c(Cl)c3)c(C)c2)c(CCC(=O)O)c1]

or a pharmaceutically acceptable salt thereof.

35. A method of treating a tumor, comprising administering to a subject with a tumor an amount effective to treat the tumor of a compound of claim 34.

* * * * *

```
                              SEQUENCE LISTING

<160> NUMBER OF SEQ ID NOS: 12

<210> SEQ ID NO 1
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Optionally absent
<220> FEATURE:
<221> NAME/KEY: MISC_FEATURE
<222> LOCATION: (15)..(15)
<223> OTHER INFORMATION: X is E or Q
<220> FEATURE:
<221> NAME/KEY: MISC_FEATURE
<222> LOCATION: (16)..(25)
<223> OTHER INFORMATION: Optionally absent

<400> SEQUENCE: 1

Ala Thr Thr Ala Gly Ile Leu Ala Thr Leu Ser His Cys Ile Xaa Leu
1               5                   10                  15

Met Val Lys Arg Glu Asp Ser Trp Gln
            20                  25

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Ala Thr Thr Ala Gly Ile Leu Ala Thr Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Leu Met Val Lys Arg Glu Asp Ser Trp Gln
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic

<400> SEQUENCE: 4

Ser His Cys Ile Glu
1               5

<210> SEQ ID NO 5
<211> LENGTH: 5
```

```
<212> TYPE: PRT
<213> ORGANISM: Artificial Sequence
<220> FEATURE:
<223> OTHER INFORMATION: Synthetic

<400> SEQUENCE: 5

Ser His Cys Ile Gln
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Ile Leu Ala Thr Leu Ser His Cys Ile Glu Leu Met Val Lys Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ile Leu Ala Thr Leu Ser His Cys Ile Gln Leu Met Val Lys Arg
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Leu Ala Thr Leu Ser His Cys Ile Glu Leu Met Val Lys Arg
1               5                   10

<210> SEQ ID NO 9
<211> LENGTH: 265
<212> TYPE: PRT
<213> ORGANISM: Artificial Sequence
<220> FEATURE:
<223> OTHER INFORMATION: Synthetic

<400> SEQUENCE: 9

Arg Asp Glu Val Ile Gly Ile Leu Lys Ala Glu Lys Met Asp Leu Ala
1               5                   10                  15

Leu Leu Glu Ala Gln Tyr Gly Phe Val Thr Pro Lys Lys Val Leu Glu
                20                  25                  30

Ala Leu Gln Arg Asp Ala Phe Gln Ala Lys Ser Thr Pro Trp Gln Glu
            35                  40                  45

Asp Ile Tyr Glu Lys Pro Met Asn Glu Leu Asp Lys Val Val Glu Lys
        50                  55                  60

His Lys Glu Ser Tyr Arg Arg Ile Leu Gly Gln Leu Leu Val Ala Glu
65                  70                  75                  80

Lys Ser His Arg Gln Thr Ile Leu Glu Leu Glu Glu Lys Arg Lys
                85                  90                  95

His Lys Glu Tyr Met Glu Lys Ser Asp Glu Phe Ile Cys Leu Leu Glu
                100                 105                 110
```

```
Gln Glu Cys Glu Arg Leu Lys Lys Leu Ile Asp Gln Glu Ile Lys Ser
            115                 120                 125
Gln Glu Glu Lys Glu Gln Lys Glu Lys Arg Val Thr Thr Leu Lys
        130                 135                 140
Glu Glu Leu Thr Lys Leu Lys Ser Phe Ala Leu Met Val Val Asp Glu
145                 150                 155                 160
Gln Gln Arg Leu Thr Ala Gln Leu Thr Leu Gln Arg Gln Lys Ile Gln
                165                 170                 175
Glu Leu Thr Thr Asn Ala Lys Glu Thr His Thr Lys Leu Ala Leu Ala
            180                 185                 190
Glu Ala Arg Val Gln Glu Glu Gln Lys Ala Thr Arg Leu Glu Lys
        195                 200                 205
Glu Leu Gln Thr Gln Thr Thr Lys Phe His Gln Asp Gln Asp Thr Ile
        210                 215                 220
Met Ala Lys Leu Thr Asn Glu Asp Ser Gln Asn Arg Gln Leu Gln Gln
225                 230                 235                 240
Lys Leu Ala Ala Leu Ser Arg Gln Ile Asp Glu Leu Glu Glu Thr Asn
                245                 250                 255
Arg Ser Leu Arg Lys Ala Glu Glu Glu
            260                 265

<210> SEQ ID NO 10
<211> LENGTH: 2110
<212> TYPE: DNA
<213> ORGANISM: Artificial Sequence
<220> FEATURE:
<223> OTHER INFORMATION: Synthetic

<400> SEQUENCE: 10
ggtggctatt ttgtccttgg gctgcctgtt ttcagctgct gcaaccacag ggatttcttc        60
tgttcaggcg ccatgtcaga accggctggg gatgtccgtc agaacccatg cggcagcaag       120
gcctgccgcc gcctcttcgg cccagtggac agcgagcagc tgagccgcga ctgtgatgcg       180
ctaatggcgg gctgcatcca ggaggcccgt gagcgatgga acttcgactt tgtcaccgag       240
acaccactgg agggtgactt cgcctgggag cgtgtgcggg ccttggcct gcccaagctc        300 taccttccca cggggccccg cgaggccgg gatgagttgg gaggaggcag gcggcctggc        360
acctcacctg ctctgctgca ggggacagca gaggaagacc atgtggacct gtcactgtct       420 tgtaccttg tgcctcgctc aggggagcag gctgaagggt ccccaggtgg acctggagac        480
tctcagggtc gaaaacggcg gcagaccagc atgacagatt ctaccactc caaacgccgg        540 ctgatcttct ccaagaggaa gccctaatcc gcccacagga agcctgcagt cctggaagcg       600
cgagggcctc aaaggcccgc tctacatctt ctgccttagt ctcagtttgt gtgtcttaat       660
tattatttgt gttttaattt aaacacctcc tcatgtacat accctggccg ccccctgccc       720
cccagcctct ggcattagaa ttatttaaac aaaaactagg cggttgaatg agaggttcct       780
aagagtgctg gcatttttta ttttatgaaa tactatttaa agcctcctca tcccgtgttc       840
tccttttcct ctctcccgga ggttgggtgg gccggcttca tgccagctac ttcctcctcc       900
ccacttgtcc gctgggtggt accctctgga ggggtgtggc tccttcccat cgctgtcaca       960
ggcggttatg aaattcaccc cctttcctgg acactcagac ctgaattctt tttcatttga      1020
gaagtaaaca gatggcactt tgaaggggcc tcaccgagtg ggggcatcat caaaaacttt      1080
ggagtcccct cacctcctct aaggttgggc agggtgaccc tgaagtgagc acagcctagg      1140
```

```
gctgagctgg ggacctggta ccctcctggc tcttgatacc cccctctgtc ttgtgaaggc    1200
agggggaagg tggggtcctg gagcagacca ccccgcctgc cctcatggcc cctctgacct    1260
gcactgggga gcccgtctca gtgttgagcc ttttccctct ttggctcccc tgtacctttt    1320
gaggagcccc agctacccct cttctccagc tgggctctgc aattcccctc tgctgctgtc    1380
cctccccctt gtcctttccc ttcagtaccc tctcagctcc aggtggctct gaggtgcctg    1440 tcccacccc accccagct caatggactg aaggggaag ggacacacaa gaagaagggc       1500
accctagttc tacctcaggc agctcaagca gcgaccgccc cctcctctag ctgtggggt     1560 gagggtccca tgtggtggca caggccccct tgagtgggt tatctctgtg ttaggggtat     1620
atgatggggg agtagatctt tctaggaggg agacactggc ccctcaaatc gtccagcgac    1680
cttcctcatc caccccatcc ctccccagtt cattgcactt tgattagcag cggaacaagg    1740
agtcagacat tttaagatgg tggcagtaga ggctatggac agggcatgcc acgtgggctc    1800
atatggggct gggagtagtt gtctttcctg gcactaacgt tgagcccctg gaggcactga    1860
agtgcttagt gtacttggag tattgggtc tgaccccaaa ccttccag ctcctgtaac       1920 atactggcct ggactgtttt ctctcggctc cccatgtgtc ctggttcccg tttctccacc    1980
tagactgtaa acctctcgag ggcagggacc acaccctgta ctgttctgtg tctttcacag    2040
ctcctcccac aatgctgaat atacagcagg tgctcaataa atgattctta gtgactttac    2100
ttgtaaaaaa                                                           2110
```

<210> SEQ ID NO 11
<211> LENGTH: 164
<212> TYPE: PRT
<213> ORGANISM: Artificial Sequence
<220> FEATURE:
<223> OTHER INFORMATION: Synthetic

<400> SEQUENCE: 11

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 12
<211> LENGTH: 21

```
<212> TYPE: DNA
<213> ORGANISM: Artificial Sequence
<220> FEATURE:
<223> OTHER INFORMATION: Synthetic
<220> FEATURE:
<223> OTHER INFORMATION: combined DNA/RNA

<400> SEQUENCE: 12
caaggaguca gacauuuuat t                                        21
```